United States Patent [19]
Wisnewski et al.

[11] Patent Number: 6,153,397
[45] Date of Patent: Nov. 28, 2000

[54] FLEA EPOXIDE HYDROLASE PROTEINS AND USES THEREOF

[75] Inventors: Nancy Wisnewski; Gary M. Silver; Katherine Callies Lo, all of Fort Collins; Kevin S. Brandt, Windsor, all of Colo.

[73] Assignee: Heska Corporation, Fort Collins, Colo.

[21] Appl. No.: 09/471,528

[22] Filed: Dec. 27, 1999

Related U.S. Application Data

[60] Division of application No. 09/182,816, Oct. 29, 1998, which is a continuation-in-part of application No. 08/989,510, Dec. 12, 1997, Pat. No. 6,037,160.

[51] Int. Cl.[7] .............................. C12N 9/14; A61K 38/46
[52] U.S. Cl. ........................ 435/18; 435/195; 424/94.6
[58] Field of Search .................... 424/6; 435/18, 435/195

[56] References Cited

U.S. PATENT DOCUMENTS 5,445,956   8/1995   Hammock et al. ..................... 435/195

FOREIGN PATENT DOCUMENTS 0 516 590 A1   12/1992   European Pat. Off. .

OTHER PUBLICATIONS

Khlebodarova et al., 1996, "A Comparative Analysis of Juvenile Hormone Metabolyzing Enzymes in Two Species of Drosophila During Development," *Insect Biochem. Molec. Biol.*, vol. 26:8–9, pp. 829–835.

Roe et al., 1996, "Mechanism of Action and Cloning of Epoxide Hydrolase From the Cabbage Looper, *Trichoplusia ni*," *Archives of Insect Biochemistry and Physiology*, vol. 32, pp. 527–535.

Touhara et al., 1993, "Juvenile Hormone Epoxide Hydrolase," *The Journal of Biological Chemistry*, vol. 268:26, pp. 19604–19609.

Wojtasek et al., 1996, "An Insect Juvenile Hormone—Specific Epoxide Hydrolase Is Related to Vertebrate Microsomal Epoxide Hydrolases," *Biochemical and Biophysical Research Communications* vol. 220, pp. 323–329.

Debernard et al., 1998, "Expression and Characterization of the Recombinant Juvenile Hormone Epoxide Hydrolase (JHEH) From *Manduca sexta*," Insect Biochemistry and Molecular Biology, vol. 28, pp. 409–419.

Jacobson, et al., 1972, *Insect Juvenile Hormones; Chemistry and Action*, Academic Pres (Menn J J and Beroza M, Eds.), New York, pp. 249–302.

Takigawa, et al., Jul. 1979, *Agricultural and Biological Chemistry*, vol. 43, No. 7, pp. 1591–1594.

*Primary Examiner*—Rebecca E. Prouty
*Assistant Examiner*—Elizabeth Slobodyansky
*Attorney, Agent, or Firm*—Heska Corporation

[57] ABSTRACT

The present invention relates to arthropod epoxide hydrolase proteins; to arthropod epoxide hydrolase nucleic acid molecules, including those that encode such epoxide hydrolase proteins; to antibodies raised against such epoxide hydrolase proteins; and to other compounds that inhibit arthropod epoxide hydrolase activity. The present invention also includes methods to obtain such proteins, nucleic acid molecules, antibodies, and inhibitory compounds. Also included in the present invention are therapeutic compositions comprising such proteins, nucleic acid molecules, antibodies and/or inhibitory compounds as well as the use of such therapeutic compositions to protect animals from hematophagous arthropod infestation.

13 Claims, 6 Drawing Sheets

1. Unfed supernatant
2. Unfed pellet in TBS
3. Unfed pellet in TBS + Triton
4. Cat blood fed supernatant
5. Cat blood fed pellet in TBS
6. Cat blood fed pellet in TBS + Triton
7. PB fed supernatant
8. PB fed pellet in TBS
9. PB fed pellet in TBS + Triton

SEQUENCE LISTING

<160> NUMBER OF SEQ ID NOS: 35

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic Primer

<400> SEQUENCE: 1
aattaaccct cactaaaggg                    20

<210> SEQ ID NO 2
<211> LENGTH: 20
<212> TYPE: DNA
<213> ORGANISM: Artificial Sequence

```
<220> FEATURE:
<223> OTHER INFORMATION: Description of Artificial Sequence:   Synthetic
      Primer

<400> SEQUENCE: 2
ggcttvgwrg cttgkatrtg                                                    20

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence:   Synthetic
      Primer

<400> SEQUENCE: 3
cargsbggbg aytgggg                                                       17

<210> SEQ ID NO 4
<211> LENGTH: 211
<212> TYPE: DNA
<213> ORGANISM: Ctenocephalides felis
<220> FEATURE:
<221> NAME/KEY: CDS
<222> LOCATION: (2)..(211)

<400> SEQUENCE: 4 t cct atg atc ata agc gcg atg tca aca tta ttt cca gaa aat gtc ctg        49
  Pro Met Ile Ile Ser Ala Met Ser Thr Leu Phe Pro Glu Asn Val Leu
    1               5                  10                  15
gga cag cac tca aac atg tgt ttt gtc aat act cca tca tca aat atc          97
Gly Gln His Ser Asn Met Cys Phe Val Asn Thr Pro Ser Ser Asn Ile
             20                  25                  30
aag gct ata att gga agc ttt ttc ccg gaa tcg ttt gct ggc acg gga         145
Lys Ala Ile Ile Gly Ser Phe Phe Pro Glu Ser Phe Ala Gly Thr Gly
         35                  40                  45
aat gcg cat aaa atg tat ccc atg agt gaa cac ttt ttc aca ctt ttg         193
Asn Ala His Lys Met Tyr Pro Met Ser Glu His Phe Phe Thr Leu Leu
     50                  55                  60
gaa gaa atg ggt tat ttg                                                 211
Glu Glu Met Gly Tyr Leu
 65                  70

<210> SEQ ID NO 5
<211> LENGTH: 70
<212> TYPE: PRT
<213> ORGANISM: Ctenocephalides felis

<400> SEQUENCE: 5

Pro Met Ile Ile Ser Ala Met Ser Thr Leu Phe Pro Glu Asn Val Leu
  1               5                  10                  15

Gly Gln His Ser Asn Met Cys Phe Val Asn Thr Pro Ser Ser Asn Ile
             20                  25                  30

Lys Ala Ile Ile Gly Ser Phe Phe Pro Glu Ser Phe Ala Gly Thr Gly
         35                  40                  45

Asn Ala His Lys Met Tyr Pro Met Ser Glu His Phe Phe Thr Leu Leu
     50                  55                  60

Glu Glu Met Gly Tyr Leu
 65                  70

<210> SEQ ID NO 6
<211> LENGTH: 211
<212> TYPE: DNA
<213> ORGANISM: Ctenocephalides felis

<400> SEQUENCE: 6
```

```
caaataaccc atttcttcca aaagtgtgaa aaagtgttca ctcatgggat acattttatg      60
cgcatttccc gtgccagcaa acgattccgg gaaaaagctt ccaattatag ccttgatatt     120
tgatgatgga gtattgacaa acacatgtt tgagtgctgt cccaggacat tttctggaaa      180
taatgttgac atcgcgctta tgatcatagg a                                    211

<210> SEQ ID NO 7
<211> LENGTH: 1605
<212> TYPE: DNA
<213> ORGANISM: Ctenocephalides felis
<220> FEATURE:
<221> NAME/KEY: CDS
<222> LOCATION: (87)..(1478)

<400> SEQUENCE: 7 ttcagttta ttatgtctac aatctttgtg ttaatccgtt gtggttttaa taatatttaa       60
ttaaatttga taaataatac agaaaa atg ggt aaa tgt tgt cgt atg ctc att      113
                              Met Gly Lys Cys Cys Arg Met Leu Ile
                                1               5 ttt gct gca ata gct ggt ata gca gtg ttg tat tac caa att acg aaa       161
Phe Ala Ala Ile Ala Gly Ile Ala Val Leu Tyr Tyr Gln Ile Thr Lys
 10              15                  20                  25 gaa ctt cca aaa cca aat ata cct ctc gac act tgg tgg ggt cca gga       209
Glu Leu Pro Lys Pro Asn Ile Pro Leu Asp Thr Trp Trp Gly Pro Gly
                 30                  35                  40 aag cca caa aat gtt gac ata tca ata aga ccg ttt aaa att aat att       257
Lys Pro Gln Asn Val Asp Ile Ser Ile Arg Pro Phe Lys Ile Asn Ile
             45                  50                  55 aat aac aaa gtg att gaa aat ctg aaa cta aaa ctc aat gat gtt caa       305
Asn Asn Lys Val Ile Glu Asn Leu Lys Leu Lys Leu Asn Asp Val Gln
         60                  65                  70 tat act tta cct tta gag ggc atc aat ttt gaa tat ggt ttc aat aca       353
Tyr Thr Leu Pro Leu Glu Gly Ile Asn Phe Glu Tyr Gly Phe Asn Thr
     75                  80                  85 gat tcc ctg aaa aag att gta gat ttt tgg cga act caa tat aat tgg       401
Asp Ser Leu Lys Lys Ile Val Asp Phe Trp Arg Thr Gln Tyr Asn Trp
 90                  95                 100                 105 cgt gaa cgt gaa gca tta tta aat aaa tat cca cac ttc aaa aca aat       449
Arg Glu Arg Glu Ala Leu Leu Asn Lys Tyr Pro His Phe Lys Thr Asn
                110                 115                 120 att caa ggc ctg gat att cat tat gtc cac ata aaa cca cag gtc tct       497
Ile Gln Gly Leu Asp Ile His Tyr Val His Ile Lys Pro Gln Val Ser
            125                 130                 135 aaa aat att gaa gtt ttg cct ttg gta atg atc cat ggt tgg cca gga       545
Lys Asn Ile Glu Val Leu Pro Leu Val Met Ile His Gly Trp Pro Gly
        140                 145                 150 tct ttt gtg gaa ttc tac aag atc ata cct atg ttg aca act cca aga       593
Ser Phe Val Glu Phe Tyr Lys Ile Ile Pro Met Leu Thr Thr Pro Arg
    155                 160                 165 gca ggt tac aat ttc gta ttc gaa ttg ata ttg cct agt att cct gga       641
Ala Gly Tyr Asn Phe Val Phe Glu Leu Ile Leu Pro Ser Ile Pro Gly
170                 175                 180                 185 tac ggc ttt tca cag gct gca gct aaa cct ggt ctt gga tcg act cag       689
Tyr Gly Phe Ser Gln Ala Ala Ala Lys Pro Gly Leu Gly Ser Thr Gln
                190                 195                 200 gtc gcc gtt ata atg cgc aat ttg atg gag cgc att gga ttc aaa aaa       737
Val Ala Val Ile Met Arg Asn Leu Met Glu Arg Ile Gly Phe Lys Lys
            205                 210                 215 tat tat gta caa gga ggc gac tgg ggt tct atg atc ata agc gcg atg       785
Tyr Tyr Val Gln Gly Gly Asp Trp Gly Ser Met Ile Ile Ser Ala Met
```

-continued

```
             220                 225                 230
tca aca tta ttt cca gaa aat gtc ctg gga cag cac tca aac atg tgt      833
Ser Thr Leu Phe Pro Glu Asn Val Leu Gly Gln His Ser Asn Met Cys
        235                 240                 245 ttt gtc aat act cca tca tca aat atc aag gct ata att gga agc ttt      881
Phe Val Asn Thr Pro Ser Ser Asn Ile Lys Ala Ile Ile Gly Ser Phe
250                 255                 260                 265 ttc ccg gaa tcg ttt gct ggc acg gga aat gcg cat aaa atg tat ccc      929
Phe Pro Glu Ser Phe Ala Gly Thr Gly Asn Ala His Lys Met Tyr Pro
                270                 275                 280 atg agt gaa cac ttt ttc aca ctt ttg gaa gaa atg ggt tat ttg cat      977
Met Ser Glu His Phe Phe Thr Leu Leu Glu Glu Met Gly Tyr Leu His
            285                 290                 295 cta caa gct acc aaa cca gat aca gtg ggc gtt gct tta aga gat tca     1025
Leu Gln Ala Thr Lys Pro Asp Thr Val Gly Val Ala Leu Arg Asp Ser
        300                 305                 310 cca gct ggt tta gca gct tat att ttg gag aaa ttt tca aca tgg act     1073
Pro Ala Gly Leu Ala Ala Tyr Ile Leu Glu Lys Phe Ser Thr Trp Thr
315                 320                 325 aac aga tct tgg agg tca gtt aaa gat gga aac ttg ctg tta aaa tac     1121
Asn Arg Ser Trp Arg Ser Val Lys Asp Gly Asn Leu Leu Leu Lys Tyr
330                 335                 340                 345 aat att cct gaa ctt tta gac aat gtc atg ata tac tac gtt act gat     1169
Asn Ile Pro Glu Leu Leu Asp Asn Val Met Ile Tyr Tyr Val Thr Asp
                350                 355                 360 tcc att act act tca atg aga tta tat gca gaa tca ttc aca aaa gca     1217
Ser Ile Thr Thr Ser Met Arg Leu Tyr Ala Glu Ser Phe Thr Lys Ala
            365                 370                 375 cac ctt gct ttg aac tta gat agg gtg cgc aat cat gtc cca gca gcc     1265
His Leu Ala Leu Asn Leu Asp Arg Val Arg Asn His Val Pro Ala Ala
        380                 385                 390 tgc gca aaa ttt cca aac gag ttg gct tat gtg acc gat tgc caa ctt     1313
Cys Ala Lys Phe Pro Asn Glu Leu Ala Tyr Val Thr Asp Cys Gln Leu
        395                 400                 405 gct gag aaa tat aaa act tta ttg cag tcc aat gac atg cca agt ggt     1361
Ala Glu Lys Tyr Lys Thr Leu Leu Gln Ser Asn Asp Met Pro Ser Gly
410                 415                 420                 425 ggc cat ttt gca gca ttt gag gaa cct ggt ctt tta gca gaa gac att     1409
Gly His Phe Ala Ala Phe Glu Glu Pro Gly Leu Leu Ala Glu Asp Ile
                430                 435                 440 ttc act gcg gtg aaa aag ttt aaa gaa ttt tat tcc aaa aaa gct gaa     1457
Phe Thr Ala Val Lys Lys Phe Lys Glu Phe Tyr Ser Lys Lys Ala Glu
            445                 450                 455 agc caa aag aaa gct gat ttg tgataattt gttgttgata tattattatg        1508
Ser Gln Lys Lys Ala Asp Leu
        460 ctaataatat ttgagataaa tttaaccaat tcatgttcaa catatatttt tatacataca   1568 tacatatata taaataataa aaaaaaaaaa aaaaaaa                            1605

<210> SEQ ID NO 8
<211> LENGTH: 464
<212> TYPE: PRT
<213> ORGANISM: Ctenocephalides felis

<400> SEQUENCE: 8

Met Gly Lys Cys Cys Arg Met Leu Ile Phe Ala Ala Ile Ala Gly Ile
1               5                   10                  15

Ala Val Leu Tyr Tyr Gln Ile Thr Lys Glu Leu Pro Lys Pro Asn Ile
            20                  25                  30
```

```
Pro Leu Asp Thr Trp Trp Gly Pro Gly Lys Pro Gln Asn Val Asp Ile
         35                  40                  45

Ser Ile Arg Pro Phe Lys Ile Asn Ile Asn Asn Lys Val Ile Glu Asn
     50                  55                  60

Leu Lys Leu Lys Leu Asn Asp Val Gln Tyr Thr Leu Pro Leu Glu Gly
 65                  70                  75                  80

Ile Asn Phe Glu Tyr Gly Phe Asn Thr Asp Ser Leu Lys Lys Ile Val
                 85                  90                  95

Asp Phe Trp Arg Thr Gln Tyr Asn Trp Arg Glu Arg Glu Ala Leu Leu
             100                 105                 110

Asn Lys Tyr Pro His Phe Lys Thr Asn Ile Gln Gly Leu Asp Ile His
             115                 120                 125

Tyr Val His Ile Lys Pro Gln Val Ser Lys Asn Ile Glu Val Leu Pro
130                 135                 140

Leu Val Met Ile His Gly Trp Pro Gly Ser Phe Val Glu Phe Tyr Lys
145                 150                 155                 160

Ile Ile Pro Met Leu Thr Thr Pro Arg Ala Gly Tyr Asn Phe Val Phe
                 165                 170                 175

Glu Leu Ile Leu Pro Ser Ile Pro Gly Tyr Gly Phe Ser Gln Ala Ala
             180                 185                 190

Ala Lys Pro Gly Leu Gly Ser Thr Gln Val Ala Val Ile Met Arg Asn
             195                 200                 205

Leu Met Glu Arg Ile Gly Phe Lys Lys Tyr Tyr Val Gln Gly Gly Asp
             210                 215                 220

Trp Gly Ser Met Ile Ile Ser Ala Met Ser Thr Leu Phe Pro Glu Asn
225                 230                 235                 240

Val Leu Gly Gln His Ser Asn Met Cys Phe Val Asn Thr Pro Ser Ser
                 245                 250                 255

Asn Ile Lys Ala Ile Ile Gly Ser Phe Phe Pro Glu Ser Phe Ala Gly
             260                 265                 270

Thr Gly Asn Ala His Lys Met Tyr Pro Met Ser Glu His Phe Phe Thr
             275                 280                 285

Leu Leu Glu Glu Met Gly Tyr Leu His Leu Gln Ala Thr Lys Pro Asp
290                 295                 300

Thr Val Gly Val Ala Leu Arg Asp Ser Pro Ala Gly Leu Ala Ala Tyr
305                 310                 315                 320

Ile Leu Glu Lys Phe Ser Thr Trp Thr Asn Arg Ser Trp Arg Ser Val
             325                 330                 335

Lys Asp Gly Asn Leu Leu Leu Lys Tyr Asn Ile Pro Glu Leu Leu Asp
             340                 345                 350

Asn Val Met Ile Tyr Tyr Val Thr Asp Ser Ile Thr Thr Ser Met Arg
             355                 360                 365

Leu Tyr Ala Glu Ser Phe Thr Lys Ala His Leu Ala Leu Asn Leu Asp
         370                 375                 380

Arg Val Arg Asn His Val Pro Ala Ala Cys Ala Lys Phe Pro Asn Glu
385                 390                 395                 400

Leu Ala Tyr Val Thr Asp Cys Gln Leu Ala Glu Lys Tyr Lys Thr Leu
                 405                 410                 415

Leu Gln Ser Asn Asp Met Pro Ser Gly Gly His Phe Ala Ala Phe Glu
             420                 425                 430

Glu Pro Gly Leu Leu Ala Glu Asp Ile Phe Thr Ala Val Lys Lys Phe
             435                 440                 445
```

Lys Glu Phe Tyr Ser Lys Lys Ala Glu Ser Gln Lys Lys Ala Asp Leu
    450                 455                 460

<210> SEQ ID NO 9
<211> LENGTH: 1605
<212> TYPE: DNA
<213> ORGANISM: Ctenocephalides felis

<400> SEQUENCE: 9

| | | | | | |
|---|---|---|---|---|---|
| tttttttttt | tttttttta | ttatttatat | atatgtatgt | atgtataaaa | atatatgttg | 60 |
| aacatgaatt | ggttaaattt | atctcaaata | ttattagcat | aataatatat | caacaacaaa | 120 |
| attatcacaa | atcagctttc | ttttggcttt | cagctttttt | ggaataaaat | tctttaaact | 180 |
| ttttcaccgc | agtgaaaatg | tcttctgcta | aagaccagg | ttcctcaaat | gctgcaaaat | 240 |
| ggccaccact | tggcatgtca | ttggactgca | ataagtttt | atatttctca | gcaagttggc | 300 |
| aatcggtcac | ataagccaac | tcgtttgaa | attttgcgca | ggctgctggg | acatgattgc | 360 |
| gcaccctatc | taagttcaaa | gcaaggtgtg | cttttgtgaa | tgattctgca | tataatctca | 420 |
| ttgaagtagt | aatggaatca | gtaacgtagt | atatcatgac | attgtctaaa | agttcaggaa | 480 |
| tattgtattt | taacagcaag | tttccatctt | taactgacct | ccaagatctg | ttagtccatg | 540 |
| ttgaaaattt | ctccaaaata | taagctgcta | aaccagctgg | tgaatctctt | aaagcaacgc | 600 |
| ccactgtatc | tggtttggta | gcttgtagat | gcaaataacc | catttcttcc | aaaagtgtga | 660 |
| aaagtgttc | actcatggga | tacattttat | gcgcatttcc | cgtgccagca | aacgattccg | 720 |
| ggaaaaagct | tccaattata | gccttgatat | ttgatgatgg | agtattgaca | aaacacatgt | 780 |
| ttgagtgctg | tcccaggaca | ttttctggaa | ataatgttga | catcgcgctt | atgatcatag | 840 |
| aaccccagtc | gcctccttgt | acataatatt | ttttgaatcc | aatgcgctcc | atcaaattgc | 900 |
| gcattataac | ggcgacctga | gtcgatccaa | gaccaggttt | agctgcagcc | tgtgaaaagc | 960 |
| cgtatccagg | aatactaggc | aatatcaatt | cgaatacgaa | attgtaacct | gctcttggag | 1020 |
| ttgtcaacat | aggtatgatc | ttgtagaatt | ccacaaaaga | tcctggccaa | ccatggatca | 1080 |
| ttaccaaagg | caaaacttca | atattttag | agacctgtgg | ttttatgtgg | acataatgaa | 1140 |
| tatccaggcc | ttgaatattt | gttttgaagt | gtggatattt | atttaataat | gcttcacgtt | 1200 |
| cacgccaatt | atattgagtt | cgccaaaaat | ctacaatctt | tttcagggaa | tctgtattga | 1260 |
| aaccatattc | aaaattgatg | ccctctaaag | gtaaagtata | ttgaacatca | ttgagtttta | 1320 |
| gtttcagatt | ttcaatcact | ttgttattaa | tattaattt | aaacggtctt | attgatatgt | 1380 |
| caacattttg | tggctttcct | ggaccccacc | aagtgtcgag | aggtatattt | ggttttggaa | 1440 |
| gttctttcgt | aatttggtaa | tacaacactg | ctataccagc | tattgcagca | aaaatgagca | 1500 |
| tacgacaaca | tttacccatt | tttctgtatt | atttatcaaa | tttaattaaa | tattattaaa | 1560 |
| accacaacgg | attaacacaa | agattgtaga | cataataaaa | ctgaa | | 1605 |

<210> SEQ ID NO 10
<211> LENGTH: 1392
<212> TYPE: DNA
<213> ORGANISM: Ctenocephalides felis
<220> FEATURE:
<221> NAME/KEY: CDS
<222> LOCATION: (1)..(1392)

<400> SEQUENCE: 10 atg ggt aaa tgt tgt cgt atg ctc att ttt gct gca ata gct ggt ata    48
Met Gly Lys Cys Cys Arg Met Leu Ile Phe Ala Ala Ile Ala Gly Ile
  1               5                  10                  15

-continued

```
gca gtg ttg tat tac caa att acg aaa gaa ctt cca aaa cca aat ata      96
Ala Val Leu Tyr Tyr Gln Ile Thr Lys Glu Leu Pro Lys Pro Asn Ile
             20                  25                  30 cct ctc gac act tgg tgg ggt cca gga aag cca caa aat gtt gac ata     144
Pro Leu Asp Thr Trp Trp Gly Pro Gly Lys Pro Gln Asn Val Asp Ile
         35                  40                  45 tca ata aga ccg ttt aaa att aat att aat aac aaa gtg att gaa aat     192
Ser Ile Arg Pro Phe Lys Ile Asn Ile Asn Asn Lys Val Ile Glu Asn
     50                  55                  60 ctg aaa cta aaa ctc aat gat gtt caa tat act tta cct tta gag ggc     240
Leu Lys Leu Lys Leu Asn Asp Val Gln Tyr Thr Leu Pro Leu Glu Gly
 65                  70                  75                  80 atc aat ttt gaa tat ggt ttc aat aca gat tcc ctg aaa aag att gta     288
Ile Asn Phe Glu Tyr Gly Phe Asn Thr Asp Ser Leu Lys Lys Ile Val
                 85                  90                  95 gat ttt tgg cga act caa tat aat tgg cgt gaa cgt gaa gca tta tta     336
Asp Phe Trp Arg Thr Gln Tyr Asn Trp Arg Glu Arg Glu Ala Leu Leu
            100                 105                 110 aat aaa tat cca cac ttc aaa aca aat att caa ggc ctg gat att cat     384
Asn Lys Tyr Pro His Phe Lys Thr Asn Ile Gln Gly Leu Asp Ile His
        115                 120                 125 tat gtc cac ata aaa cca cag gtc tct aaa aat att gaa gtt ttg cct     432
Tyr Val His Ile Lys Pro Gln Val Ser Lys Asn Ile Glu Val Leu Pro
    130                 135                 140 ttg gta atg atc cat ggt tgg cca gga tct ttt gtg gaa ttc tac aag     480
Leu Val Met Ile His Gly Trp Pro Gly Ser Phe Val Glu Phe Tyr Lys
145                 150                 155                 160 atc ata cct atg ttg aca act cca aga gca ggt tac aat ttc gta ttc     528
Ile Ile Pro Met Leu Thr Thr Pro Arg Ala Gly Tyr Asn Phe Val Phe
                165                 170                 175 gaa ttg ata ttg cct agt att cct gga tac ggc ttt tca cag gct gca     576
Glu Leu Ile Leu Pro Ser Ile Pro Gly Tyr Gly Phe Ser Gln Ala Ala
            180                 185                 190 gct aaa cct ggt ctt gga tcg act cag gtc gcc gtt ata atg cgc aat     624
Ala Lys Pro Gly Leu Gly Ser Thr Gln Val Ala Val Ile Met Arg Asn
        195                 200                 205 ttg atg gag cgc att gga ttc aaa aaa tat tat gta caa gga ggc gac     672
Leu Met Glu Arg Ile Gly Phe Lys Lys Tyr Tyr Val Gln Gly Gly Asp
    210                 215                 220 tgg ggt tct atg atc ata agc gcg atg tca aca tta ttt cca gaa aat     720
Trp Gly Ser Met Ile Ile Ser Ala Met Ser Thr Leu Phe Pro Glu Asn
225                 230                 235                 240 gtc ctg gga cag cac tca aac atg tgt ttt gtc aat act cca tca tca     768
Val Leu Gly Gln His Ser Asn Met Cys Phe Val Asn Thr Pro Ser Ser
                245                 250                 255 aat atc aag gct ata att gga agc ttt ttc ccg gaa tcg ttt gct ggc     816
Asn Ile Lys Ala Ile Ile Gly Ser Phe Phe Pro Glu Ser Phe Ala Gly
            260                 265                 270 acg gga aat gcg cat aaa atg tat ccc atg agt gaa cac ttt ttc aca     864
Thr Gly Asn Ala His Lys Met Tyr Pro Met Ser Glu His Phe Phe Thr
        275                 280                 285 ctt ttg gaa gaa atg ggt tat ttg cat cta caa gct acc aaa cca gat     912
Leu Leu Glu Glu Met Gly Tyr Leu His Leu Gln Ala Thr Lys Pro Asp
    290                 295                 300 aca gtg ggc gtt gct tta aga gat tca cca gct ggt tta gca gct tat     960
Thr Val Gly Val Ala Leu Arg Asp Ser Pro Ala Gly Leu Ala Ala Tyr
305                 310                 315                 320 att ttg gag aaa ttt tca aca tgg act aac aga tct tgg agg tca gtt    1008
Ile Leu Glu Lys Phe Ser Thr Trp Thr Asn Arg Ser Trp Arg Ser Val
```

```
                 325                 330                 335
aaa gat gga aac ttg ctg tta aaa tac aat att cct gaa ctt tta gac    1056
Lys Asp Gly Asn Leu Leu Leu Lys Tyr Asn Ile Pro Glu Leu Leu Asp
            340                 345                 350 aat gtc atg ata tac tac gtt act gat tcc att act act tca atg aga    1104
Asn Val Met Ile Tyr Tyr Val Thr Asp Ser Ile Thr Thr Ser Met Arg
        355                 360                 365 tta tat gca gaa tca ttc aca aaa gca cac ctt gct ttg aac tta gat    1152
Leu Tyr Ala Glu Ser Phe Thr Lys Ala His Leu Ala Leu Asn Leu Asp
    370                 375                 380 agg gtg cgc aat cat gtc cca gca gcc tgc gca aaa ttt cca aac gag    1200
Arg Val Arg Asn His Val Pro Ala Ala Cys Ala Lys Phe Pro Asn Glu
385                 390                 395                 400 ttg gct tat gtg acc gat tgc caa ctt gct gag aaa tat aaa act tta    1248
Leu Ala Tyr Val Thr Asp Cys Gln Leu Ala Glu Lys Tyr Lys Thr Leu
                405                 410                 415 ttg cag tcc aat gac atg cca agt ggt ggc cat ttt gca gca ttt gag    1296
Leu Gln Ser Asn Asp Met Pro Ser Gly Gly His Phe Ala Ala Phe Glu
            420                 425                 430 gaa cct ggt ctt tta gca gaa gac att ttc act gcg gtg aaa aag ttt    1344
Glu Pro Gly Leu Leu Ala Glu Asp Ile Phe Thr Ala Val Lys Lys Phe
        435                 440                 445 aaa gaa ttt tat tcc aaa aaa gct gaa agc caa aag aaa gct gat ttg    1392
Lys Glu Phe Tyr Ser Lys Lys Ala Glu Ser Gln Lys Lys Ala Asp Leu
    450                 455                 460

<210> SEQ ID NO 11
<211> LENGTH: 464
<212> TYPE: PRT
<213> ORGANISM: Ctenocephalides felis

<400> SEQUENCE: 11

Met Gly Lys Cys Cys Arg Met Leu Ile Phe Ala Ala Ile Ala Gly Ile
 1               5                  10                  15

Ala Val Leu Tyr Tyr Gln Ile Thr Lys Glu Leu Pro Lys Pro Asn Ile
            20                  25                  30

Pro Leu Asp Thr Trp Trp Gly Pro Gly Lys Pro Gln Asn Val Asp Ile
        35                  40                  45

Ser Ile Arg Pro Phe Lys Ile Asn Ile Asn Asn Lys Val Ile Glu Asn
    50                  55                  60

Leu Lys Leu Lys Leu Asn Asp Val Gln Tyr Thr Leu Pro Leu Glu Gly
65                  70                  75                  80

Ile Asn Phe Glu Tyr Gly Phe Asn Thr Asp Ser Leu Lys Lys Ile Val
                85                  90                  95

Asp Phe Trp Arg Thr Gln Tyr Asn Trp Arg Glu Arg Glu Ala Leu Leu
            100                 105                 110

Asn Lys Tyr Pro His Phe Lys Thr Asn Ile Gln Gly Leu Asp Ile His
        115                 120                 125

Tyr Val His Ile Lys Pro Gln Val Ser Lys Asn Ile Glu Val Leu Pro
    130                 135                 140

Leu Val Met Ile His Gly Trp Pro Gly Ser Phe Val Glu Phe Tyr Lys
145                 150                 155                 160

Ile Ile Pro Met Leu Thr Thr Pro Arg Ala Gly Tyr Asn Phe Val Phe
                165                 170                 175

Glu Leu Ile Leu Pro Ser Ile Pro Gly Tyr Gly Phe Ser Gln Ala Ala
            180                 185                 190

Ala Lys Pro Gly Leu Gly Ser Thr Gln Val Ala Val Ile Met Arg Asn
```

-continued

| | 195 | | | | 200 | | | | 205 | | | |
|---|---|---|---|---|---|---|---|---|---|---|---|---|
| Leu | Met | Glu | Arg | Ile | Gly | Phe | Lys | Lys | Tyr | Tyr | Val | Gln | Gly | Gly | Asp |
| | 210 | | | | | 215 | | | | 220 | | | |

Trp Gly Ser Met Ile Ile Ser Ala Met Ser Thr Leu Phe Pro Glu Asn
225                 230                 235                 240

Val Leu Gly Gln His Ser Asn Met Cys Phe Val Asn Thr Pro Ser Ser
            245                 250                 255

Asn Ile Lys Ala Ile Ile Gly Ser Phe Phe Pro Glu Ser Phe Ala Gly
        260                 265                 270

Thr Gly Asn Ala His Lys Met Tyr Pro Met Ser Glu His Phe Phe Thr
    275                 280                 285

Leu Leu Glu Glu Met Gly Tyr Leu His Leu Gln Ala Thr Lys Pro Asp
290                 295                 300

Thr Val Gly Val Ala Leu Arg Asp Ser Pro Ala Gly Leu Ala Ala Tyr
305                 310                 315                 320

Ile Leu Glu Lys Phe Ser Thr Trp Thr Asn Arg Ser Trp Arg Ser Val
            325                 330                 335

Lys Asp Gly Asn Leu Leu Leu Lys Tyr Asn Ile Pro Glu Leu Leu Asp
        340                 345                 350

Asn Val Met Ile Tyr Tyr Val Thr Asp Ser Ile Thr Thr Ser Met Arg
    355                 360                 365

Leu Tyr Ala Glu Ser Phe Thr Lys Ala His Leu Ala Leu Asn Leu Asp
370                 375                 380

Arg Val Arg Asn His Val Pro Ala Ala Cys Ala Lys Phe Pro Asn Glu
385                 390                 395                 400

Leu Ala Tyr Val Thr Asp Cys Gln Leu Ala Glu Lys Tyr Lys Thr Leu
            405                 410                 415

Leu Gln Ser Asn Asp Met Pro Ser Gly Gly His Phe Ala Ala Phe Glu
        420                 425                 430

Glu Pro Gly Leu Leu Ala Glu Asp Ile Phe Thr Ala Val Lys Lys Phe
    435                 440                 445

Lys Glu Phe Tyr Ser Lys Lys Ala Glu Ser Gln Lys Lys Ala Asp Leu
450                 455                 460

```
<210> SEQ ID NO 12
<211> LENGTH: 1392
<212> TYPE: DNA
<213> ORGANISM: Ctenocephalides felis

<400> SEQUENCE: 12
caaatcagct ttcttttggc tttcagcttt tttggaataa aattctttaa acttttcac      60 cgcagtgaaa atgtcttctg ctaaaagacc aggttcctca aatgctgcaa atggccacc    120 acttggcatg tcattggact gcaataaagt tttatatttc tcagcaagtt ggcaatcgt    180 cacataagcc aactcgtttg gaaattttgc gcaggctgct gggacatgat tgcgcaccct   240
atctaagttc aaagcaaggt gtgcttttgt gaatgattct gcatataatc tcattgaagt   300
agtaatggaa tcagtaacgt agtatatcat gacattgtct aaaagttcag gaatattgta   360
ttttaacagc aagtttccat ctttaactga cctccaagat ctgttagtcc atgttgaaaa   420
tttctccaaa atataagctg ctaaaccagc tggtgaatct cttaaagcaa cgcccactgt   480
atctggtttg gtagcttgta gatgcaaata acccatttct tccaaaagtg tgaaaaagtg   540
ttcactcatg ggatacattt tatgcgcatt tcccgtgcca gcaaacgatt ccgggaaaaa   600
gcttccaatt atagccttga tatttgatga tggagtattg acaaaacaca tgtttgagtg   660
```

```
ctgtcccagg acattttctg gaaataatgt tgacatcgcg cttatgatca tagaaccccca    720 gtcgcctcct tgtacataat attttttgaa tccaatgcgc tccatcaaat tgcgcattat    780
aacggcgacc tgagtcgatc caagaccagg tttagctgca gcctgtgaaa agccgtatcc    840
aggaatacta ggcaatatca attcgaatac gaaattgtaa cctgctcttg gagttgtcaa    900
cataggtatg atcttgtaga attccacaaa agatcctggc caaccatgga tcattaccaa    960
aggcaaaact tcaatatttt tagagacctg tggttttatg tggacataat gaatatccag   1020
gccttgaata tttgttttga agtgtggata tttatttaat aatgcttcac gttcacgcca   1080
attatattga gttcgccaaa aatctacaat cttttttcagg gaatctgtat tgaaaccata   1140
ttcaaaattg atgccctcta aagtaaagt atattgaaca tcattgagtt ttagtttcag    1200
attttcaatc actttgttat taatattaat tttaaacggt cttattgata tgtcaacatt   1260
ttgtggcttt cctggacccc accaagtgtc gagaggtata tttggttttg gaagttcttt   1320
cgtaatttgg taatacaaca ctgctatacc agctattgca gcaaaaatga gcatacgaca   1380
acatttaccc at                                                        1392
```

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13

```
gtaggatccg attacgaaag aacttccaaa acc                                    33
```

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14

```
aacactcgag tcacaaatca gctttctttt gg                                     32
```

<210> SEQ ID NO 15
<211> LENGTH: 1284
<212> TYPE: DNA
<213> ORGANISM: Ctenocephalides felis
<220> FEATURE:
<221> NAME/KEY: CDS
<222> LOCATION: (2)..(1282)

<400> SEQUENCE: 15

```
a aat ata cct ctc gac act tgg tgg ggt cca gga aag cca caa aat gtt    49
  Asn Ile Pro Leu Asp Thr Trp Trp Gly Pro Gly Lys Pro Gln Asn Val
   1               5                  10                  15 gac ata tca ata aga ccg ttt aaa att aat att aat aac aaa gtg att    97
Asp Ile Ser Ile Arg Pro Phe Lys Ile Asn Ile Asn Asn Lys Val Ile
             20                  25                  30 gaa aat ctg aaa cta aaa ctc aat gat gtt caa tat act tta cct tta   145
Glu Asn Leu Lys Leu Lys Leu Asn Asp Val Gln Tyr Thr Leu Pro Leu
         35                  40                  45 gag ggc atc aat ttt gaa tat ggt ttc aat aca gat tcc ctg aaa aag   193
Glu Gly Ile Asn Phe Glu Tyr Gly Phe Asn Thr Asp Ser Leu Lys Lys
 50                  55                  60
```

-continued

| | | |
|---|---|---|
| att gta gat ttt tgg cga act caa tat aat tgg cgt gaa cgt gaa gca<br>Ile Val Asp Phe Trp Arg Thr Gln Tyr Asn Trp Arg Glu Arg Glu Ala<br>65                          70                    75                  80 | | 241 |
| tta tta aat aaa tat cca cac ttc aaa aca aat att caa ggc ctg gat<br>Leu Leu Asn Lys Tyr Pro His Phe Lys Thr Asn Ile Gln Gly Leu Asp<br>                    85                    90                  95 | | 289 |
| att cat tat gtc cac ata aaa cca cag gtc tct aaa aat att gaa gtt<br>Ile His Tyr Val His Ile Lys Pro Gln Val Ser Lys Asn Ile Glu Val<br>                100                   105               110 | | 337 |
| ttg cct ttg gta atg atc cat ggt tgg cca gga tct ttt gtg gaa ttc<br>Leu Pro Leu Val Met Ile His Gly Trp Pro Gly Ser Phe Val Glu Phe<br>           115                   120               125 | | 385 |
| tac aag atc ata cct atg ttg aca act cca aga gca ggt tac aat ttc<br>Tyr Lys Ile Ile Pro Met Leu Thr Thr Pro Arg Ala Gly Tyr Asn Phe<br>130                    135                   140 | | 433 |
| gta ttc gaa ttg ata ttg cct agt att cct gga tac ggc ttt tca cag<br>Val Phe Glu Leu Ile Leu Pro Ser Ile Pro Gly Tyr Gly Phe Ser Gln<br>145                    150                   155               160 | | 481 |
| gct gca gct aaa cct ggt ctt gga tcg act cag gtc gcc gtt ata atg<br>Ala Ala Ala Lys Pro Gly Leu Gly Ser Thr Gln Val Ala Val Ile Met<br>                165                   170               175 | | 529 |
| cgc aat ttg atg gag cgc att gga ttc aaa aaa tat tat gta caa gga<br>Arg Asn Leu Met Glu Arg Ile Gly Phe Lys Lys Tyr Tyr Val Gln Gly<br>                    180                   185               190 | | 577 |
| ggc gac tgg ggt tct atg atc ata agc gcg atg tca aca tta ttt cca<br>Gly Asp Trp Gly Ser Met Ile Ile Ser Ala Met Ser Thr Leu Phe Pro<br>           195                   200               205 | | 625 |
| gaa aat gtc ctg gga cag cac tca aac atg tgt ttt gtc aat act cca<br>Glu Asn Val Leu Gly Gln His Ser Asn Met Cys Phe Val Asn Thr Pro<br>210                    215                   220 | | 673 |
| tca tca aat atc aag gct ata att gga agc ttt ttc ccg gaa tcg ttt<br>Ser Ser Asn Ile Lys Ala Ile Ile Gly Ser Phe Phe Pro Glu Ser Phe<br>225                    230                   235               240 | | 721 |
| gct ggc acg gga aat gcg cat aaa atg tat ccc atg agt gaa cac ttt<br>Ala Gly Thr Gly Asn Ala His Lys Met Tyr Pro Met Ser Glu His Phe<br>                      245                   250               255 | | 769 |
| ttc aca ctt ttg gaa gaa atg ggt tat ttg cat cta caa gct acc aaa<br>Phe Thr Leu Leu Glu Glu Met Gly Tyr Leu His Leu Gln Ala Thr Lys<br>           260                   265               270 | | 817 |
| cca gat aca gtg ggc gtt gct tta aga gat tca cca gct ggt tta gca<br>Pro Asp Thr Val Gly Val Ala Leu Arg Asp Ser Pro Ala Gly Leu Ala<br>                275                   280               285 | | 865 |
| gct tat att ttg gag aaa ttt tca aca tgg act aac aga tct tgg agg<br>Ala Tyr Ile Leu Glu Lys Phe Ser Thr Trp Thr Asn Arg Ser Trp Arg<br>          290                   295               300 | | 913 |
| tca gtt aaa gat gga aac ttg ctg tta aaa tac aat att cct gaa ctt<br>Ser Val Lys Asp Gly Asn Leu Leu Leu Lys Tyr Asn Ile Pro Glu Leu<br>305                    310                   315               320 | | 961 |
| tta gac aat gtc atg ata tac tac gtt act gat tcc att act act tca<br>Leu Asp Asn Val Met Ile Tyr Tyr Val Thr Asp Ser Ile Thr Thr Ser<br>                    325                   330               335 | | 1009 |
| atg aga tta tat gca gaa tca ttc aca aaa gca cac ctt gct ttg aac<br>Met Arg Leu Tyr Ala Glu Ser Phe Thr Lys Ala His Leu Ala Leu Asn<br>          340                   345               350 | | 1057 |
| tta gat agg gtg cgc aat cat gtc cca gca gcc tgc gca aaa ttt cca<br>Leu Asp Arg Val Arg Asn His Val Pro Ala Ala Cys Ala Lys Phe Pro<br>                355                   360               365 | | 1105 |
| aac gag ttg gct tat gtg acc gat tgc caa ctt gct gag aaa tat aaa<br>Asn Glu Leu Ala Tyr Val Thr Asp Cys Gln Leu Ala Glu Lys Tyr Lys | | 1153 |

-continued

```
           370                 375                 380
act ttg ttg cag tcc aat gac atg cca agt ggt ggc cat ttt gca gca         1201
Thr Leu Leu Gln Ser Asn Asp Met Pro Ser Gly Gly His Phe Ala Ala
385                 390                 395                 400 ttt gag gaa cct ggt ctt tta gca gaa gac att ttc act gcg gtg aaa         1249
Phe Glu Glu Pro Gly Leu Leu Ala Glu Asp Ile Phe Thr Ala Val Lys
                405                 410                 415 aag ttt aaa gaa ttt tat tcc aaa aaa gct gaa ag                          1284
Lys Phe Lys Glu Phe Tyr Ser Lys Lys Ala Glu
                420                 425
```

<210> SEQ ID NO 16
<211> LENGTH: 427
<212> TYPE: PRT
<213> ORGANISM: Ctenocephalides felis

<400> SEQUENCE: 16

```
Asn Ile Pro Leu Asp Thr Trp Trp Gly Pro Gly Lys Pro Gln Asn Val
 1               5                  10                  15

Asp Ile Ser Ile Arg Pro Phe Lys Ile Asn Ile Asn Asn Lys Val Ile
                20                  25                  30

Glu Asn Leu Lys Leu Lys Leu Asn Asp Val Gln Tyr Thr Leu Pro Leu
            35                  40                  45

Glu Gly Ile Asn Phe Glu Tyr Gly Phe Asn Thr Asp Ser Leu Lys Lys
        50                  55                  60

Ile Val Asp Phe Trp Arg Thr Gln Tyr Asn Trp Arg Glu Arg Glu Ala
 65                 70                  75                  80

Leu Leu Asn Lys Tyr Pro His Phe Lys Thr Asn Ile Gln Gly Leu Asp
                85                  90                  95

Ile His Tyr Val His Ile Lys Pro Gln Val Ser Lys Asn Ile Glu Val
            100                 105                 110

Leu Pro Leu Val Met Ile His Gly Trp Pro Gly Ser Phe Val Glu Phe
        115                 120                 125

Tyr Lys Ile Ile Pro Met Leu Thr Thr Pro Arg Ala Gly Tyr Asn Phe
    130                 135                 140

Val Phe Glu Leu Ile Leu Pro Ser Ile Pro Gly Tyr Gly Phe Ser Gln
145                 150                 155                 160

Ala Ala Ala Lys Pro Gly Leu Gly Ser Thr Gln Val Ala Val Ile Met
                165                 170                 175

Arg Asn Leu Met Glu Arg Ile Gly Phe Lys Lys Tyr Tyr Val Gln Gly
            180                 185                 190

Gly Asp Trp Gly Ser Met Ile Ile Ser Ala Met Ser Thr Leu Phe Pro
        195                 200                 205

Glu Asn Val Leu Gly Gln His Ser Asn Met Cys Phe Val Asn Thr Pro
    210                 215                 220

Ser Ser Asn Ile Lys Ala Ile Ile Gly Ser Phe Phe Pro Glu Ser Phe
225                 230                 235                 240

Ala Gly Thr Gly Asn Ala His Lys Met Tyr Pro Met Ser Glu His Phe
                245                 250                 255

Phe Thr Leu Leu Glu Glu Met Gly Tyr Leu His Leu Gln Ala Thr Lys
            260                 265                 270

Pro Asp Thr Val Gly Val Ala Leu Arg Asp Ser Pro Ala Gly Leu Ala
        275                 280                 285

Ala Tyr Ile Leu Glu Lys Phe Ser Thr Trp Thr Asn Arg Ser Trp Arg
    290                 295                 300
```

```
Ser Val Lys Asp Gly Asn Leu Leu Lys Tyr Asn Ile Pro Glu Leu
305                 310                 315                 320

Leu Asp Asn Val Met Ile Tyr Tyr Val Thr Asp Ser Ile Thr Thr Ser
            325                 330                 335

Met Arg Leu Tyr Ala Glu Ser Phe Thr Lys Ala His Leu Ala Leu Asn
        340                 345                 350

Leu Asp Arg Val Arg Asn His Val Pro Ala Ala Cys Ala Lys Phe Pro
        355                 360                 365

Asn Glu Leu Ala Tyr Val Thr Asp Cys Gln Leu Ala Glu Lys Tyr Lys
        370                 375                 380

Thr Leu Leu Gln Ser Asn Asp Met Pro Ser Gly His Phe Ala Ala
385                 390                 395                 400

Phe Glu Glu Pro Gly Leu Leu Ala Glu Asp Ile Phe Thr Ala Val Lys
                405                 410                 415

Lys Phe Lys Glu Phe Tyr Ser Lys Lys Ala Glu
            420                 425

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
ccgggatcct ataaatatgg gtaaatgttg tcgtatgc                              38

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
ccgtctagat cacaaatcag ctttcttttg gc                                    32

<210> SEQ ID NO 19
<211> LENGTH: 211
<212> TYPE: DNA
<213> ORGANISM: Ctenocephalides felis
<220> FEATURE:
<221> NAME/KEY: CDS
<222> LOCATION: (2)..(211)

<400> SEQUENCE: 19 t tct aga atc gtc agc gct atg tca act ttg ttt cca gaa aat gtt ctt     49
  Ser Arg Ile Val Ser Ala Met Ser Thr Leu Phe Pro Glu Asn Val Leu
  1               5                   10                  15 gga cac cat tct aat tta tgc ttt tta aat aca cta tct tca aat ata       97
Gly His His Ser Asn Leu Cys Phe Leu Asn Thr Leu Ser Ser Asn Ile
            20                  25                  30 aag tcc ttt gtt ggc agt tta ttc cca gaa tgg ttt gct gga aaa caa       145
Lys Ser Phe Val Gly Ser Leu Phe Pro Glu Trp Phe Ala Gly Lys Gln
        35                  40                  45 aat gtt cat aaa atc tat cct ttg agc gaa cac ttc ttc acc ctt ttg       193
Asn Val His Lys Ile Tyr Pro Leu Ser Glu His Phe Phe Thr Leu Leu
    50                  55                  60 gaa gaa tca gga tat ttc                                                211
Glu Glu Ser Gly Tyr Phe
```

```
65                  70

<210> SEQ ID NO 20
<211> LENGTH: 70
<212> TYPE: PRT
<213> ORGANISM: Ctenocephalides felis

<400> SEQUENCE: 20

Ser Arg Ile Val Ser Ala Met Ser Thr Leu Phe Pro Glu Asn Val Leu
 1               5                  10                  15

Gly His His Ser Asn Leu Cys Phe Leu Asn Thr Leu Ser Ser Asn Ile
            20                  25                  30

Lys Ser Phe Val Gly Ser Leu Phe Pro Glu Trp Phe Ala Gly Lys Gln
        35                  40                  45

Asn Val His Lys Ile Tyr Pro Leu Ser Glu His Phe Phe Thr Leu Leu
    50                  55                  60

Glu Glu Ser Gly Tyr Phe
65                  70

<210> SEQ ID NO 21
<211> LENGTH: 211
<212> TYPE: DNA
<213> ORGANISM: Ctenocephalides felis

<400> SEQUENCE: 21
ttctagaatc gtcagcgcta tgtcaacttt gtttccagaa atgttcttg gacaccattc        60 taatttatgc tttttaaata cactatcttc aaatataaag tcctttgttg gcagtttatt      120
cccagaatgg tttgctggaa acaaaatgt tcataaaatc tatcctttga gcgaacactt       180 cttcacccctt ttggaagaat caggatattt c                                     211

<210> SEQ ID NO 22
<211> LENGTH: 1736
<212> TYPE: DNA
<213> ORGANISM: Ctenocephalides felis
<220> FEATURE:
<221> NAME/KEY: CDS
<222> LOCATION: (159)..(1553)

<400> SEQUENCE: 22
tgctagaggt attagaggta aataaataaa aaaaatactt ttatgataac agaaaaaaaa        60
ctacaggttt aatgaaatca gttaaaatca gagtgaattt taacatataa atttaaatat      120
tataaaaatc atcttagctt ttacaaactt aaattgca atg agt aat tgt tgt cga      176
                                           Met Ser Asn Cys Cys Arg
                                            1               5 ata tta tgg att gcg ata gtg atc ggt tta ggt gtg ttg tat tac gaa        224
Ile Leu Trp Ile Ala Ile Val Ile Gly Leu Gly Val Leu Tyr Tyr Glu
            10                  15                  20 ata act aaa gaa ttt cca aag cca aat ata cct ctg gat aca tgg tgg        272
Ile Thr Lys Glu Phe Pro Lys Pro Asn Ile Pro Leu Asp Thr Trp Trp
        25                  30                  35 gga act gga aaa tca caa aaa att gat aca tca atg agg ccg ttt aaa        320
Gly Thr Gly Lys Ser Gln Lys Ile Asp Thr Ser Met Arg Pro Phe Lys
    40                  45                  50 att gcc ata aac gat gag gtc ctt aat acc ttg aaa gtg aaa cta agt        368
Ile Ala Ile Asn Asp Glu Val Leu Asn Thr Leu Lys Val Lys Leu Ser
55                  60                  65                  70 gat gtg tcc ttt act cca cct ctt gag ggc atc gat ttc caa tat ggt        416
Asp Val Ser Phe Thr Pro Pro Leu Glu Gly Ile Asp Phe Gln Tyr Gly
            75                  80                  85
```

-continued

```
ttc aat aca aat acc ctg aaa aaa ctt gta gac ttt tgg cga act caa      464
Phe Asn Thr Asn Thr Leu Lys Lys Leu Val Asp Phe Trp Arg Thr Gln
                 90                  95                 100 tac aat tgg cgc gaa cgt gaa gca tta ttg aat aaa tat cca cac ttc      512
Tyr Asn Trp Arg Glu Arg Glu Ala Leu Leu Asn Lys Tyr Pro His Phe
            105                 110                 115 aaa aca aat att caa ggc ctg gat att cac tat gtt cac ata aaa cca      560
Lys Thr Asn Ile Gln Gly Leu Asp Ile His Tyr Val His Ile Lys Pro
        120                 125                 130 cag gtc tcc aaa aat atc cat gtt ctg cca atg att atg gtt cat ggt      608
Gln Val Ser Lys Asn Ile His Val Leu Pro Met Ile Met Val His Gly
135                 140                 145                 150 tgg cca ggg tca ttc gtg gaa ttt tat aag att att cct atg ttg acg      656
Trp Pro Gly Ser Phe Val Glu Phe Tyr Lys Ile Ile Pro Met Leu Thr
                155                 160                 165 act ccg aga aca gat tac aat ttt gta ttc gaa ttg ata ttg cct agt      704
Thr Pro Arg Thr Asp Tyr Asn Phe Val Phe Glu Leu Ile Leu Pro Ser
            170                 175                 180 att ccg ggt tat ggg ttt tca cag gct gca gct aaa cct ggt ctt ggt      752
Ile Pro Gly Tyr Gly Phe Ser Gln Ala Ala Ala Lys Pro Gly Leu Gly
        185                 190                 195 gct act caa att gcg gtt ata atg cac aac ttg atg gat cgc att gga      800
Ala Thr Gln Ile Ala Val Ile Met His Asn Leu Met Asp Arg Ile Gly
200                 205                 210 ttc aaa aag tat tac gta caa ggt ggc gat tgg ggt tct aga atc gtc      848
Phe Lys Lys Tyr Tyr Val Gln Gly Gly Asp Trp Gly Ser Arg Ile Val
215                 220                 225                 230 agc gct atg tca act ttg ttt cca gaa aat gtt ctt gga cac cat tct      896
Ser Ala Met Ser Thr Leu Phe Pro Glu Asn Val Leu Gly His His Ser
                235                 240                 245 aat tta tgc ttt tta aat aca cta tct tca aat ata aag tcc ttt gtt      944
Asn Leu Cys Phe Leu Asn Thr Leu Ser Ser Asn Ile Lys Ser Phe Val
            250                 255                 260 ggc agt tta ttc cca gaa tgg ttt gct gga aaa caa aat gtt cat aaa      992
Gly Ser Leu Phe Pro Glu Trp Phe Ala Gly Lys Gln Asn Val His Lys
        265                 270                 275 atc tat cct ttg agc gaa cac ttc ttc acc ctt ttg gaa gaa tca gga     1040
Ile Tyr Pro Leu Ser Glu His Phe Phe Thr Leu Leu Glu Glu Ser Gly
280                 285                 290 tat ttc cat atc caa gct aca aaa cct gac aca gtt ggc gtt gct ttg     1088
Tyr Phe His Ile Gln Ala Thr Lys Pro Asp Thr Val Gly Val Ala Leu
295                 300                 305                 310 aga gat tcg cca gct gga ttg gcg gct tat att tta gaa aaa ttt tca     1136
Arg Asp Ser Pro Ala Gly Leu Ala Ala Tyr Ile Leu Glu Lys Phe Ser
                315                 320                 325 acg ggt act aac aaa gct tgg aga tct gct aaa gat gga aat cta caa     1184
Thr Gly Thr Asn Lys Ala Trp Arg Ser Ala Lys Asp Gly Asn Leu Gln
            330                 335                 340 tca aaa ttt act ttt acg gaa ctt ctc gac aac gta atg ata tac tat     1232
Ser Lys Phe Thr Phe Thr Glu Leu Leu Asp Asn Val Met Ile Tyr Tyr
        345                 350                 355 gtc act ggt tca att aca act tcg atg aga att tat gca gag tca tac     1280
Val Thr Gly Ser Ile Thr Thr Ser Met Arg Ile Tyr Ala Glu Ser Tyr
360                 365                 370 tcg tgg gat cac ttg agt ttg aac atg gat agg gtg cca act att gtg     1328
Ser Trp Asp His Leu Ser Leu Asn Met Asp Arg Val Pro Thr Ile Val
375                 380                 385                 390 ccg act gct tgt gca aaa ttt ccc cat gag ata gct tat aaa aca gac     1376
Pro Thr Ala Cys Ala Lys Phe Pro His Glu Ile Ala Tyr Lys Thr Asp
```

```
                          395                 400                 405
ttc caa ttg gca gaa aaa tac aaa acg tta ttg cag tcc act att atg      1424
Phe Gln Leu Ala Glu Lys Tyr Lys Thr Leu Leu Gln Ser Thr Ile Met
            410                 415                 420 cca aga ggc gga cat ttt gct gca ttg gaa gaa cca ctt ctt cta gca      1472
Pro Arg Gly Gly His Phe Ala Ala Leu Glu Glu Pro Leu Leu Leu Ala
        425                 430                 435 gaa gat atc ttt agt gct gtc aag aaa ttt atc gac cac cat tcc aaa      1520
Glu Asp Ile Phe Ser Ala Val Lys Lys Phe Ile Asp His His Ser Lys
    440                 445                 450 aaa gac agc aaa aac caa gag aat aga gat ctc tgagaacttg taataaatta    1573
Lys Asp Ser Lys Asn Gln Glu Asn Arg Asp Leu
455                 460                 465 tttgtgataa taatataatg ttaaaaataa atgtaattac tgtgaaataa acgatatgga    1633
ttttatttca aacttgtcaa atataaaaaa aaaaaaaaaa aaaaaaaaaa aaaaaaaaaa    1693
aaaaaaaaaa aaaaaaaaaa aaaaaaaaaa aaaaaaaaaa aaa                      1736

<210> SEQ ID NO 23
<211> LENGTH: 465
<212> TYPE: PRT
<213> ORGANISM: Ctenocephalides felis

<400> SEQUENCE: 23

Met Ser Asn Cys Cys Arg Ile Leu Trp Ile Ala Ile Val Ile Gly Leu
 1               5                  10                  15

Gly Val Leu Tyr Tyr Glu Ile Thr Lys Glu Phe Pro Lys Pro Asn Ile
                20                  25                  30

Pro Leu Asp Thr Trp Trp Gly Thr Gly Lys Ser Gln Lys Ile Asp Thr
            35                  40                  45

Ser Met Arg Pro Phe Lys Ile Ala Ile Asn Asp Glu Val Leu Asn Thr
        50                  55                  60

Leu Lys Val Lys Leu Ser Asp Val Ser Phe Thr Pro Pro Leu Glu Gly
65                  70                  75                  80

Ile Asp Phe Gln Tyr Gly Phe Asn Thr Asn Thr Leu Lys Lys Leu Val
                85                  90                  95

Asp Phe Trp Arg Thr Gln Tyr Asn Trp Arg Glu Arg Glu Ala Leu Leu
            100                 105                 110

Asn Lys Tyr Pro His Phe Lys Thr Asn Ile Gln Gly Leu Asp Ile His
        115                 120                 125

Tyr Val His Ile Lys Pro Gln Val Ser Lys Asn Ile His Val Leu Pro
    130                 135                 140

Met Ile Met Val His Gly Trp Pro Gly Ser Phe Val Glu Phe Tyr Lys
145                 150                 155                 160

Ile Ile Pro Met Leu Thr Thr Pro Arg Thr Asp Tyr Asn Phe Val Phe
                165                 170                 175

Glu Leu Ile Leu Pro Ser Ile Pro Gly Tyr Gly Phe Ser Gln Ala Ala
            180                 185                 190

Ala Lys Pro Gly Leu Gly Ala Thr Gln Ile Ala Val Ile Met His Asn
        195                 200                 205

Leu Met Asp Arg Ile Gly Phe Lys Lys Tyr Tyr Val Gln Gly Gly Asp
    210                 215                 220

Trp Gly Ser Arg Ile Val Ser Ala Met Ser Thr Leu Phe Pro Glu Asn
225                 230                 235                 240

Val Leu Gly His His Ser Asn Leu Cys Phe Leu Asn Thr Leu Ser Ser
                245                 250                 255
```

```
Asn Ile Lys Ser Phe Val Gly Ser Leu Phe Pro Glu Trp Phe Ala Gly
                260                 265                 270
Lys Gln Asn Val His Lys Ile Tyr Pro Leu Ser Glu His Phe Phe Thr
            275                 280                 285
Leu Leu Glu Glu Ser Gly Tyr Phe His Ile Gln Ala Thr Lys Pro Asp
        290                 295                 300
Thr Val Gly Val Ala Leu Arg Asp Ser Pro Ala Gly Leu Ala Ala Tyr
305                 310                 315                 320
Ile Leu Glu Lys Phe Ser Thr Gly Thr Asn Lys Ala Trp Arg Ser Ala
                325                 330                 335
Lys Asp Gly Asn Leu Gln Ser Lys Phe Thr Phe Thr Glu Leu Leu Asp
            340                 345                 350
Asn Val Met Ile Tyr Tyr Val Thr Gly Ser Ile Thr Thr Ser Met Arg
        355                 360                 365
Ile Tyr Ala Glu Ser Tyr Ser Trp Asp His Leu Ser Leu Asn Met Asp
370                 375                 380
Arg Val Pro Thr Ile Val Pro Thr Ala Cys Ala Lys Phe Pro His Glu
385                 390                 395                 400
Ile Ala Tyr Lys Thr Asp Phe Gln Leu Ala Glu Lys Tyr Lys Thr Leu
                405                 410                 415
Leu Gln Ser Thr Ile Met Pro Arg Gly Gly His Phe Ala Ala Leu Glu
            420                 425                 430
Glu Pro Leu Leu Leu Ala Glu Asp Ile Phe Ser Ala Val Lys Lys Phe
        435                 440                 445
Ile Asp His His Ser Lys Lys Asp Ser Lys Asn Gln Glu Asn Arg Asp
    450                 455                 460
Leu
465

<210> SEQ ID NO 24
<211> LENGTH: 1736
<212> TYPE: DNA
<213> ORGANISM: Ctenocephalides felis

<400> SEQUENCE: 24
tttttttttt tttttttttt tttttttttt tttttttttt tttttttttt tttttttttt      60
tttttttttt ttttttttta tatttgacaa gtttgaaata aatccatat cgtttatttc     120 acagtaatta catttatttt taacattata ttattatcac aaataattta ttacaagttc     180
tcagagatct ctattctctt ggttttgct gtcttttttg aatggtggt cgataaattt      240 cttgacagca ctaaagatat cttctgctag aagaagtggt tcttccaatg cagcaaaatg     300
tccgcctctt ggcataatag tggactgcaa taacgttttg tatttttctg ccaattggaa     360
gtctgtttta taagctatct catggggaaa ttttgcacaa gcagtcggca caatagttgg     420
caccctatcc atgttcaaac tcaagtgatc ccacgagtat gactctgcat aaattctcat     480
cgaagttgta attgaaccag tgacatagta tatcattacg ttgtcgagaa gttccgtaaa     540
agtaaatttt gattgtagat tccatctctt agcagatctc caagctttgt tagtacccgt     600
tgaaattttt tctaaaatat aagccgccaa tccagctggc gaatctctca agcaacgcc      660 aactgtgtca ggttttgtag cttggatatg gaaatatcct gattcttcca aagggtgaa     720 gaagtgttcg ctcaaggat agattttatg aacattttgt tttccagcaa accattctgg     780
gaataaactg ccaacaaagg actttatatt tgaagatagt gtatttaaaa agcataaatt     840
agaatggtgt ccaagaacat tttctggaaa caaagttgac atagcgctga cgattctaga     900
```

```
accccaatcg ccaccttgta cgtaatactt tttgaatcca atgcgatcca tcaagttgtg      960
cattataacc gcaatttgag tagcaccaag accaggttta gctgcagcct gtgaaaaccc     1020
ataacccgga atactaggca atatcaattc gaatacaaaa ttgtaatctg ttctcggagt     1080
cgtcaacata ggataatct tataaaattc cacgaatgac cctggccaac catgaaccat      1140
aatcattggc agaacatgga tatttttgga gacctgtggt tttatgtgaa catagtgaat     1200
atccaggcct tgaatatttg ttttgaagtg tggatattta ttcaataatg cttcacgttc     1260
gcgccaattg tattgagttc gccaaaagtc tacaagtttt tcagggtat ttgtattgaa      1320 accatattgg aaatcgatgc cctcaagagg tggagtaaag dacacatcac ttagtttcac     1380
tttcaaggta ttaaggacct catcgtttat ggcaatttta aacggcctca ttgatgtatc     1440 aatttttgt gattttccag ttccccacca tgtatccaga ggtatatttg ctttggaaa      1500 ttctttagtt atttcgtaat acaacacacc taaaccgatc actatcgcaa tcataatat     1560 tcgacaacaa ttactcattg caatttaagt ttgtaaaagc taagatgatt tttataatat    1620
ttaaatttat atgttaaaat tcactctgat tttaactgat ttcattaaac ctgtagtttt    1680
ttttctgtta tcataaaagt attttttta tttatttacc tctaatacct ctagca          1736

<210> SEQ ID NO 25
<211> LENGTH: 1395
<212> TYPE: DNA
<213> ORGANISM: Ctenocephalides felis

<400> SEQUENCE: 25
atgagtaatt gttgtcgaat attatggatt gcgatagtga tcggtttagg tgtgttgtat      60
tacgaaataa ctaaagaatt ccaaagcca aatatacctc tggatacatg gtggggaact      120
ggaaaatcac aaaaaattga tacatcaatg aggccgttta aaattgccat aaacgatgag     180
gtccttaata cctttgaaagt gaaactaagt gatgtgtcct ttactccacc tcttgagggc    240
atcgatttcc aatatggttt caatacaaat accctgaaaa aacttgtaga cttttggcga    300
actcaataca attggcgcga acgtgaagca ttattgaata aatatccaca cttcaaaaca    360
aatattcaag gcctggatat tcactatgtt cacataaaac cacaggtctc caaaaatatc    420
catgttctgc caatgattat ggttcatggt tggccagggt cattcgtgga attttataag    480
attattccta tgttgacgac tccgagaaca gattacaatt ttgtattcga attgatattg    540
cctagtattc cgggttatgg gttttcacag gctgcagcta aacctggtct tggtgctact    600
caaattgcgg ttataatgca caacttgatg atcgcattg gattcaaaaa gtattacgta    660
caaggtggcg attggggttc tagaatcgtc agcgctatgt caactttgtt tccagaaaat    720
gttcttggac accattctaa tttatgcttt ttaaatacac tatcttcaaa tataaagtcc    780
tttgttggca gtttattccc agaatggttt gctggaaaac aaaatgttca taaaatctat    840
cctttgagcg aacacttctt caccctttg gaagaatcag gatatttcca tatccaagct    900
acaaaacctg cacagttgg cgttgctttg agagattcgc cagctggatt ggcggcttat    960 atttagaaa attttcaac gggtactaac aaagcttgga gatctgctaa agatggaaat    1020
ctacaatcaa aattactttt tacgaaactt ctcgacaacg taatgataa ctatgtcact   1080 ggttcaatta caacttcgat gagaaattat gcagagtcat actcgtggga tcacttgagt    1140
ttgaacatgg atagggtgcc aactattgtg ccgactgctt gtgcaaaatt tccccatgag    1200
atagcttata aaacagactt ccaattggca gaaaaatca aaacgttatt gcagtccact    1260
```

-continued

| attatgccaa gaggcggaca ttttgctgca ttggaagaac cacttcttct agcagaagat | 1320 |
| atctttagtg ctgtcaagaa atttatcgac caccattcca aaaagacag caaaaaccaa | 1380 |
| gagaatagag atctc | 1395 |

<210> SEQ ID NO 26
<211> LENGTH: 1395
<212> TYPE: DNA
<213> ORGANISM: Ctenocephalides felis

<400> SEQUENCE: 26

| gagatctcta ttctcttggt ttttgctgtc tttttttggaa tggtggtcga taaatttctt | 60 |
| gacagcacta aagatatctt ctgctagaag aagtggttct tccaatgcag caaaatgtcc | 120 |
| gcctcttggc ataatagtgg actgcaataa cgttttgtat ttttctgcca attggaagtc | 180 |
| tgttttataa gctatctcat ggggaaattt tgcacaagca gtcggcacaa tagttggcac | 240 |
| cctatccatg ttcaaactca agtgatccca cgagtatgac tctgcataaa ttctcatcga | 300 |
| agttgtaatt gaaccagtga catagtatat cattacgttg tcgagaagtt ccgtaaaagt | 360 |
| aaattttgat tgtagatttc catctttagc agatctccaa gctttgttag tacccgttga | 420 |
| aaattttctc aaaatataag ccgccaatcc agctggcgaa tctctcaaag caacgccaac | 480 |
| tgtgtcaggt tttgtagctt ggatatggaa atatcctgat tcttccaaaa gggtgaagaa | 540 |
| gtgttcgctc aaaggataga ttttatgaac attttgtttt ccagcaaacc attctgggaa | 600 |
| taaactgcca acaaaggact ttatatttga agatagtgta tttaaaaagc ataaattaga | 660 |
| atggtgtcca agaacatttt ctggaaacaa agttgacata gcgctgacga ttctagaacc | 720 |
| ccaatcgcca ccttgtacgt aatactttt gaatccaatg cgatccatca agttgtgcat | 780 |
| tataaccgca atttgagtag caccaagacc aggtttagct gcagcctgtg aaaacccata | 840 |
| acccggaata ctaggcaata tcaattcgaa tacaaaattg taatctgttc tcggagtcgt | 900 |
| caacatagga ataatcttat aaaattccac gaatgaccct ggccaaccat gaaccataat | 960 |
| cattggcaga acatggatat ttttggagac ctgtggtttt atgtgaacat agtgaatatc | 1020 |
| caggccttga atatttgttt tgaagtgtgg atatttattc aataatgctt cacgttcgcg | 1080 |
| ccaattgtat tgagttcgcc aaaagtctac aagttttttc agggtatttg tattgaaacc | 1140 |
| atattggaaa tcgatgccct caagaggtgg agtaaaggac acatcactta gtttcacttt | 1200 |
| caaggtatta aggacctcat cgtttatggc aatttttaaac ggcctcattg atgtatcaat | 1260 |
| tttttgtgat tttccagttc cccaccatgt atccagaggt atatttggct ttggaaattc | 1320 |
| tttagttatt tcgtaataca acacacctaa accgatcact atcgcaatcc ataatattcg | 1380 |
| acaacaatta ctcat | 1395 |

<210> SEQ ID NO 27
<211> LENGTH: 1293
<212> TYPE: DNA
<213> ORGANISM: Ctenocephalides felis
<220> FEATURE:
<221> NAME/KEY: CDS
<222> LOCATION: (2)..(1291)

<400> SEQUENCE: 27

| a aag cca aat ata cct ctg gat aca tgg tgg gga act gga aaa tca caa | 49 |
|   Lys Pro Asn Ile Pro Leu Asp Thr Trp Trp Gly Thr Gly Lys Ser Gln | |
|     1               5                  10                  15 | |

| aaa att gat aca tca atg agg ccg ttt aaa att gcc ata aac gat gag | 97 |
|   Lys Ile Asp Thr Ser Met Arg Pro Phe Lys Ile Ala Ile Asn Asp Glu | |

```
                    20                      25                        30
gtc ctt aat acc ttg aaa gtg aaa cta agt gat gtg tcc ttt act cca        145
Val Leu Asn Thr Leu Lys Val Lys Leu Ser Asp Val Ser Phe Thr Pro
            35                      40                      45 cct ctt gag ggc atc gat ttc caa tat ggt ttc aat aca aat acc ctg        193
Pro Leu Glu Gly Ile Asp Phe Gln Tyr Gly Phe Asn Thr Asn Thr Leu
 50                      55                      60 aaa aaa ctt gta gac ttt tgg cga act caa tac aat tgg cgc gaa cgt        241
Lys Lys Leu Val Asp Phe Trp Arg Thr Gln Tyr Asn Trp Arg Glu Arg
 65                      70                      75                  80 gaa gca tta ttg aat aaa tat cca cac ttc aaa aca aat att caa ggc        289
Glu Ala Leu Leu Asn Lys Tyr Pro His Phe Lys Thr Asn Ile Gln Gly
                85                      90                      95 ctg gat att cac tat gtt cac ata aaa cca cag gtc tcc aaa aat atc        337
Leu Asp Ile His Tyr Val His Ile Lys Pro Gln Val Ser Lys Asn Ile
            100                     105                     110 cat gtt ctg cca atg att atg gtt cat ggt tgg cca ggg tca ttc gtg        385
His Val Leu Pro Met Ile Met Val His Gly Trp Pro Gly Ser Phe Val
            115                     120                     125 gaa ttt tat aag att att cct atg ttg acg act ccg aga aca gat tac        433
Glu Phe Tyr Lys Ile Ile Pro Met Leu Thr Thr Pro Arg Thr Asp Tyr
 130                     135                     140 aat ttt gta ttc gaa ttg ata ttg cct agt att ccg ggt tat ggg ttt        481
Asn Phe Val Phe Glu Leu Ile Leu Pro Ser Ile Pro Gly Tyr Gly Phe
145                     150                     155                 160 tca cag gct gca gct aaa cct ggt ctt ggt gct act caa att gcg gtt        529
Ser Gln Ala Ala Ala Lys Pro Gly Leu Gly Ala Thr Gln Ile Ala Val
            165                     170                     175 ata atg cac aac ttg atg gat cgc att gga ttc aaa aag tat tac gta        577
Ile Met His Asn Leu Met Asp Arg Ile Gly Phe Lys Lys Tyr Tyr Val
            180                     185                     190 caa ggt ggc gat tgg ggt tct aga atc gtc agc gct atg tca act ttg        625
Gln Gly Gly Asp Trp Gly Ser Arg Ile Val Ser Ala Met Ser Thr Leu
            195                     200                     205 ttt cca gaa aat gtt ctt gga cac cat tct aat tta tgc ttt tta aat        673
Phe Pro Glu Asn Val Leu Gly His His Ser Asn Leu Cys Phe Leu Asn
            210                     215                     220 aca cta tct tca aat ata aag tcc ttt gtt ggc agt tta ttc cca gaa        721
Thr Leu Ser Ser Asn Ile Lys Ser Phe Val Gly Ser Leu Phe Pro Glu
225                     230                     235                 240 tgg ttt gct gga aaa caa aat gtt cat aaa atc tat cct ttg agc gaa        769
Trp Phe Ala Gly Lys Gln Asn Val His Lys Ile Tyr Pro Leu Ser Glu
            245                     250                     255 cac ttc ttc acc ctt ttg gaa gaa tca gga tat ttc cat atc caa gct        817
His Phe Phe Thr Leu Leu Glu Glu Ser Gly Tyr Phe His Ile Gln Ala
            260                     265                     270 aca aaa cct gac aca gtt ggc gtt gct ttg aga gat tcg cca gct gga        865
Thr Lys Pro Asp Thr Val Gly Val Ala Leu Arg Asp Ser Pro Ala Gly
            275                     280                     285 ttg gcg gct tat att tta gaa aaa ttt tca acg ggt act aac aaa gct        913
Leu Ala Ala Tyr Ile Leu Glu Lys Phe Ser Thr Gly Thr Asn Lys Ala
            290                     295                     300 tgg aga tct gct aaa gat gga aat cta caa tca aaa ttt act ttt acg        961
Trp Arg Ser Ala Lys Asp Gly Asn Leu Gln Ser Lys Phe Thr Phe Thr
305                     310                     315                 320 gaa ctt ctc gac aac gta atg ata tac tat gtc act ggt tca att aca       1009
Glu Leu Leu Asp Asn Val Met Ile Tyr Tyr Val Thr Gly Ser Ile Thr
            325                     330                     335 act tcg atg aga att tat gca gag tca tac tcg tgg gat cac ttg agt       1057
```

```
Thr Ser Met Arg Ile Tyr Ala Glu Ser Tyr Ser Trp Asp His Leu Ser
            340                 345                 350 ttg aac atg gat agg gtg cca act att gtg ccg act gct tgt gca aaa    1105
Leu Asn Met Asp Arg Val Pro Thr Ile Val Pro Thr Ala Cys Ala Lys
            355                 360                 365 ttt ccc cat gag ata gct tat aaa aca gac ttc caa ttg gca gaa aaa    1153
Phe Pro His Glu Ile Ala Tyr Lys Thr Asp Phe Gln Leu Ala Glu Lys
    370                 375                 380 tac aaa acg tta ttg cag tcc act att atg cca aga ggc gga cat ttt    1201
Tyr Lys Thr Leu Leu Gln Ser Thr Ile Met Pro Arg Gly Gly His Phe
385                 390                 395                 400 gct gca ttg gaa gaa cca ctt ctt cta gca gaa gat atc ttt agt gct    1249
Ala Ala Leu Glu Glu Pro Leu Leu Leu Ala Glu Asp Ile Phe Ser Ala
                405                 410                 415 gtc aag aaa ttt atc gac cac cat tcc aaa aaa gac agc aaa aa        1293
Val Lys Lys Phe Ile Asp His His Ser Lys Lys Asp Ser Lys
            420                 425                 430

<210> SEQ ID NO 28
<211> LENGTH: 430
<212> TYPE: PRT
<213> ORGANISM: Ctenocephalides felis

<400> SEQUENCE: 28

Lys Pro Asn Ile Pro Leu Asp Thr Trp Trp Gly Thr Gly Lys Ser Gln
 1               5                  10                  15

Lys Ile Asp Thr Ser Met Arg Pro Phe Lys Ile Ala Ile Asn Asp Glu
            20                  25                  30

Val Leu Asn Thr Leu Lys Val Lys Leu Ser Asp Val Ser Phe Thr Pro
        35                  40                  45

Pro Leu Glu Gly Ile Asp Phe Gln Tyr Gly Phe Asn Thr Asn Thr Leu
    50                  55                  60

Lys Lys Leu Val Asp Phe Trp Arg Thr Gln Tyr Asn Trp Arg Glu Arg
65                  70                  75                  80

Glu Ala Leu Leu Asn Lys Tyr Pro His Phe Lys Thr Asn Ile Gln Gly
                85                  90                  95

Leu Asp Ile His Tyr Val His Ile Lys Pro Gln Val Ser Lys Asn Ile
            100                 105                 110

His Val Leu Pro Met Ile Met Val His Gly Trp Pro Gly Ser Phe Val
        115                 120                 125

Glu Phe Tyr Lys Ile Ile Pro Met Leu Thr Thr Pro Arg Thr Asp Tyr
    130                 135                 140

Asn Phe Val Phe Glu Leu Ile Leu Pro Ser Ile Pro Gly Tyr Gly Phe
145                 150                 155                 160

Ser Gln Ala Ala Ala Lys Pro Gly Leu Gly Ala Thr Gln Ile Ala Val
                165                 170                 175

Ile Met His Asn Leu Met Asp Arg Ile Gly Phe Lys Lys Tyr Tyr Val
            180                 185                 190

Gln Gly Gly Asp Trp Gly Ser Arg Ile Val Ser Ala Met Ser Thr Leu
        195                 200                 205

Phe Pro Glu Asn Val Leu Gly His His Ser Asn Leu Cys Phe Leu Asn
    210                 215                 220

Thr Leu Ser Ser Asn Ile Lys Ser Phe Val Gly Ser Leu Phe Pro Glu
225                 230                 235                 240

Trp Phe Ala Gly Lys Gln Asn Val His Lys Ile Tyr Pro Leu Ser Glu
                245                 250                 255
```

```
His Phe Phe Thr Leu Glu Glu Ser Gly Tyr Phe His Ile Gln Ala
            260                 265                 270

Thr Lys Pro Asp Thr Val Gly Val Ala Leu Arg Asp Ser Pro Ala Gly
        275                 280                 285

Leu Ala Ala Tyr Ile Leu Glu Lys Phe Ser Thr Gly Thr Asn Lys Ala
        290                 295                 300

Trp Arg Ser Ala Lys Asp Gly Asn Leu Gln Ser Lys Phe Thr Phe Thr
305                 310                 315                 320

Glu Leu Leu Asp Asn Val Met Ile Tyr Tyr Val Thr Gly Ser Ile Thr
                325                 330                 335

Thr Ser Met Arg Ile Tyr Ala Glu Ser Tyr Ser Trp Asp His Leu Ser
            340                 345                 350

Leu Asn Met Asp Arg Val Pro Thr Ile Val Pro Thr Ala Cys Ala Lys
        355                 360                 365

Phe Pro His Glu Ile Ala Tyr Lys Thr Asp Phe Gln Leu Ala Glu Lys
    370                 375                 380

Tyr Lys Thr Leu Leu Gln Ser Thr Ile Met Pro Arg Gly Gly His Phe
385                 390                 395                 400

Ala Ala Leu Glu Glu Pro Leu Leu Ala Glu Asp Ile Phe Ser Ala
                405                 410                 415

Val Lys Lys Phe Ile Asp His Ser Lys Lys Asp Ser Lys
            420                 425                 430

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 29
aaaggatccg ataactaaag aatttcc                                          27

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 30
attgaattct cagagatctc tattctcttg g                                     31

<210> SEQ ID NO 31
<211> LENGTH: 25
<212> TYPE: PRT
<213> ORGANISM: Ctenocephalides felis

<400> SEQUENCE: 31

Gly Lys Xaa Xaa Arg Met Leu Ile Phe Ala Ala Ile Ala Gly Ile Ala
 1               5                  10                  15

Val Leu Tyr Tyr Gln Ile Thr Lys Glu
            20                  25

<210> SEQ ID NO 32
<211> LENGTH: 1326
<212> TYPE: DNA
<213> ORGANISM: Ctenocephalides felis
<220> FEATURE:
```

<211> NAME/KEY: CDS
<222> LOCATION: (1)..(1326)

<400> SEQUENCE: 32

| | | | | | | | | | | | | | | | | |
|---|---|---|---|---|---|---|---|---|---|---|---|---|---|---|---|---|
| att | acg | aaa | gaa | ctt | cca | aaa | cca | aat | ata | cct | ctc | gac | act | tgg | tgg | 48 |
| Ile | Thr | Lys | Glu | Leu | Pro | Lys | Pro | Asn | Ile | Pro | Leu | Asp | Thr | Trp | Trp | |
| 1 | | | | 5 | | | | | 10 | | | | | 15 | | |
| ggt | cca | gga | aag | cca | caa | aat | gtt | gac | ata | tca | ata | aga | ccg | ttt | aaa | 96 |
| Gly | Pro | Gly | Lys | Pro | Gln | Asn | Val | Asp | Ile | Ser | Ile | Arg | Pro | Phe | Lys | |
| | | | 20 | | | | | 25 | | | | | 30 | | | |
| att | aat | att | aat | aac | aaa | gtg | att | gaa | aat | ctg | aaa | cta | aaa | ctc | aat | 144 |
| Ile | Asn | Ile | Asn | Asn | Lys | Val | Ile | Glu | Asn | Leu | Lys | Leu | Lys | Leu | Asn | |
| | | 35 | | | | | 40 | | | | | 45 | | | | |
| gat | gtt | caa | tat | act | tta | cct | tta | gag | ggc | atc | aat | ttt | gaa | tat | ggt | 192 |
| Asp | Val | Gln | Tyr | Thr | Leu | Pro | Leu | Glu | Gly | Ile | Asn | Phe | Glu | Tyr | Gly | |
| 50 | | | | | 55 | | | | | 60 | | | | | | |
| ttc | aat | aca | gat | tcc | ctg | aaa | aag | att | gta | gat | ttt | tgg | cga | act | caa | 240 |
| Phe | Asn | Thr | Asp | Ser | Leu | Lys | Lys | Ile | Val | Asp | Phe | Trp | Arg | Thr | Gln | |
| 65 | | | | | 70 | | | | | 75 | | | | | 80 | |
| tat | aat | tgg | cgt | gaa | cgt | gaa | gca | tta | tta | aat | aaa | tat | cca | cac | ttc | 288 |
| Tyr | Asn | Trp | Arg | Glu | Arg | Glu | Ala | Leu | Leu | Asn | Lys | Tyr | Pro | His | Phe | |
| | | | | 85 | | | | | 90 | | | | | 95 | | |
| aaa | aca | aat | att | caa | ggc | ctg | gat | att | cat | tat | gtc | cac | ata | aaa | cca | 336 |
| Lys | Thr | Asn | Ile | Gln | Gly | Leu | Asp | Ile | His | Tyr | Val | His | Ile | Lys | Pro | |
| | | | 100 | | | | | 105 | | | | | 110 | | | |
| cag | gtc | tct | aaa | aat | att | gaa | gtt | ttg | cct | ttg | gta | atg | atc | cat | ggt | 384 |
| Gln | Val | Ser | Lys | Asn | Ile | Glu | Val | Leu | Pro | Leu | Val | Met | Ile | His | Gly | |
| | | 115 | | | | | 120 | | | | | 125 | | | | |
| tgg | cca | gga | tct | ttt | gtg | gaa | ttc | tac | aag | atc | ata | cct | atg | ttg | aca | 432 |
| Trp | Pro | Gly | Ser | Phe | Val | Glu | Phe | Tyr | Lys | Ile | Ile | Pro | Met | Leu | Thr | |
| 130 | | | | | 135 | | | | | 140 | | | | | | |
| act | cca | aga | gca | ggt | tac | aat | ttc | gta | ttc | gaa | ttg | ata | ttg | cct | agt | 480 |
| Thr | Pro | Arg | Ala | Gly | Tyr | Asn | Phe | Val | Phe | Glu | Leu | Ile | Leu | Pro | Ser | |
| 145 | | | | | 150 | | | | | 155 | | | | | 160 | |
| att | cct | gga | tac | ggc | ttt | tca | cag | gct | gca | gct | aaa | cct | ggt | ctt | gga | 528 |
| Ile | Pro | Gly | Tyr | Gly | Phe | Ser | Gln | Ala | Ala | Ala | Lys | Pro | Gly | Leu | Gly | |
| | | | | 165 | | | | | 170 | | | | | 175 | | |
| tcg | act | cag | gtc | gcc | gtt | ata | atg | cgc | aat | ttg | atg | gag | cgc | att | gga | 576 |
| Ser | Thr | Gln | Val | Ala | Val | Ile | Met | Arg | Asn | Leu | Met | Glu | Arg | Ile | Gly | |
| | | | 180 | | | | | 185 | | | | | 190 | | | |
| ttc | aaa | aaa | tat | tat | gta | caa | gga | ggc | gac | tgg | ggt | tct | atg | atc | ata | 624 |
| Phe | Lys | Lys | Tyr | Tyr | Val | Gln | Gly | Gly | Asp | Trp | Gly | Ser | Met | Ile | Ile | |
| | | | 195 | | | | | 200 | | | | | 205 | | | |
| agc | gcg | atg | tca | aca | tta | ttt | cca | gaa | aat | gtc | ctg | gga | cag | cac | tca | 672 |
| Ser | Ala | Met | Ser | Thr | Leu | Phe | Pro | Glu | Asn | Val | Leu | Gly | Gln | His | Ser | |
| | | 210 | | | | | 215 | | | | | 220 | | | | |
| aac | atg | tgt | ttt | gtc | aat | act | cca | tca | tca | aat | atc | aag | gct | ata | att | 720 |
| Asn | Met | Cys | Phe | Val | Asn | Thr | Pro | Ser | Ser | Asn | Ile | Lys | Ala | Ile | Ile | |
| 225 | | | | | 230 | | | | | 235 | | | | | 240 | |
| gga | agc | ttt | ttc | ccg | gaa | tcg | ttt | gct | ggc | acg | gga | aat | gcg | cat | aaa | 768 |
| Gly | Ser | Phe | Phe | Pro | Glu | Ser | Phe | Ala | Gly | Thr | Gly | Asn | Ala | His | Lys | |
| | | | | 245 | | | | | 250 | | | | | 255 | | |
| atg | tat | ccc | atg | agt | gaa | cac | ttt | ttc | aca | ctt | ttg | gaa | gaa | atg | ggt | 816 |
| Met | Tyr | Pro | Met | Ser | Glu | His | Phe | Phe | Thr | Leu | Leu | Glu | Glu | Met | Gly | |
| | | | 260 | | | | | 265 | | | | | 270 | | | |
| tat | ttg | cat | cta | caa | gct | acc | aaa | cca | gat | aca | gtg | ggc | gtt | gct | tta | 864 |
| Tyr | Leu | His | Leu | Gln | Ala | Thr | Lys | Pro | Asp | Thr | Val | Gly | Val | Ala | Leu | |
| | | 275 | | | | | 280 | | | | | 285 | | | | |
| aga | gat | tca | cca | gct | ggt | tta | gca | gct | tat | att | ttg | gag | aaa | ttt | tca | 912 |
| Arg | Asp | Ser | Pro | Ala | Gly | Leu | Ala | Ala | Tyr | Ile | Leu | Glu | Lys | Phe | Ser | |

```
        290                 295                 300
aca tgg act aac aga tct tgg agg tca gtt aaa gat gga aac ttg ctg      960
Thr Trp Thr Asn Arg Ser Trp Arg Ser Val Lys Asp Gly Asn Leu Leu
305                 310                 315                 320 tta aaa tac aat att cct gaa ctt tta gac aat gtc atg ata tac tac     1008
Leu Lys Tyr Asn Ile Pro Glu Leu Leu Asp Asn Val Met Ile Tyr Tyr
                325                 330                 335 gtt act gat tcc att act act tca atg aga tta tat gca gaa tca ttc     1056
Val Thr Asp Ser Ile Thr Thr Ser Met Arg Leu Tyr Ala Glu Ser Phe
            340                 345                 350 aca aaa gca cac ctt gct ttg aac tta gat agg gtg cgc aat cat gtc     1104
Thr Lys Ala His Leu Ala Leu Asn Leu Asp Arg Val Arg Asn His Val
        355                 360                 365 cca gca gcc tgc gca aaa ttt cca aac gag ttg gct tat gtg acc gat     1152
Pro Ala Ala Cys Ala Lys Phe Pro Asn Glu Leu Ala Tyr Val Thr Asp
370                 375                 380 tgc caa ctt gct gag aaa tat aaa act tta ttg cag tcc aat gac atg     1200
Cys Gln Leu Ala Glu Lys Tyr Lys Thr Leu Leu Gln Ser Asn Asp Met
385                 390                 395                 400 cca agt ggt ggc cat ttt gca gca ttt gag gaa cct ggt ctt tta gca     1248
Pro Ser Gly Gly His Phe Ala Ala Phe Glu Glu Pro Gly Leu Leu Ala
                405                 410                 415 gaa gac att ttc act gcg gtg aaa aag ttt aaa gaa ttt tat tcc aaa     1296
Glu Asp Ile Phe Thr Ala Val Lys Lys Phe Lys Glu Phe Tyr Ser Lys
            420                 425                 430 aaa gct gaa agc caa aag aaa gct gat ttg                             1326
Lys Ala Glu Ser Gln Lys Lys Ala Asp Leu
        435                 440

<210> SEQ ID NO 33
<211> LENGTH: 442
<212> TYPE: PRT
<213> ORGANISM: Ctenocephalides felis

<400> SEQUENCE: 33

Ile Thr Lys Glu Leu Pro Lys Pro Asn Ile Pro Leu Asp Thr Trp Trp
1               5                   10                  15

Gly Pro Gly Lys Pro Gln Asn Val Asp Ile Ser Ile Arg Pro Phe Lys
                20                  25                  30

Ile Asn Ile Asn Asn Lys Val Ile Glu Asn Leu Lys Leu Lys Leu Asn
            35                  40                  45

Asp Val Gln Tyr Thr Leu Pro Leu Glu Gly Ile Asn Phe Glu Tyr Gly
        50                  55                  60

Phe Asn Thr Asp Ser Leu Lys Lys Ile Val Asp Phe Trp Arg Thr Gln
65                  70                  75                  80

Tyr Asn Trp Arg Glu Arg Glu Ala Leu Leu Asn Lys Tyr Pro His Phe
                85                  90                  95

Lys Thr Asn Ile Gln Gly Leu Asp Ile His Tyr Val His Ile Lys Pro
            100                 105                 110

Gln Val Ser Lys Asn Ile Glu Val Leu Pro Leu Val Met Ile His Gly
        115                 120                 125

Trp Pro Gly Ser Phe Val Glu Phe Tyr Lys Ile Ile Pro Met Leu Thr
    130                 135                 140

Thr Pro Arg Ala Gly Tyr Asn Phe Val Phe Glu Leu Ile Leu Pro Ser
145                 150                 155                 160

Ile Pro Gly Tyr Gly Phe Ser Gln Ala Ala Ala Lys Pro Gly Leu Gly
                165                 170                 175
```

```
Ser Thr Gln Val Ala Val Ile Met Arg Asn Leu Met Glu Arg Ile Gly
            180                 185                 190

Phe Lys Lys Tyr Tyr Val Gln Gly Gly Asp Trp Gly Ser Met Ile Ile
            195                 200                 205

Ser Ala Met Ser Thr Leu Phe Pro Glu Asn Val Leu Gly Gln His Ser
            210                 215                 220

Asn Met Cys Phe Val Asn Thr Pro Ser Ser Asn Ile Lys Ala Ile Ile
225                 230                 235                 240

Gly Ser Phe Phe Pro Glu Ser Phe Ala Gly Thr Gly Asn Ala His Lys
                    245                 250                 255

Met Tyr Pro Met Ser Glu His Phe Phe Thr Leu Leu Glu Glu Met Gly
            260                 265                 270

Tyr Leu His Leu Gln Ala Thr Lys Pro Asp Thr Val Gly Val Ala Leu
            275                 280                 285

Arg Asp Ser Pro Ala Gly Leu Ala Ala Tyr Ile Leu Glu Lys Phe Ser
            290                 295                 300

Thr Trp Thr Asn Arg Ser Trp Arg Ser Val Lys Asp Gly Asn Leu Leu
305                 310                 315                 320

Leu Lys Tyr Asn Ile Pro Glu Leu Leu Asp Asn Val Met Ile Tyr Tyr
                    325                 330                 335

Val Thr Asp Ser Ile Thr Thr Ser Met Arg Leu Tyr Ala Glu Ser Phe
            340                 345                 350

Thr Lys Ala His Leu Ala Leu Asn Leu Asp Arg Val Arg Asn His Val
            355                 360                 365

Pro Ala Ala Cys Ala Lys Phe Pro Asn Glu Leu Ala Tyr Val Thr Asp
            370                 375                 380

Cys Gln Leu Ala Glu Lys Tyr Lys Thr Leu Leu Gln Ser Asn Asp Met
385                 390                 395                 400

Pro Ser Gly Gly His Phe Ala Ala Phe Glu Glu Pro Gly Leu Leu Ala
                    405                 410                 415

Glu Asp Ile Phe Thr Ala Val Lys Lys Phe Lys Glu Phe Tyr Ser Lys
            420                 425                 430

Lys Ala Glu Ser Gln Lys Lys Ala Asp Leu
            435                 440

<210> SEQ ID NO 34
<211> LENGTH: 1326
<212> TYPE: DNA
<213> ORGANISM: Ctenocephalides felis

<400> SEQUENCE: 34
caaatcagct ttcttttggc tttcagcttt tttggaataa aattctttaa acttttcac      60 cgcagtgaaa atgtcttctg ctaaaagacc aggttcctca aatgctgcaa atggccacc    120 acttggcatg tcattggact gcaataaagt tttatatttc tcagcaagtt ggcaatcggt    180
cacataagcc aactcgtttg gaattttgc gcaggctgct gggacatgat tgcgcaccct    240
atctaagttc aaagcaaggt gtgcttttgt gaatgattct gcatataatc tcattgaagt    300
agtaatggaa tcagtaacgt agtatatcat gacattgtct aaaagttcag gaatattgta    360
ttttaacagc aagtttccat ctttaactga cctccaagat ctgttagtcc atgttgaaaa    420
tttctccaaa atataagctg ctaaaccagc tggtgaatct cttaaagcaa cgcccactgt    480
atctggtttg gtagcttgta gatgcaaata acccatttct tccaaaagtg tgaaaaagtg    540
ttcactcatg ggatacattt tatgcgcatt tcccgtgcca gcaaacgatt ccgggaaaaa    600
```

-continued

```
gcttccaatt atagccttga tatttgatga tggagtattg acaaaacaca tgtttgagtg       660
ctgtcccagg acattttctg gaaataatgt tgacatcgcg cttatgatca tagaacccca       720
gtcgcctcct tgtacataat attttttgaa tccaatgcgc tccatcaaat tgcgcattat       780
aacggcgacc tgagtcgatc caagaccagg tttagctgca gcctgtgaaa agccgtatcc       840
aggaatacta ggcaatatca attcgaatac gaaattgtaa cctgctcttg gagttgtcaa       900
cataggtatg atcttgtaga attccacaaa agatcctggc caaccatgga tcattaccaa       960
aggcaaaact tcaatatttt tagagacctg tggttttatg tggacataat gaatatccag      1020
gccttgaata tttgttttga agtgtggata tttatttaat aatgcttcac gttcacgcca      1080
attatattga gttcgccaaa aatctacaat cttttttcagg gaatctgtat tgaaaccata     1140
ttcaaaattg atgccctcta aaggtaaagt atattgaaca tcattgagtt ttagtttcag      1200
attttcaatc actttgttat taatattaat tttaaacggt cttattgata tgtcaacatt      1260
ttgtggcttt cctggacccc accaagtgtc gagaggtata tttggttttg gaagttcttt      1320
cgtaat                                                                 1326
```

<210> SEQ ID NO 35
<211> LENGTH: 1284
<212> TYPE: DNA
<213> ORGANISM: Ctenocephalides felis

<400> SEQUENCE: 35

```
ctttcagctt ttttggaata aaattcttta aacttttca ccgcagtgaa aatgtcttct         60
gctaaaagac caggttcctc aaatgctgca aaatggccac cacttggcat gtcattggac       120
tgcaataaag ttttatattt ctcagcaagt tggcaatcgg tcacataagc caactcgttt       180
ggaaattttg cgcaggctgc tgggacatga ttgcgcaccc tatctaagtt caaagcaagg       240
tgtgcttttg tgaatgattc tgcatataat ctcattgaag tagtaatgga atcagtaacg       300
tagtatatca tgacattgtc taaaagttca ggaatattgt attttaacag caagtttcca       360
tctttaactg acctccaaga tctgttagtc catgttgaaa attctccaa aatataagct        420 gctaaaccag ctggtgaatc tcttaaagca acgcccactg tatctggttt ggtagcttgt      480
agatgcaaat aacccatttc ttccaaaagt gtgaaaaagt gttcactcat gggatacatt       540
ttatgcgcat ttcccgtgcc agcaaacgat tccgggaaaa agcttccaat tatagccttg       600
atatttgatg atggagtatt gacaaaacac atgtttgagt gctgtcccag gacattttct       660
ggaaataatg ttgacatcgc gcttatgatc atagaacccc agtcgcctcc ttgtacataa       720
tattttttga atccaatgcg ctccatcaaa ttgcgcatta taacggcgac ctgagtcgat       780
ccaagaccag gtttagctgc agcctgtgaa aagccgtatc caggaatact aggcaatatc       840
aattcgaata cgaaattgta acctgctctt ggagttgtca acataggtat gatcttgtag       900
aattccacaa agatcctggc caaccatgg atcattacca aaggcaaaac ttcaatatttt      960 ttagagacct gtggttttat gtggacataa tgaatatcca ggccttgaat atttgttttg      1020
aagtgtggat atttatttaa taatgcttca cgttcacgcc aattatattg agttcgccaa     1080
aaatctacaa tcttttttcag ggaatctgta ttgaaaccat attcaaaatt gatgccctct    1140
aaaggtaaag tatattgaac atcattgagt tttagtttca gattttcaat cactttgtta     1200
ttaatattaa ttttaaacgg tcttattgat atgtcaacat tttgtggctt tcctggaccc     1260
caccaagtgt cgagaggtat attt                                            1284
```

FLEA EPOXIDE HYDROLASE PROTEINS AND USES THEREOF

CROSS-REFERENCE TO RELATED APPLICATIONS

The present application is a divisional application of pending U.S. patent application Ser. No. 09/182,816, filed Oct. 29, 1998, which is a continuation-in-part of U.S. patent application Ser. No. 08/989,510, filed Dec. 12, 1997, now U.S. Pat. No. 6,037,160 each entitled "NOVEL FLEA EPOXIDE HYDROLASE NUCLEIC ACID MOLECULES, PROTEINS AND USES THEREOF", each of which is incorporated herein by this reference in its entirety.

FIELD OF THE INVENTION

The present invention relates to flea epoxide hydrolase nucleic acid molecules, proteins encoded by such nucleic acid molecules, antibodies raised against such proteins, and inhibitors of such proteins. The present invention also includes therapeutic compositions comprising such nucleic acid molecules, proteins, antibodies, and/or other inhibitors, as well as their use to protect an animal from hematophagous arthropod infestation.

BACKGROUND OF THE INVENTION

Hematophagous arthropod infestation of animals is a health and economic concern because hematophagous arthropods are known to cause and/or transmit a variety of diseases. Hematophagous arthropods directly cause a variety of diseases, including allergies, and also carry a variety of infectious agents including, but not limited to, endoparasites (e.g., nematodes, cestodes, trematodes and protozoa), bacteria and viruses. In particular, the bites of hematophagous arthropods are a problem for animals maintained as pets because the infestation becomes a source of annoyance not only for the pet but also for the pet owner who may find his or her home generally contaminated with insects. As such, hematophagous arthropods are a problem not only when they are on an animal but also when they are in the general environment of the animal.

Bites from hematophagous arthropods are a particular problem because they not only can lead to disease transmission but also can cause a hypersensitive response in animals which is manifested as disease. For example, bites from fleas can cause an allergic disease called flea allergic (or allergy) dermatitis (FAD). A hypersensitive response in animals typically results in localized tissue inflammation and damage, causing substantial discomfort to the animal.

The medical importance of arthropod infestation has prompted the development of reagents capable of controlling arthropod infestation. Commonly encountered methods to control arthropod infestation are generally focused on use of insecticides. While some of these products are efficacious, most, at best, offer protection of a very limited duration. Furthermore, many of the methods are often not successful in reducing arthropod populations. In particular, insecticides have been used to prevent hematophagous arthropod infestation of animals by adding such insecticides to shampoos, powders, collars, sprays, foggers and liquid bath treatments (i.e., dips). Reduction of hematophagous arthropod infestation on the pet has been unsuccessful for one or more of the following reasons: (1) failure of owner compliance (frequent administration is required); (2) behavioral or physiological intolerance of the pet to the pesticide product or means of administration; and (3) the emergence of hematophagous arthropod populations resistant to the prescribed dose of pesticide. Hematophagous arthropod populations, however, have been found to become resistant to insecticides.

Juvenile hormone (JH) regulates growth and development of immature insects, and is involved in reproductive processes in adult insects. JH levels are controlled by two degradative enzymes, juvenile hormone esterase and juvenile hormone epoxide hydrolase.

Prior investigators have described insect juvenile hormone epoxide hydrolase (JHEH) protein biochemistry, for example, Touhara et al., *J. Biol. Chem.*, 268:19604–19609, 1993 and Khlebodarova et al., *Insect Biochem. Molec Biol*, 26:829–835, 1996. Prior investigators have described certain insect epoxide hydrolase (EH) nucleic acid and amino acid sequences, for example, Wojtasek et al., *Biochem. Biophys. Res. Comm.*, 220:323–329, 1996 describes *Manduca sexta* JHEH sequences and Roe et al., *Arch. Insect Biochem. Physiol.*, 32:527–535, 1996. Mammalian EH genes have been cloned, none of which have more than 40% identity with the nucleic acid molecules of the present invention.

Identification of an EH of the present invention is unexpected, however, because even the most similar nucleic acid sequence identified by previous investigators could not be used to identify an EH of the present invention. In addition, identification of an EH protein of the present invention is unexpected because the inventors of the present invention identified highly conserved regions of epoxide hydrolase sequences suitable for the production of degenerate primers. Production of primers to such conserved regions is not taught or suggested by previous investigators.

In summary, there remains a need to develop a reagent and a method to protect animals from hematophagous arthropod infestation.

SUMMARY OF THE INVENTION

The present invention relates to a novel product and process for protection of animals from arthropod infestation. According to the present invention there are provided arthropod epoxide hydrolase (EH) proteins and mimetopes thereof; arthropod nucleic acid molecules, including those that encode such proteins; antibodies raised against such EH proteins (i.e., anti-arthropod EH antibodies); and compounds that inhibit arthropod EH activity (i.e., inhibitory compounds or inhibitors).

The present invention also includes methods to obtain such proteins, mimetopes, nucleic acid molecules, antibodies and inhibitory compounds. Also included in the present invention are therapeutic compositions comprising such proteins, mimetopes, nucleic acid molecules, antibodies, and/or inhibitory compounds, as well as use of such therapeutic compositions to protect animals from arthropod infestation.

Identification of an EH of the present invention is unexpected, however, because the most similar nucleic acid sequence identified by previous investigators could not be used to identify an EH of the present invention. In addition, identification of an EH protein of the present invention is unexpected because the inventors of the present invention identified highly conserved regions of epoxide hydrolase sequences suitable for the production of degenerate primers. Production of primers to such conserved regions is not taught or suggested by previous investigators.

One embodiment of the present invention is an isolated nucleic acid molecule that hybridizes under stringent hybridization conditions with a gene comprising a nucleic acid sequence including SEQ ID NO:4, SEQ ID NO:6, SEQ ID NO:7, SEQ ID NO:9, SEQ ID NO:10, SEQ ID NO:12, SEQ ID NO:15, SEQ ID NO:19, SEQ ID NO:21, SEQ ID NO:22, SEQ ID NO:24, SEQ ID NO:25, SEQ ID NO:26 and/or SEQ ID NO:27.

The present invention also includes a nucleic acid molecule that hybridizes under stringent hybridization conditions with a complement of a nucleic acid molecule encoding a protein comprising at least one of the following amino acid sequences: SEQ ID NO:5, SEQ ID NO:8, SEQ ID NO:11, SEQ ID NO:20, SEQ ID NO:23 and/or SEQ ID NO:28. A preferred nucleic acid molecule of the present invention includes a nucleic acid molecule comprising a nucleic acid sequence including SEQ ID NO:4, SEQ ID NO:6, SEQ ID NO:7, SEQ ID NO:9, SEQ ID NO:10, SEQ ID NO:12, SEQ ID NO:15, SEQ ID NO:19, SEQ ID NO:21, SEQ ID NO:22, SEQ ID NO:24, SEQ ID NO:25, SEQ ID NO:26 and/or SEQ ID NO:27, and an allelic variant of a nucleic acid molecule comprising any of the nucleic acid sequences.

The present invention also relates to recombinant molecules, recombinant viruses and recombinant cells that include a nucleic acid molecule of the present invention. Also included are methods to produce such nucleic acid molecules, recombinant molecules, recombinant viruses and recombinant cells.

The present invention also relates to mimetopes of arthropod EH proteins as well as to isolated antibodies that selectively bind to arthropod EH proteins or mimetopes thereof. Also included are methods, including recombinant methods, to produce proteins, mimetopes and antibodies of the present invention.

Another embodiment of the present invention is a method to identify a compound capable of inhibiting arthropod EH activity, the method comprising: (a) contacting an isolated hematophagous arthropod EH with a putative inhibitory compound under conditions in which, in the absence of the compound, the protein has EH activity; and (b) determining if the putative inhibitory compound inhibits the activity. Also included in the present invention is a test kit to identify a compound capable of inhibiting hematophagous arthropod EH activity, the test kit comprising an isolated hematophagous arthropod EH protein having EH activity and a means for determining the extent of inhibition of the activity in the presence of a putative inhibitory compound.

Yet another embodiment of the present invention is a therapeutic composition that is capable of reducing hematophagous ectoparasite infestation. Such a therapeutic composition includes at least one of the following protective compounds: an isolated hematophagous arthropod EH protein or a mimetope thereof, an isolated EH nucleic acid molecule that hybridizes under stringent hybridization conditions with a *Ctenocephalides felis* EH gene, an isolated antibody that selectively binds to a hematophagous arthropod EH protein, and an inhibitor of EH activity identified by its ability to inhibit the activity of a hematophagous arthropod EH. A therapeutic composition of the present invention can also include an excipient, an adjuvant and/or a carrier. Preferred EH nucleic acid molecule compounds of the present invention include naked nucleic acid vaccines, recombinant virus vaccines and recombinant cell vaccines. Also included in the present invention is a method to protect an animal from hematophagous ectoparasite infestation, comprising the step of administering to the animal a therapeutic composition of the present invention.

DETAILED DESCRIPTION OF THE INVENTION

The present invention provides for isolated arthropod epoxide hydrolase (EH) proteins, isolated arthropod EH nucleic acid molecules, antibodies directed against arthropod EH proteins and other inhibitors of arthropod EH activity. As used herein, the terms isolated arthropod EH proteins and isolated arthropod EH nucleic acid molecules refers to EH proteins and EH nucleic acid molecules derived from arthropods and, as such, can be obtained from their natural source or can be produced using, for example, recombinant nucleic acid technology or chemical synthesis. Also included in the present invention is the use of these proteins, nucleic acid molecules, antibodies and inhibitors as therapeutic compositions to protect animals from hematophagous ectoparasite infestation as well as in other applications, such as those disclosed below.

Arthropod EH proteins and nucleic acid molecules of the present invention have utility because they represent novel targets for anti-arthropod vaccines and drugs. The products and processes of the present invention are advantageous because they enable the inhibition of arthropod development, metamorphosis, feeding, digestion and reproduction processes that involve EH proteins. While not being bound by theory, it is believed that expression of arthropod EH proteins are developmentally regulated, thereby suggesting that EH proteins are involved in arthropod development and/or reproduction. The present invention is particularly advantageous because the proteins of the present invention were identified in larval fleas, thereby suggesting the importance of the proteins as developmental proteins.

According to the present invention, epoxide hydrolases include enzymes capable of hydrolyzing exogenous or endogenous epoxides to their corresponding diols. For example, juvenile hormone epoxide hydrolase (JHEH) can be characterized by its ability to hydrate the epoxide ring of juvenile hormone (JH) to yield JH diol.

Figure 1:
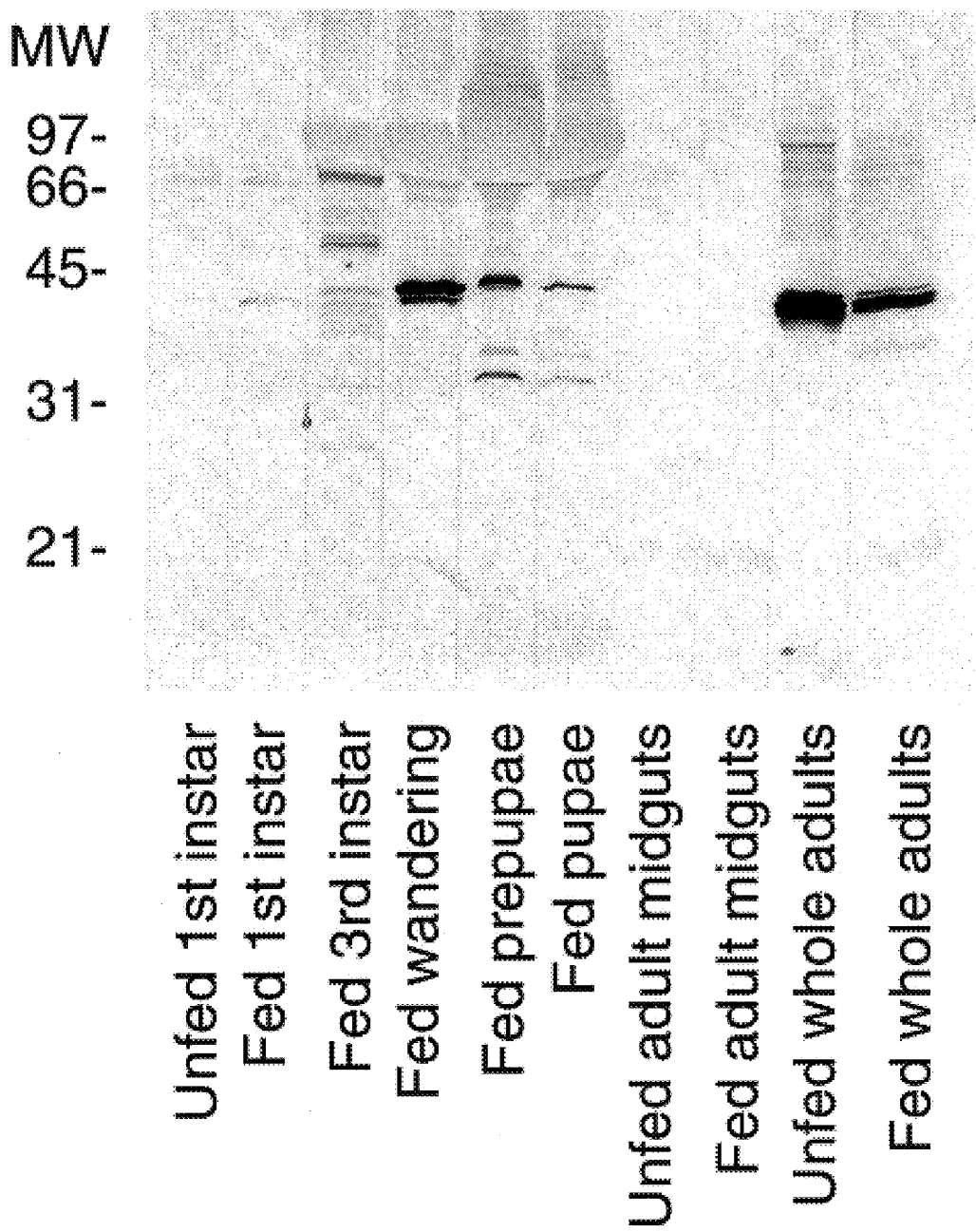
FIG. 1 illustrates epoxide hydrolase proteins in different flea tissues using an anti-epoxide hydrolase polyclonal antiserum.

One embodiment of the present invention is an EH formulation that comprises one or more hydrolase proteins that range in molecular weight from about 10 kilodaltons (kD) to about 120 kD, more preferably from about 20 kD to about 110 kD, and even more preferably from about 25 kD to about 100 kD, as determined by SDS-PAGE (sodium dodecyl sulfate polyacrylamide gel electrophoresis) and identified using a polyclonal anti-EH1 antiserum (the production of which is described in detail in Example 3). An even more preferred formulation includes one or more flea EH proteins having migration patterns as shown in FIG. 1.

Tissue can be obtained from unfed fleas or from fleas that recently consumed a blood meal (i.e., blood-fed fleas). Such flea tissues are referred to herein as, respectively, unfed flea and fed flea tissue. Preferred flea tissue from which to obtain an EH formulation of the present invention include, but are not limited to, unfed or fed $1^{st}$ instar larvae; fed $3^{rd}$ instar larvae, fed wandering larvae, fed prepupal larvae, fed pupae and whole unfed or fed adult fleas. Preferred flea tissue from which to obtain an EH formulation of the present invention includes third instar larvae, wandering larvae, prepupal larvae, pupae, and adult fleas.

In a preferred embodiment, an EH formulation of the present invention comprises a flea protein comprising amino acid sequence SEQ ID NO:5, SEQ ID NO:8, SEQ ID NO:11, SEQ ID NO:20, SEQ ID NO:23 and/or SEQ ID NO:28.

Suitable arthropods from which to isolate an EH formulation of the present invention include, but are not limited to agricultural pests, stored product pests, forest pests, structural pests or animal health pests. Suitable agricultural pests of the present invention include, but are not limited to Colorado potato beetles, corn earworms, fleahoppers, weevils, pink boll worms, cotton aphids, beet armyworms, lygus bugs, hessian flies, sod webworms, whites grubs, diamond back moths, white flies, planthoppers, leafhoppers, mealy bugs, mormon crickets and mole crickets. Suitable stored product pests of the present invention include, but are not limited to dermestids, anobeids, saw toothed grain beetles, indian mealmoths, flour beetles, long-horn wood boring beetles and metallic wood boring beetles. Suitable forest pests of the present invention include, but are not limited to southern pine bark bettles, gypsy moths, elm beetles, ambrosia bettles, bag worms, tent worms and tussock moths. Suitable structural pests of the present invention include, but are not limited to, bess beetles, termites, fire ants, carpenter ants, wasps, hornets, cockroaches, silverfish, *Musca domestica* and *Musca autumnalis*. Suitable animal health pests of the present invention include, but are not limited to fleas, ticks, mosquitoes, black flies, lice, true bugs, sand flies, Psychodidae, tsetse flies, sheep blow flies, cattle grub, mites, horn flies, heel flies, deer flies, Culicoides and warble flies. Preferred arthropods from which to isolate an EH formulation of the present invention include fleas, midges, mosquitos, sand flies, black flies, horse flies, snipe flies, louse flies, horn flies, deer flies, tsetse flies, buffalo flies, blow flies, stable flies, myiasis-causing flies, biting gnats, lice, mites, bee, wasps, ants, true bugs and ticks, preferably fleas, ticks and blow flies, and more preferably fleas. Preferred fleas from which to isolate EH proteins include Ctenocephalides, Ceratophyllus, Diamanus, Echidnophaga, Nosopsyllus, Pulex, Tunga, Oropsylla, Orchopeus and Xenopsylla. More preferred fleas include *Ctenocephalides felis, Ctenocephalides canis, Ceratophyllus pulicidae, Pulex irritans, Oropsylla (Thrassis) bacchi, Oropsylla (Diamanus) montana, Orchopeus howardi, Xenopsylla cheopis* and *Pulex similans*, with *C. felis* being even more preferred.

Suitable tissue from which to isolate an EH formulation of the present invention includes unfed fleas or fleas that recently consumed a blood meal (i.e., blood-fed fleas). Such flea tissues are referred to herein as, respectively, unfed flea and fed flea tissue. Preferred flea tissue from which to obtain an EH formulation of the present invention includes unfed or fed $1^{st}$ instar larvae; fed $3^{rd}$ instar larvae, fed wandering larvae, fed prepupal larvae, fed pupae and whole unfed or fed adult fleas, with third instar larvae, wandering larvae, prepupal larvae, pupae, and adult fleas being more preferred.

Another embodiment of the present invention is an isolated protein comprising an arthropod EH protein. It is to be noted that the term "a" or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology or can be produced by chemical synthesis.

As used herein, an isolated arthropod EH protein can be a full-length protein or any homolog of such a protein. As used herein, a protein can be a polypeptide or a peptide, as the terms are used by those of skill in the art. An isolated protein of the present invention, including a homolog, can be identified in a straight-forward manner by the protein's ability to elicit an immune response against arthropod EH proteins; to hydrate octene 1,2-oxide, cis-stilbene oxide, trans-stilbene oxide, styrene oxide, 4-nitrostyrene oxide, trans-β-ethylstyrene oxide, phenanthrene 9,10-oxide, benzo (a)pyrene 4,5-oxide, 1,2,3,4,9,9-hexachloro-6,7-epoxy-1,4, 4a,5,6,7,8,8a-octahydro-1,4-endo-methano-napthalene, squalene 2,3-oxide, cholesterol-5α, 6α-oxide, p-nitrophenyl glycidyl ether, or 1-(4'-ethylphenoxy)-3,7-dimethyl-6,7-epoxy-2E-octene (generally described in Wixtrom et al., in *Biochemical Pharmacology and Toxicology*, vol. 1 Methodological Aspects of Drug Metabolizing Enzymes, pp. 1–93, (Zakim and Vessey, eds.), John Wiley & Sons, New York, 1985; which is incorporated herein in its entirety by this reference) or the epoxide ring of juvenile hormone; or to bind to the photoaffinity labels $^{3}$H-epoxyhomofarnesyl diazoacetate ($^{3}$H-EHDA), $^{3}$H-epoxybishomofarnesyl diazoacetate ($^{3}$H-EBDA), or $^{3}$H-epoxyfarnesyl diazoacetate ($^{3}$H-EFDA) (generally described in Touhara et al., *J. Biol. Chem.*, vol. 268, pp. 19604–19609, 1993; which is incorporated herein in its entirety by this reference). EH proteins of the present invention include JHEH proteins. As such, an EH protein of the present invention can comprise a protein capable of hydrating octene 1,2-oxide, cis-stilbene oxide, trans-stilbene oxide, styrene oxide, 4-nitrostyrene oxide, trans-β-ethylstyrene oxide, phenanthrene 9,10-oxide, benzo (a)pyrene 4,5-oxide, 1,2,3,4,9,9-hexachloro-6,7-epoxy-1,4, 4a,5,6,7,8,8a-octahydro-1,4-endo-methano-napthalene, squalene 2,3-oxide, cholesterol-5α, 6α-oxide, p-nitrophenyl glycidyl ether, or 1-(4'-ethylphenoxy)-3,7-dimethyl-6,7-epoxy-2E-octene, or the epoxide ring of juvenile hormone, and/or bind to the photoaffinity labels $^{3}$H-epoxyhomofarnesyl diazoacetate ($^{3}$H-EHDA), $^{3}$H-epoxybishomofarnesyl diazoacetate ($^{3}$H-EBDA), or $^{3}$H-epoxyfarnesyl diazoacetate ($^{3}$H-EFDA). Examples of EH homologs include EH proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog includes at least one epitope capable of eliciting an immune response against an arthropod EH protein. That is, when the homolog is administered to an animal as an immunogen, using techniques known to those skilled in the art, the animal will produce an immune response against at least one epitope of a natural arthropod EH protein. The ability of a protein to effect an immune response, can be measured using techniques known to those skilled in the art. EH protein homologs of the present invention also include EH proteins that hydrate octene 1,2-oxide, cis-stilbene oxide, trans-stilbene oxide, styrene oxide, 4-nitrostyrene oxide, trans-β-ethylstyrene oxide, phenanthrene 9,10-oxide, benzo(a)pyrene 4,5-oxide, 1,2,3,4,9,9-hexachloro-6,7-epoxy-1,4,4a,5,6,7,8,8a-octahydro-1,4-endo-methano-napthalene, squalene 2,3-oxide, cholesterol-5α, 6α-oxide, p-nitrophenyl glycidyl ether, or 1-(4'-ethylphenoxy)-3,7-dimethyl-6,7-epoxy-2E-octene, or the epoxide ring of juvenile hormone, and/or bind to the photoaffinity labels $^3$H-epoxyhomofarnesyl diazoacetate ($^3$H-EHDA), $^3$H-epoxybishomofarnesyl diazoacetate ($^3$H-EBDA), or $^3$H-epoxyfarnesyl diazoacetate ($^3$H-EFDA).

Arthropod EH protein homologs can be the result of natural allelic variation or natural mutation. EH protein homologs of the present invention can also be produced using techniques known in the art including, but not limited to, direct modifications to the protein or modifications to the gene encoding the protein using, for example, classic or recombinant nucleic acid techniques to effect random or targeted mutagenesis.

Isolated EH proteins of the present invention have the further characteristic of being encoded by nucleic acid molecules that hybridize under stringent hybridization conditions to a gene encoding a *Ctenocephalides felis* EH protein (i.e., a *C. felis* EH gene). Stringent hybridization conditions are determined based on defined physical properties of the gene to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, *Molecular Cloning: A Laboratory Manual*, Cold Spring Harbor Labs Press, and Meinkoth, et al., 1984, *Anal. Biochem*. 138, 267–284, each of which is incorporated by reference herein in its entirety. As explained in detail in the cited references, the determination of hybridization conditions involves the manipulation of a set of variables including the ionic strength (M, in moles/liter), the hybridization temperature (° C.), the concentration of nucleic acid helix destabilizing agents (such as formamide), the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarity between the two strands:

$$T_m=81.5°\ C.+16.6\ \log M+0.41(\%\ G+C)-500/n-0.61(\%\ \text{formamide}).$$

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation: $T_d=4(G+C)+2(A+T)$. A temperature of 5° C. below $T_d$ is used to detect hybridization between perfectly matched molecules.

Also well known to those skilled in the art is how base-pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base-pairs for hybrids greater than about 150 bp, and $T_d$ decreases about 5° C. for each mismatched base-pair for hybrids below about 50 bp. Conditions for hybrids between about 50 and about 150 base-pairs can be determined empirically and without undue experimentation using standard laboratory procedures well known to those skilled in the art. These simple procedures allow one skilled in the art to set the hybridization conditions (by altering, for example, the salt concentration, the formamide concentration or the temperature) so that only nucleic acid hybrids with less than a specified % base-pair mismatch will hybridize. Stringent hybridization conditions are commonly understood by those skilled in the art to be those experimental conditions that will allow hybridization between molecules having about 30% or less base-pair mismatch (i.e., about 70% or greater identity). Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene under stringent hybridization conditions and similarly whether the nucleic acid molecule will hybridize under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

For example, if the skilled artisan wished to identify a nucleic acid molecule that hybridizes under stringent hybridization conditions with a *Ctenocephalides felis* nucleic acid molecule of about 150 bp in length, the following conditions could preferably be used. The average G+C content of *Ctenocephalides felis* DNA is about 43%. The unknown nucleic acid molecules would be attached to a support membrane, and the 150 bp probe would be labeled, e.g. with a radioactive tag. The hybridization reaction could be carried out in a solution comprising 2×SSC and 0% formamide, at a temperature of about 37° C. (low stringency conditions). Solutions of differing concentrations of SSC can be made by one of skill in the art by diluting a stock solution of 20×SSC (175.3 gram NaCl and about 88.2 gram sodium citrate in 1 liter of water, pH 7) to obtain the desired concentration of SSC. In order to achieve high stringency hybridization, the skilled artisan would calculate the washing conditions required to allow up to 30% base-pair mismatch. For example, in a wash solution comprising 1×SSC and 0% formamide, the $T_m$ of perfect hybrids would be about 82° C.:

$$81.5° C.+16.6 \log (0.15M)+(0.43\times39)-(500/150)-(0.61\times0)=81.7° C.$$

Thus, to achieve hybridization with nucleic acid molecules having about 30% base-pair mismatch, hybridization washes would be carried out at a temperature of about 52° C. It is thus within the skill of one in the art to calculate additional hybridization temperatures based on the desired percentage base-pair mismatch, formulae and G/C content disclosed herein. For example, it is appreciated by one skilled in the art that as the nucleic acid molecule to be tested for hybridization against nucleic acid molecules of the present invention having sequences specified herein becomes longer than 150 nucleotides, the $T_m$ for a hybridization reaction allowing up to 30% base-pair mismatch will not vary significantly from 52° C.

Furthermore, it is known in the art that there are commercially available computer programs for determining the degree of similarity between two nucleic acid sequences. These computer programs include various known methods to determine the percentage identity and the number and length of gaps between hybrid nucleic acid molecules. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, GCG™ (available from Genetics Computer Group, Madison, Wis.), DNAsis™ (available from Hitachi Software, San Bruno, Calif.) and MacVector™ (available from the Eastman Kodak Company, New Haven, Conn.). A preferred method to determine percent identity among amino acid sequences and also among nucleic acid sequences includes using the Compare function by maximum matching within the program DNAsis Version 2.1 using default parameters.

As used herein, a *C. felis* EH gene includes all nucleic acid sequences related to a natural *C. felis* EH gene such as regulatory regions that control production of the *C. felis* EH protein encoded by that gene (such as, but not limited to, transcription, translation or post-translation control regions) as well as the coding region itself. In one embodiment, a *C. felis* EH gene of the present invention includes the nucleic acid sequence SEQ ID NO:4, SEQ ID NO:6, SEQ ID NO:7, SEQ ID NO:9, SEQ ID NO:10, SEQ ID NO:12, SEQ ID NO:15, SEQ ID NO:19, SEQ ID NO:21, SEQ ID NO:22, SEQ ID NO:24, SEQ ID NO:25, SEQ ID NO:26 and/or SEQ ID NO:27. Nucleic acid sequence SEQ ID NO:4 represents the deduced sequence of the coding strand of a PCR amplified nucleic acid molecule denoted herein as nfEH1$_{211}$, the production of which is disclosed in the Examples. The complement of SEQ ID NO:4 (represented herein by SEQ ID NO:6) refers to the nucleic acid sequence of the strand complementary to the strand having SEQ ID NO:4, which can easily be determined by those skilled in the art. Likewise, a nucleic acid sequence complement of any nucleic acid sequence of the present invention refers to the nucleic acid sequence of the nucleic acid strand that is complementary to (i.e., can form a complete double helix with) the strand for which the sequence is cited.

Nucleic acid sequence SEQ ID NO:19 represents the deduced sequence of the coding strand of a PCR amplified nucleic acid molecule denoted herein as nfEH2$_{211}$, the production of which is disclosed in the Examples. The complement of SEQ ID NO:19 (represented herein by SEQ ID NO:21) refers to the nucleic acid sequence of the strand complementary to the strand having SEQ ID NO:19, which can easily be determined by those skilled in the art.

Nucleic acid sequence SEQ ID NO:7 represents the deduced sequence of the coding strand of an apparent coding region of a complementary DNA (cDNA) nucleic acid molecule denoted herein as nfEH1$_{1605}$, the production of which is disclosed in the Examples. The complement of SEQ ID NO:7 is represented herein by SEQ ID NO:9.

Nucleic acid sequence SEQ ID NO:22 represents the deduced sequence of the coding strand of an apparent coding region of a complementary DNA (cDNA) nucleic acid molecule denoted herein as nfEH2$_{1736}$, the production of which is disclosed in the Examples. The complement of SEQ ID NO:22 is represented herein by SEQ ID NO:24.

It should be noted that since nucleic acid sequencing technology is not entirely error-free, the nucleic acid sequences and amino acid sequences presented herein represent, respectively, apparent nucleic acid sequences of nucleic acid molecules of the present invention and apparent amino acid sequences of EH proteins of the present invention.

In another embodiment, a *C. felis* EH gene can be an allelic variant that includes a similar but not identical sequence to SEQ ID NO:4, SEQ ID NO:6, SEQ ID NO:7, SEQ ID NO:9, SEQ ID NO:10, SEQ ID NO:12, SEQ ID NO:15, SEQ ID NO:19, SEQ ID NO:21, SEQ ID NO:22, SEQ ID NO:24, SEQ ID NO:25, SEQ ID NO:26 and/or SEQ ID NO:27. An allelic variant of a *C. felis* EH gene is a gene that occurs at essentially the same locus (or loci) in the genome as the gene including SEQ ID NO:4, SEQ ID NO:6, SEQ ID NO:7, SEQ ID NO:9, SEQ ID NO:10, SEQ ID NO:12, SEQ ID NO:15, SEQ ID NO:19, SEQ ID NO:21, SEQ ID NO:22, SEQ ID NO:24, SEQ ID NO:25, SEQ ID NO:26 and/or SEQ ID NO:27, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given arthropod since the genome is diploid and/or among a group of two or more arthropods.

The minimal size of an EH protein homolog of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. As such, the size of the nucleic acid molecule encoding such a protein homolog is dependent on nucleic acid composition and percent homology between the nucleic acid molecule and complementary sequence. It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode an EH protein homolog of the present invention is from about 12 to about 18 nucleotides in length. Thus, the minimal size of an EH protein homolog of the present invention is from about 4 to about 6 amino acids in length. There is no limit, other than a practical limit, on the maximal size of such a nucleic acid molecule in that the nucleic acid molecule can include a portion of a gene, an entire gene, multiple genes, or portions thereof. The preferred size of a protein encoded by a nucleic acid molecule of the present invention depends on whether a full-length, fusion, multivalent, or functional portion of such a protein is desired. Preferably, the preferred size of a protein encoded by a nucleic acid molecule of the present invention is a portion of the protein that induces an immune response which is about 30 amino acids, more preferably about 35 amino acids and even more preferably about 44 amino acids in length.

In one embodiment, an isolated protein of the present invention is a protein encoded by a nucleic acid molecule that hybridizes under stringent hybridization conditions with nucleic acid molecules $nfEH1_{211}$, $nfEH2_{211}$, $nfEH1_{1605}$, $nfEH1_{1350}$, $nfEH1_{1392}$, $nfEH1_{1326}$, $nfEH2_{1736}$, $nfEH2_{1395}$ and/or $nfEH2_{1293}$. In another embodiment, an isolated protein is encoded by a nucleic acid molecule that hybridizes under stringent hybridization conditions with a nucleic acid molecule having nucleic acid sequence SEQ ID NO:6, SEQ ID NO:9, SEQ ID NO:12, SEQ ID NO:21, SEQ ID NO:24 and/or SEQ ID NO:26.

In another embodiment, a preferred arthropod EH protein includes a protein encoded by a nucleic acid molecule which is at least about 50 nucleotides, or about 150 nucleotides, and which hybridizes under conditions which preferably allow about 35% base pair mismatch, more preferably under conditions which allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch, and even more preferably under conditions which allow about 5% base pair mismatch with a nucleic acid molecule selected from the group consisting of SEQ ID NO:6, SEQ ID NO:9, SEQ ID NO:12, SEQ ID NO:21, SEQ ID NO:24 and/or SEQ ID NO:26.

Another embodiment of the present invention includes an arthropod EH protein encoded by a nucleic acid molecule selected from the group consisting of: a nucleic acid molecule comprising at least about 150 nucleotides, wherein said nucleic acid molecule comprising at least about 150 nucleotides hybridizes, in a solution comprising 1×SSC and 0% formamide, at a temperature of about 52° C., to a nucleic acid sequence selected from the group consisting of SEQ ID NO:6, SEQ ID NO:9, SEQ ID NO:12, SEQ ID NO:21, SEQ ID NO:24 and/or SEQ ID NO:26; and a nucleic acid molecule comprising a fragment of any of said nucleic acid molecules comprising at least about 150 nucleotides.

Yet another preferred arthropod EH protein of the present invention includes a protein encoded by a nucleic acid molecule which is preferably about 45% identical, more preferably about 50% identical, more preferably about 55% identical, more preferably about 60% identical, more preferably about 65% identical, more preferably about 70% identical, more preferably about 75% identical, more preferably about 80% identical, more preferably about 85% identical, more preferably about 90% identical and even more preferably about 95% identical to a nucleic acid molecule having the nucleic acid sequence SEQ ID NO:6, SEQ ID NO:9, SEQ ID NO:12, SEQ ID NO:21, SEQ ID NO:24, SEQ ID NO:26, and/or fragments of such proteins. Percent identity as used herein is determined using the Compare function by maximum matching within the program DNAsis Version 2.1 using default parameters.

More preferred arthropod EH proteins of the present invention include proteins comprising amino acid sequences that are at least about 50%, preferably at least about 55%, more preferably at least about 60%, even more preferably at least about 65%, even more preferably at least about 70%, even more preferably at least about 75%, even more preferably at least about 80%, even more preferably at least about 85%, even more preferably at least about 90%, and even more preferably at least about 95%, identical to amino acid sequence SEQ ID NO:5, SEQ ID NO:8, SEQ ID NO:11, SEQ ID NO:20, SEQ ID NO:23 and/or SEQ ID NO:28.

A preferred isolated protein of the present invention is a protein encoded by nucleic acid molecules comprising at least a portion of at least one of the following nucleic acid molecules: $nfEH1_{211}$, $nfEH2_{211}$, $nfEH1_{1605}$, $nfEH1_{1350}$, $nfEH1_{1392}$, $nfEH1_{1326}$, $nfEH2_{1736}$, $nfEH2_{1395}$, $nfEH2_{1293}$ or allelic variants of any of these nucleic acid molecules. Another preferred isolated protein is encoded by a nucleic acid molecule having nucleic acid sequence SEQ ID NO:4, SEQ ID NO:7, SEQ ID NO:10, SEQ ID NO:15, SEQ ID NO:19, SEQ ID NO:22, SEQ ID NO:25 and/or SEQ ID NO:27; or a protein encoded by an allelic variant of any of these listed nucleic acid molecule.

Preferred arthropod EH proteins of the present invention include proteins that are at least about 50%, preferably at least about 55%, more preferably at least about 60%, even more preferably at least about 65%, even more preferably at least about 70%, even more preferably at least about 75%, even more preferably at least about 80%, even more preferably at least about 85%, even more preferably at least about 90%, and even more preferably at least about 95% identical to $PfEH1_{70}$, $PfEH2_{70}$, $PfEH1_{427}$, $PfEH1_{464}$, $PfEH1_{449}$, $PfEH2_{465}$ and/or $PfEH2_{430}$. More preferred is an arthropod EH protein comprising $PfEH1_{70}$, $PfEH2_{70}$, $PfEH1_{427}$, $PlEH1_{464}$, $PfEH1_{449}$, $PfEH2_{465}$ and/or $PfEH2_{430}$; and proteins encoded by allelic variants of nucleic acid molecules encoding proteins $PfEH1_{70}$, $PfEH2_{70}$, $PfEH1_{427}$, $PfEH1_{464}$, $PfEH1_{449}$, $PfEH2_{465}$ and/or $PfEH2_{430}$.

Additional preferred arthropod EH proteins of the present invention include proteins encoded by a nucleic acid molecule comprising at least a portion of $nfEH1_{211}$, $nfEH2_{211}$, $nfEH1_{1605}$, $nfEH1_{1350}$, $nfEH1_{1392}$, $nfEH1_{1326}$, $nfEH2_{1736}$, $nfEH2_{1395}$ and/or $nfEH2_{1293}$, or by an allelic variant of such nucleic acid molecules. Particularly preferred arthropod EH proteins are $PfEH1_{70}$, $PfEH2_{70}$, $PfEH1_{427}$, $PfEH1_{464}$, $PfEH1_{449}$, $PfEH2_{465}$ and/or $PfEH2_{430}$.

In one embodiment, a preferred EH protein of the present invention is encoded by at least a portion of SEQ ID NO:4, SEQ ID NO:7, SEQ ID NO:10, SEQ ID NO:15, SEQ ID NO:19, SEQ ID NO:22, SEQ ID NO:25 and/or SEQ ID NO:27, and, as such, has an amino acid sequence that includes at least a portion of SEQ ID NO:5, SEQ ID NO:8, SEQ ID NO:11, SEQ ID NO:20, SEQ ID NO:23 and/or SEQ ID NO:28. Also preferred is a protein encoded by an allelic variant of a nucleic acid molecule comprising at least a portion of the above-listed nucleic acid sequences.

Additional preferred arthropod EH proteins of the present invention include proteins comprising the amino acid sequence SEQ ID NO:5, SEQ ID NO:8, SEQ ID NO:11, SEQ ID NO:20, SEQ ID NO:23, SEQ ID NO:28, and proteins comprising homologs of a protein having the amino acid sequence SEQ ID NO:5, SEQ ID NO:8, SEQ ID NO:11, SEQ ID NO:20, SEQ ID NO:23 and/or SEQ ID NO:28 in which such a homolog comprises at least one epitope that elicits an immune response against a protein having an amino acid sequence SEQ ID NO:5, SEQ ID NO:8, SEQ ID NO:11, SEQ ID NO:20, SEQ ID NO:23 and/or SEQ ID NO:28. Likewise, also preferred are proteins encoded by nucleic acid molecules having nucleic acid sequence SEQ ID NO:4, SEQ ID NO:7, SEQ ID NO:10, SEQ ID NO:15, SEQ ID NO:19, SEQ ID NO:22, SEQ ID NO:25 and/or SEQ ID NO:27, or by homologs thereof, and allelic variants thereof.

In one embodiment of the present invention, arthropod EH proteins comprise amino acid sequences SEQ ID NO:8 or SEQ ID NO:23 (including, but not limited to, the proteins consisting of amino acid sequence SEQ ID NO:8 or SEQ ID NO:22, fragments thereof, fusion proteins and multivalent proteins), and proteins encoded by allelic variants of nucleic acid molecules encoding proteins having amino acid sequences SEQ ID NO:8 or SEQ ID NO:22.

In one embodiment, a preferred arthropod EH protein comprises an amino acid sequence of at least about 35 amino acids in length, preferably at least about 50 amino acids in length, more preferably at least about 100 amino acids in length, more preferably at least about 200 amino acids in length, even more preferably at least about 250 amino acids in length. Within this embodiment, a preferred arthropod EH protein of the present invention has an amino acid sequence comprising at least a portion of SEQ ID NO:8 or SEQ ID NO:23. In another embodiment, a preferred arthropod EH protein comprises a full-length protein, i.e., a protein encoded by a full-length coding region.

In another embodiment, a preferred arthropod EH protein of the present invention is encoded by a nucleic acid molecule comprising at least about 12 nucleotides, preferably at least about 16 nucleotides, more preferably at least about 18 nucleotides, more preferably at least about 20 nucleotides, more preferably at least about 25 nucleotides, more preferably at least about 50 nucleotides, more preferably at least about 100 nucleotides, more preferably at least about 350 nucleotides, more preferably at least about 450 nucleotides, more preferably at least about 500 nucleotides, and even more preferably at least about 800 nucleotides. Within this embodiment is an arthropod EH protein encoded by at least a portion nfEH1$_{1605}$, nfEH2$_{1736}$ or by an allelic variant of these nucleic acid molecules. In yet another embodiment, a preferred arthropod EH protein of the present invention is encoded by a nucleic acid molecule comprising an apparently full-length arthropod EH coding region, i.e., a nucleic acid molecule encoding an apparently full-length arthropod EH protein.

One embodiment of an arthropod EH protein of the present invention is a fusion protein that includes an arthropod EH protein-containing domain attached to one or more fusion segments. Suitable fusion segments for use with the present invention include, but are not limited to, segments that can: enhance a protein's stability; act as an immunopotentiator to enhance an immune response against an EH protein; and/or assist purification of an EH protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the EH-containing domain of the protein and can be susceptible to cleavage in order to enable straightforward recovery of an EH protein. Fusion proteins are preferably produced by culturing a recombinant cell transformed with a fusion nucleic acid molecule that encodes a protein including the fusion segment attached to either the carboxyl and/or amino terminal end of an EH-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide. Examples of a particularly preferred fusion protein of the present invention includes PHIS-PfEH1$_{427}$, pBv-PfEH1$_{449}$ and/or PHIS-PfEH2$_{430}$ production of which is disclosed herein.

In another embodiment, an arthropod EH protein of the present invention also includes at least one additional protein segment that is capable of protecting an animal from hematophagous ectoparasite infestations. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds, or portions thereof, capable of protecting an animal from hematophagous ectoparasite infestation by, for example, targeting two different arthropod proteins.

Examples of multivalent protective compounds include, but are not limited to, an EH protein of the present invention attached to one or more compounds protective against one or more arthropod compounds. Preferred second compounds are proteinaceous compounds that effect active immunization (e.g., antigen vaccines), passive immunization (e.g., antibodies), or that otherwise inhibits an arthropod activity that when inhibited can reduce hematophagous ectoparasite burden on and around an animal. Examples of second compounds include a compound that inhibits binding between an arthropod protein and its ligand (e.g., a compound that inhibits flea ATPase activity or a compound that inhibits binding of a peptide or steroid hormone to its receptor), a compound that inhibits hormone (including peptide or steroid hormone) synthesis, a compound that inhibits vitellogenesis (including production of vitellin and/or transport and maturation thereof into a major egg yolk protein), a compound that inhibits fat body function, a compound that inhibits muscle action, a compound that inhibits the nervous system, a compound that inhibits the immune system and/or a compound that inhibits hematophagous ectoparasite feeding. Examples of second compounds also include proteins obtained from different stages of hematophagous ectoparasite development. Particular examples of second compounds include, but are not limited to, serine proteases, cysteine proteases, aminopeptidases, serine protease inhibitor proteins, calreticulins, larval serum proteins and ecdysone receptors, as well as antibodies to and inhibitors of such proteins. In one embodiment, an arthropod EH protein of the present invention is attached to one or more additional compounds protective against hematophagous ectoparasite infestation. In another embodiment, one or more protective compounds, such as those listed above, can be included in a multivalent vaccine comprising an arthropod EH protein of the present invention and one or more other protective molecules as separate compounds.

The present invention also includes mimetopes of EH proteins of the present invention. As used herein, a mimetope of an EH protein of the present invention refers to any compound that is able to mimic the activity of such a protein (e.g., ability to elicit an immune response against an arthropod EH protein of the present invention and/or ability to inhibit EH activity), often because the mimetope has a structure that mimics the EH protein. It is to be noted, however, that the mimetope need not have a structure similar to an EH protein as long as the mimetope functionally mimics the protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); synthetic or natural organic or inorganic molecules, including nucleic acids; and/or any other peptidomimetic compounds. Mimetopes of the present invention can be designed using computer-generated structures of EH proteins of the present invention. Mimetopes can also be obtained by generating random samples of molecules, such as oligonucleotides, peptides or other organic molecules, and screening such samples by affinity chromatography techniques using the corresponding binding partner, (e.g., an EH substrate, an EH substrate analog, or an anti-EH antibody). A preferred mimetope is a peptidomimetic compound that is structurally and/or functionally similar to an EH protein of the present invention, particularly to the active site of the EH protein.

One embodiment of the present invention includes an arthropod EH protein having epoxide hydrolase enzyme activity. Such an EH protein preferably includes a catalytic triad and an oxyanion hole. An example of a catalytic triad includes the residues $Asp^{225}$, $His^{428}$, and $Asp^{352}$ of $nfEH1_{1605}$, or $Asp^{224}$, $His^{427}$, and $Asp^{352}$ of $nfEH2_{1736}$. An example of an oxyanion hole includes residue $Trp^{151}$ of $nfEH1_{1605}$ or $nfEH2_{1736}$. Analysis of the apparent full-length protein sequence disclosed herein indicates that the amino acid sequence includes these amino acid motifs, as well as surrounding consensus sequences.

Suitable arthropods from which to isolate EH proteins of the present invention (including isolation of the natural protein or production of the protein by recombinant or synthetic techniques) preferably include insects and acarines but not Culicidae, Drosophilidae, Calliphoridae, Sphingidae, Lymantriidae, Noctuidae, Fulgoroidae and Aphididae. Preferred arthropods from which to isolate EH proteins include fleas, midges, sand flies, black flies, horse flies, snipe flies, louse flies, horn flies, deer flies, tsetse flies, buffalo flies, blow flies, stable flies, myiasis-causing flies, Psychodidae, biting gnats, lice, mites, bee, wasps, ants, true bugs, ticks, cattle grub, heel flies, Culicoides and warble flies, preferably fleas, ticks and blow flies, and more preferably fleas. Preferred fleas from which to isolate EH proteins include Ctenocephalides, Ceratophyllus, Diamanus, Echidnophaga, Nosopsyllus, Pulex, Tunga, Oropsylla, Orchopeus and Xenopsylla. More preferred fleas include *Ctenocephalides felis, Ctenocephalides canis, Ceratophyllus pulicidae, Pulex irritans, Oropsylla* (*Thrassis*) *bacchi, Oropsylla* (*Diamanus*) *montana, Orchopeus howardi, Xenopsylla cheopis* and *Pulex simulans*, with *C. felis* being even more preferred.

A preferred arthropod EH protein of the present invention is a compound that when administered to an animal in an effective manner, is capable of protecting that animal from hematophagous ectoparasite infestation. In accordance with the present invention, the ability of an EH protein of the present invention to protect an animal from hematophagous ectoparasite infestation refers to the ability of that protein to, for example, treat, ameliorate and/or prevent infestation caused by hematophagous ectoparasites. In particular, the phrase "to protect an animal from hematophagous ectoparasite infestation" refers to reducing the potential for hematophagous ectoparasite population expansion on and around the animal (i.e., reducing the hematophagous ectoparasite burden). Preferably, the hematophagous ectoparasite population size is decreased, optimally to an extent that the animal is no longer bothered by hematophagous ectoparasites. A host animal, as used herein, is an animal from which hematophagous ectoparasites can feed by attaching to and feeding through the skin of the animal. Hematophagous ectoparasites, and other ectoparasites, can live on a host animal for an extended period of time or can attach temporarily to an animal in order to feed. At any given time, a certain percentage of a hematophagous ectoparasite population can be on a host animal whereas the remainder can be in the environment of the animal. Such an environment can include not only adult hematophagous ectoparasites, but also hematophagous ectoparasite eggs and/or hematophagous ectoparasite larvae. The environment can be of any size such that hematophagous ectoparasites in the environment are able to jump onto and off of a host animal. For example, the environment of an animal can include plants, such as crops, from which hematophagous ectoparasites infest an animal. As such, it is desirable not only to reduce the hematophagous ectoparasite burden on an animal per se, but also to reduce the hematophagous ectoparasite burden in the environment of the animal. In one embodiment, an EH protein of the present invention can elicit an immune response (including a humoral and/or cellular immune response) against a hematophagous ectoparasite.

Suitable hematophagous ectoparasites to target include any hematophagous ectoparasite that is essentially incapable of infesting an animal administered an EH protein of the present invention. As such, a hematophagous ectoparasite to target includes any hematophagous ectoparasite that produces a protein having one or more epitopes that can be targeted by a humoral and/or cellular immune response against an epoxide hydrolase protein of the present invention and/or that can be targeted by a compound that otherwise inhibits epoxide hydrolase activity (e.g., a compound that inhibits hydration of octene 1,2-oxide, cis-stilbene oxide, trans-stilbene oxide, styrene oxide, 4-nitrostyrene oxide, trans-β-ethylstyrene oxide, phenanthrene 9,10-oxide, benzo (a)pyrene 4,5-oxide, 1,2,3,4,9,9-hexachloro-6,7-epoxy-1,4, 4a,5,6,7,8,8a-octahydro-1,4-endo-methano-napthalene, squalene 2,3-oxide, cholesterol-5α, 6α-oxide, p-nitrophenyl glycidyl ether, or 1-(4'-ethylphenoxy)-3,7-dimethyl-6,7-epoxy-2E-octene, or the epoxide ring of juvenile hormone, and/or binding to the photoaffinity labels $^3$H-epoxyhomofarnesyl diazoacetate ($^3$H-EHDA), $^3$H-epoxybishomofarnesyl diazoacetate ($^3$H-EBDA), or $^3$H-epoxyfarnesyl diazoacetate ($^3$H-EFDA), thereby resulting in the decreased ability of the hematophagous ectoparasite to infest an animal. Preferred hematophagous ectoparasite to target include ectoparasites disclosed herein as being useful in the production of EH proteins of the present invention.

Translation of SEQ ID NO:4 suggests that nucleic acid molecule $nfEH1_{211}$ encodes a non-full-length arthropod EH protein of about 70 amino acids, referred to herein as $PfEH1_{70}$, represented by SEQ ID NO:5, assuming the first codon spans from nucleotide 2 through nucleotide 4 of SEQ ID NO:4 and the last codon spans from nucleotide 208 through nucleotide 210 of SEQ ID NO:4. The complement of SEQ ID NO:4 is represented herein by SEQ ID NO:6.

Comparison of amino acid sequence SEQ ID NO:5 (i.e., the amino acid sequence of PfEH1$_{70}$) with amino acid sequences reported in GenBank indicates that SEQ ID NO:5 showed the most homology, i.e., about 45% identity, between SEQ ID NO:5 and *Manduca sexta* epoxide hydrolase protein.

Translation of SEQ ID NO:19 suggests that nucleic acid molecule nfEH2$_{211}$ encodes a non-full-length arthropod EH protein of about 70 amino acids, referred to herein as PfEH2$_{70}$, represented by SEQ ID NO:20, assuming the first codon spans from nucleotide 2 through nucleotide 4 of SEQ ID NO:19 and the last codon spans from nucleotide 209 through nucleotide 211 of SEQ ID NO:19. The complement of SEQ ID NO:19 is represented herein by SEQ ID NO:21.

Comparison of amino acid sequence SEQ ID NO:20 (i.e., the amino acid sequence of PfEH2$_{70}$) with amino acid sequences reported in GenBank indicates that SEQ ID NO:20 showed the most homology, i.e., about 40% identity, between SEQ ID NO:20 and *Manduca sexta* epoxide hydrolase.

Translation of SEQ ID NO:7 suggests that nucleic acid molecule nfEH1$_{1605}$ encodes a full-length arthropod epoxide hydrolase protein of about 464 amino acids, referred to herein as PfEH1$_{464}$, represented by SEQ ID NO:8, assuming an open reading frame in which the initiation codon spans from nucleotide 87 through nucleotide 89 of SEQ ID NO:7 and the termination (stop) codon spans from nucleotide 1479 through nucleotide 1481 of SEQ ID NO:7. The complement of SEQ ID NO:7 is represented herein by SEQ ID NO:9. The coding region encoding PfEH1$_{464}$ is represented by the nucleic acid molecule nfEH1$_{1392}$, having a coding strand with the nucleic acid sequence represented by SEQ ID NO:10 and a complementary strand with nucleic acid sequence SEQ ID NO:12. The deduced amino acid sequence of PfEH1$_{464}$ (i.e., SEQ ID NO:8) predicts that PfEH1$_{464}$ has an estimated molecular weight of about 52.6 kD and an estimated pI of about 9.0.

Comparison of amino acid sequence SEQ ID NO:8 (i.e., the amino acid sequence of PfEH1$_{464}$) with amino acid sequences reported in GenBank indicates that SEQ ID NO:8 showed the most homology, i.e., about 40% identity between SEQ ID NO:8 and a *M. sexta* epoxidase protein.

Translation of SEQ ID NO:22 suggests that nucleic acid molecule nfEH2$_{1736}$ encodes a full-length arthropod epoxide hydrolase protein of about 465 amino acids, referred to herein as PfEH2$_{465}$, represented by SEQ ID NO:23, assuming an open reading frame in which the initiation codon spans from nucleotide 159 through nucleotide 161 of SEQ ID NO:22 and a termination codon spanning from nucleotide 1554 through nucleotide 1556 of SEQ ID NO:22. The complement of SEQ ID NO:22 is represented herein by SEQ ID NO:24. The coding region encoding PfEH2$_{465}$ is represented by the nucleic acid molecule nfEH2$_{1395}$, having a coding strand with the nucleic acid sequence represented by SEQ ID NO:25 and a complementary strand with nucleic acid sequence SEQ ID NO:26.

Comparison of amino acid sequence SEQ ID NO:23 (i.e., the amino acid sequence of PfEH2$_{465}$) with amino acid sequences reported in GenBank indicates that SEQ ID NO:23 showed the most homology, i.e., about 44% identity between SEQ ID NO:23 and a *T. ni* epoxide hydrolase protein.

Another embodiment of the present invention is an isolated nucleic acid molecule that hybridizes under stringent hybridization conditions with a *C. felis* EH gene. The identifying characteristics of such a gene are heretofore described. A nucleic acid molecule of the present invention can include an isolated natural arthropod EH gene or a homolog thereof, the latter of which is described in more detail below. A nucleic acid molecule of the present invention can include one or more regulatory regions, full-length or partial coding regions, or combinations thereof. The minimal size of a nucleic acid molecule of the present invention is the minimal size that can form a stable hybrid with a *C. felis* EH gene under stringent hybridization conditions.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified. An isolated arthropod EH nucleic acid molecule of the present invention can be isolated from its natural source or can be produced using recombinant DNA technology (e.g., polymerase chain reaction (PCR) amplification, cloning) or chemical synthesis. Isolated EH nucleic acid molecules can include, for example, natural allelic variants and nucleic acid molecules modified by nucleotide insertions, deletions, substitutions, and/or inversions in a manner such that the modifications do not substantially interfere with the nucleic acid molecule's ability to encode an EH protein of the present invention or to form stable hybrids under stringent conditions with natural gene isolates.

An arthropod EH nucleic acid molecule homolog can be produced using a number of methods known to those skilled in the art (see, for example, Sambrook et al., ibid.). For example, nucleic acid molecules can be modified using a variety of techniques including, but not limited to, classic mutagenesis and recombinant DNA techniques (e.g., site-directed mutagenesis, chemical treatment, restriction enzyme cleavage, ligation of nucleic acid fragments and/or PCR amplification, synthesis of oligonucleotide mixtures and ligation of mixture groups to "build" a mixture of nucleic acid molecules and combinations thereof. Nucleic acid molecule homologs can be selected by hybridization with a *C. felis* EH gene or by screening for the function of a protein encoded by the nucleic acid molecule (e.g., ability to elicit an immune response against at least one epitope of an arthropod EH protein, hydrate octene 1,2-oxide, cis-stilbene oxide, trans-stilbene oxide, styrene oxide, 4-nitrostyrene oxide, trans-β-ethylstyrene oxide, phenanthrene 9,10-oxide, benzo(a)pyrene 4,5-oxide, 1,2,3,4,9,9-hexachloro-6,7-epoxy-1,4,4a,5,6,7,8,8a-octahydro-1,4-endo-methano-napthalene, squalene 2,3-oxide, cholesterol-5α, 6α-oxide, p-nitrophenyl glycidyl ether, or 1-(4'-ethylphenoxy)-3,7-dimethyl-6,7-epoxy-2E-octene, or the epoxide ring of juvenile hormone, and/or bind to the photoaffinity labels $^3$H-epoxyhomofarnesyl diazoacetate ($^3$H-EHDA), $^3$H-epoxybishomofarnesyl diazoacetate ($^3$H-EBDA), or $^3$H-epoxyfarnesyl diazoacetate ($^3$H-EFDA).

Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given flea since the genome is diploid and/or among a group of two or more fleas. The present invention also includes variants due to laboratory manipulation, such as, but not limited to, variants produced during polymerase chain reaction amplification.

An isolated nucleic acid molecule of the present invention can include a nucleic acid sequence that encodes at least one arthropod EH protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding an arthropod EH protein.

A preferred nucleic acid molecule of the present invention, when administered to an animal, is capable of protecting that animal from infestation by a hematophagous ectoparasite. As will be disclosed in more detail below, such a nucleic acid molecule can be, or can encode, an antisense RNA, a molecule capable of triple helix formation, a ribozyme, or other nucleic acid-based drug compound. In additional embodiments, a nucleic acid molecule of the present invention can encode a protective EH protein (e.g., an EH protein of the present invention), the nucleic acid molecule being delivered to the animal, for example, by direct injection (i.e., as a naked nucleic acid) or in a vehicle such as a recombinant virus vaccine or a recombinant cell vaccine.

One embodiment of the present invention is an EH nucleic acid molecule that hybridizes under stringent hybridization conditions with nucleic acid molecule $nfEH1_{211}$, $nfEH2_{211}$, $nfEH1_{1605}$, $nfEH1_{1350}$, $nfEH1_{1392}$, $nfEH1_{1326}$, $nfEH2_{1736}$, $nfEH2_{1395}$ and/or $nfEH2_{1293}$, and preferably with a nucleic acid molecule having nucleic acid sequence SEQ ID NO:4, SEQ ID NO:6, SEQ ID NO:7, SEQ ID NO:9, SEQ ID NO:10, SEQ ID NO:12, SEQ ID NO:15, SEQ ID NO:19, SEQ ID NO:21, SEQ ID NO:22, SEQ ID NO:24, SEQ ID NO:25, SEQ ID NO:26 and/or SEQ ID NO:27.

The present invention also includes fragments of any nucleic acid molecule disclosed herein. According to the present invention, a fragment can include any nucleic acid molecule or nucleic acid sequence, the size of which can range between a length that is smaller than a sequence identified by a SEQ ID NO of the present invention and the minimum size of an oligonucleotide as defined herein. For example, the size of a fragment of the present invention can be any size that is less than about 1395 nucleotides and greater than 36 nucleotides in length.

In another embodiment, a preferred EH nucleic acid molecule encodes an EH protein comprising at least about at least about 35 amino acids in length, preferably at least about 50 amino acids in length, more preferably at least about 100 amino acids in length, more preferably at least about 200 amino acids in length, even more preferably at least about 250 amino acids in length.

In one embodiment of the present invention, a preferred EH nucleic acid molecule includes an isolated nucleic acid molecule which is at least about 50 nucleotides, or at least about 150 nucleotides, and which hybridizes under conditions which preferably allow about 50% base pair mismatch, more preferably under conditions which allow about 45% base pair mismatch, more preferably under conditions which allow about 40% base pair mismatch, more preferably under conditions which allow about 35% base pair mismatch, more preferably under conditions which allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO:4, SEQ ID NO:6, SEQ ID NO:7, SEQ ID NO:9, SEQ ID NO:10, SEQ ID NO:12, SEQ ID NO:15, SEQ ID NO:19, SEQ ID NO:21, SEQ ID NO:22, SEQ ID NO:24, SEQ ID NO:25, SEQ ID NO:26 and/or SEQ ID NO:27.

Another embodiment of the present invention includes a nucleic acid molecule comprising at least about 150 basepairs, wherein the nucleic acid molecule hybridizes, in a solution comprising 1×SSC and 0% formamide, at a temperature of about 52° C., to a nucleic acid sequence selected from the group consisting of SEQ ID NO:4, SEQ ID NO:6, SEQ ID NO:7, SEQ ID NO:9, SEQ ID NO:10, SEQ ID NO:12, SEQ ID NO:15, SEQ ID NO:19, SEQ ID NO:21, SEQ ID NO:22, SEQ ID NO:24, SEQ ID NO:25, SEQ ID NO:26 and/or SEQ ID NO:27. Also preferred are fragments of any of such nucleic acid molecules.

Comparison of nucleic acid sequence SEQ ID NO:4 (i.e., the nucleic acid sequence of $nfEH1_{211}$) with nucleic acid sequences reported in GenBank indicates that SEQ ID NO:4 showed he most homolog, i.e., about 64% identity, between SEQ ID NO:4 and a *Manduca sexta* epoxide hydrolase gene.

Another embodiment of the present invention is an EH nucleic acid molecule that hybridizes under stringent hybridization conditions with nucleic acid molecule $nfEH2_{211}$ and preferably with a nucleic acid molecule having nucleic acid sequence SEQ ID NO:19 and/or SEQ ID NO:21.

Comparison of nucleic acid sequence SEQ ID NO:19 (i.e., the nucleic acid sequence of $nfEH2_{211}$) with nucleic acid sequences reported in GenBank indicates that SEQ ID NO:19 showed he most homolog, i.e., about 40% identity between SEQ ID NO:19 and *H. sapiens* HBF-1 mRNA for transcription factor.

Another embodiment of the present invention is an EH nucleic acid molecule that hybridizes under stringent hybridization conditions with nucleic acid molecule $nfEH1_{1605}$ and preferably with a nucleic acid molecule having nucleic acid sequence SEQ ID NO:7 and/or SEQ ID NO:9.

Comparison of nucleic acid sequence SEQ ID NO:7 (i.e., the nucleic acid sequence of $nfEH1_{1605}$) with nucleic acid sequences reported in GenBank indicates that SEQ ID NO:7 showed the most homology, i.e., about 55% identity, between SEQ ID NO:7 and a *M. sexta* epoxidase gene.

Another embodiment of the present invention is an EH nucleic acid molecule that hybridizes under stringent hybridization conditions with nucleic acid molecule $nfEH2_{1736}$ and preferably with a nucleic acid molecule having nucleic acid sequence SEQ ID NO:22 and/or SEQ ID NO:24.

Comparison of nucleic acid sequence SEQ ID NO:22 (i.e., the nucleic acid sequence of $nfEH2_{1736}$) with nucleic acid sequences reported in GenBank indicates that SEQ ID NO:22 showed the most homology, i.e., about 52% identity, between SEQ ID NO:22 and a *T. ni* epoxide hydrolase gene.

Additional preferred EH nucleic acid molecules of the present invention include an isolated nucleic acid molecule which is at least about 50 nucleotides, or at least about 150 nucleotides, comprising a nucleic acid sequence that is preferably at least about 45% identical, more preferably about 50% identical, more preferably about 55% identical, more preferably about 60% identical, more preferably about 65% identical, more preferably about 70% identical, more preferably about 75% identical, more preferably about 80% identical, more preferably about 85% identical, more preferably about 90% identical and even more preferably about 95% identical to a nucleic acid sequence selected from the group consisting of SEQ ID NO:4, SEQ ID NO:6, SEQ ID NO:7, SEQ ID NO:9, SEQ ID NO:10, SEQ ID NO:12, SEQ ID NO:15, SEQ ID NO:19, SEQ ID NO:21, SEQ ID NO:22, SEQ ID NO:24, SEQ ID NO:25, SEQ ID NO:26 and/or SEQ ID NO:27. Also preferred are fragments of any of such nucleic acid molecules. Percent identity may be determined using the Compare function by maximum matching within the program DNAsis Version 2.1 using default parameters.

Preferred arthropod EH nucleic acid molecules include nucleic acid molecules having a nucleic acid sequence that is at least about 65%, preferably at least about 70%, more preferably at least about 75%, more preferably at least about 80%, more preferably at least about 85%, more preferably at least about 90%, and even more preferably at least about 95% identical to nucleic acid sequence SEQ ID NO:4, SEQ ID NO:6, SEQ ID NO:7, SEQ ID NO:9, SEQ ID NO:10, SEQ ID NO:12, SEQ ID NO:15, SEQ ID NO:19, SEQ ID NO:21, SEQ ID NO:22, SEQ ID NO:24, SEQ ID NO:25, SEQ ID NO:26 and/or SEQ ID NO:27.

One embodiment of the present invention is a nucleic acid molecule comprising all or part of nucleic acid molecules $nFEH1_{211}$, $nFEH2_{211}$, $nFEH1_{1605}$, $nFEH1_{1350}$, $nFEH1_{1392}$, $nFEH1_{1326}$, $nFEH2_{1736}$, $nFEH2_{1395}$ and/or $nFEH2_{1293}$, or allelic variants of these nucleic acid molecules. Another preferred nucleic acid molecule of the present invention includes at least a portion of nucleic acid sequence SEQ ID NO:4, SEQ ID NO:6, SEQ ID NO:7, SEQ ID NO:9, SEQ ID NO:10, SEQ ID NO:12, SEQ ID NO:15, SEQ ID NO:19, SEQ ID NO:21, SEQ ID NO:22, SEQ ID NO:24, SEQ ID NO:25, SEQ ID NO:26 and/or SEQ ID NO:27, as well as allelic variants thereof and homologs of nucleic acid molecules having these nucleic acid sequences; preferably such a homolog encodes or is complementary to a nucleic acid molecule that encodes at least one epitope that elicits and an immune response against a protein having an amino acid sequence SEQ ID NO:5, SEQ ID NO:8, SEQ ID NO:11, SEQ ID NO:20, SEQ ID NO:23 and/or SEQ ID NO:28. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound.

In one embodiment, an EH nucleic acid molecule of the present invention encodes a protein that is at least about 45%, preferably at least about 50%, more preferably at least about 55%, even more preferably at least about 60%, even more preferably at least about 65%, even more preferably at least about 70%, even more preferably at least about 75%, even more preferably at least about 80%, even more preferably at least about 85%, even more preferably at least about 90%, and even more preferably about 95% identical to $PfEH1_{464}$ and/or $PfEH2_{465}$. Even more preferred is a nucleic acid molecule encoding $PfEH1_{70}$, $PfEH2_{70}$, $PfEH1_{427}$, $PfEH1_{464}$, $PfEH1_{449}$, $PfEH2_{465}$ and/or $PfEH2_{430}$, and/or an allelic variant of such a nucleic acid molecule.

In another embodiment, an EH nucleic acid molecule of the present invention encodes a protein having an amino acid sequence that is at least about 45%, preferably at least about 50%, more preferably at least about 55%, even more preferably at least about 60%, even more preferably at least about 65%, even more preferably at least about 70%, even more preferably at least about 75%, even more preferably at least about 80%, even more preferably at least about 85%, even more preferably at least about 90%, and even more preferably about 95% identical to SEQ ID NO:5, SEQ ID NO:8, SEQ ID NO:11, SEQ ID NO:20, SEQ ID NO:23 and/or SEQ ID NO:28. The present invention also includes an EH nucleic acid molecule encoding a protein having at least a portion of SEQ ID NO:5, SEQ ID NO:8, SEQ ID NO:11, SEQ ID NO:20, SEQ ID NO:23 and/or SEQ ID NO:28, as well as allelic variants of an EH nucleic acid molecule encoding a protein having these sequences, including nucleic acid molecules that have been modified to accommodate codon usage properties of the cells in which such nucleic acid molecules are to be expressed.

A more preferred nucleic acid molecule includes the nucleic acid sequence SEQ ID NO:4, SEQ ID NO:6, SEQ ID NO:7, SEQ ID NO:9, SEQ ID NO:10, SEQ ID NO:12, SEQ ID NO:15, SEQ ID NO:19, SEQ ID NO:21, SEQ ID NO:22, SEQ ID NO:24, SEQ ID NO:25, SEQ ID NO:26 and/or SEQ ID NO:27, as well as allelic variants thereof. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound. Particularly preferred nucleic acid molecules include $nFEH1_{211}$, $nFEH2_{211}$, $nFEH1_{1605}$, $nFEH1_{1350}$, $nFEH1_{1392}$, $nFEH1_{1326}$, $nFEH2_{1736}$, $nFEH2_{1395}$ and/or $nFEH2_{1293}$.

The present invention also includes a nucleic acid molecule encoding a protein having at least a portion of SEQ ID NO:5, SEQ ID NO:8, SEQ ID NO:11, SEQ ID NO:20, SEQ ID NO:23 and/or SEQ ID NO:28, including nucleic acid molecules that have been modified to accommodate codon usage properties of the cells in which such nucleic acid molecules are to be expressed.

Knowing the nucleic acid sequences of certain arthropod EH nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain EH nucleic acid molecules from other arthropods. Such nucleic acid molecules can be obtained in a variety of ways including screening appropriate expression libraries with antibodies of the present invention; traditional cloning techniques using oligonucleotide probes of the present invention to screen appropriate libraries or DNA; and PCR amplification of appropriate libraries or DNA using oligonucleotide primers of the present invention. Preferred libraries to screen or from which to amplify nucleic acid molecules include flea $1^{st}$ instar larvae; $3^{rd}$ instar larvae, wandering larvae, prepupal larvae, pupae and whole adult flea cDNA libraries as well as genomic DNA libraries. Similarly, preferred DNA sources to screen or from which to amplify nucleic acid molecules include flea prepupal cDNA, adult cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising arthropod EH genes or other arthropod EH nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. Minimal size characteristics are disclosed herein. The present invention includes oligonucleotides that can be used as, for example, probes to identify nucleic acid molecules, primers to produce nucleic acid molecules or therapeutic reagents to inhibit EH protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulation of arthropod EH nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, insect, other animal, and plant cells. Preferred expression vectors of the present invention can direct gene expression in bacterial, yeast, insect and mammalian cells and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, insect and mammalian cells, such as, but not limited to, tac, lac, trp, trc, oxy-pro, omp/lpp, rrnB, bacteriophage lambda(such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with arthropods, such as, *C. felis*.

Suitable and preferred nucleic acid molecules to include in recombinant vectors of the present invention are as disclosed herein. Preferred nucleic acid molecules to include in recombinant vectors, and particularly in recombinant molecules, include $nfEH1_{211}$, $nfEH2_{211}$, $nfEH1_{1605}$, $nfEH1_{1350}$, $nfEH1_{1392}$, $nfEH1_{1326}$, $nfEH2_{1736}$, $nfEH2_{1395}$ and/or $nfEH2_{1293}$. Particularly preferred recombinant molecules of the present invention include $pTrc-nfEH1_{1284}$, $pFB-nfEH1_{1350}$ and/or $pTrc-nfEH2_{1293}$, the production of which are described in the Examples section.

Recombinant molecules of the present invention may also (a) contain secretory signals (i.e., signal segment nucleic acid sequences) to enable an expressed arthropod protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments, as well as natural signal sequences. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include arthropod EH nucleic acid molecules disclosed herein. Particularly preferred nucleic acid molecules with which to transform a cell include $nfEH1_{211}$, $nfEH2_{211}$, $nfEH1_{1605}$, $nfEH1_{1350}$, $nfEH1_{1392}$, $nfEH1_{1326}$, $nfEH2_{1736}$, $nfEH2_{1395}$ and/or $nfEH2_{1293}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing arthropod EH proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite, other insect, other animal and plant cells. Preferred host cells include bacterial, mycobacterial, yeast, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi*; *Salmonella typhimurium*, including attenuated strains such as UK-1 $_x$3987 and SR-11 $_x$4072; *Spodoptera frugiperda*; *Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, $LMTK^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed, examples of which are disclosed herein. Particularly preferred recombinant molecules include $pTrc-nfEH1_{1284}$, $pFB-nfEH1_{1350}$ and $pTrc-nfEH2_{1293}$.

A recombinant cell of the present invention includes any cell transformed with at least one of any nucleic acid molecule of the present invention. Suitable and preferred nucleic acid molecules as well as suitable and preferred recombinant molecules with which to transform cells are disclosed herein. Particularly preferred recombinant cells include *E. coli*:$pTrc-nfEH1_{1284}$ and *S. frugiperda*:$pFB-nfEH1_{1350}$ and/or *E. coli*:$pTrc-nfEH2_{1293}$. Details regarding the production of these recombinant cells are disclosed herein.

Recombinant cells of the present invention can also be co-transformed with one or more recombinant molecules including arthropod EH nucleic acid molecules encoding one or more proteins of the present invention and one or more other nucleic acid molecules encoding other protective compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated EH proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce an arthropod EH protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane. The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to an arthropod EH protein of the present invention or a mimetope thereof (i.e., anti-arthropod EH antibodies). As used herein, the term "selectively binds to" an EH protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid. An anti-arthropod EH antibody preferably selectively binds to an arthropod EH protein in such a way as to reduce the activity of that protein.

Isolated antibodies of the present invention can include antibodies in a bodily fluid (such as, but not limited to, serum), or antibodies that have been purified to varying degrees. Antibodies of the present invention can be polyclonal or monoclonal, functional equivalents such as antibody fragments and genetically-engineered antibodies, including single chain antibodies or chimeric antibodies that can bind to more than one epitope.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce arthropod EH proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from arthropods susceptible to treatment by such antibodies and/or (b) as tools to screen expression libraries and/or to recover desired proteins of the present invention from a mixture of proteins and other contaminants. Furthermore, antibodies of the present invention can be used to target cytotoxic agents to hematophagous ectoparasites such as those discloses herein, in order to directly kill such hematophagous ectoparasites. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal in an effective manner, is capable of protecting that animal from infestation by hematophagous ectoparasite. Therapeutic compositions of the present invention include at least one of the following protective compounds: an isolated hematophagous ectoparasite EH protein (including a peptide); a mimetope of such a protein; an isolated nucleic acid molecule that hybridizes under stringent hybridization conditions with a *Ctenocephalides felis* EH gene; an isolated antibody that selectively binds to an hematophagous ectoparasite EH protein; and inhibitors of hematophagous ectoparasite EH activity (including EH substrate analogs). Other protective compounds include for example, antisense-, triplex formation-, ribozyme- and/or RNA drug-based technologies. As used herein, a protective compound refers to a compound that, when administered to an animal in an effective manner, is able to treat, ameliorate, and/or prevent disease caused by an arthropod of the present invention. Preferred arthropods to target are heretofore disclosed. Examples of proteins, nucleic acid molecules, antibodies and inhibitors of the present invention are disclosed herein.

A preferred therapeutic composition of the present invention includes at least one of the following protective compounds: an isolated flea EH protein (including a peptide); a mimetope of such a protein; an isolated hematophagous ectoparasite EH nucleic acid molecule that hybridizes under stringent hybridization conditions with a *Ctenocephalides felis* EH gene; an isolated antibody that selectively binds to a hematophagous ectoparasite EH protein; and an inhibitor of EH activity identified by its ability to inhibit the activity of a flea EH (including a substrate analog).

Suitable inhibitors of EH activity are compounds that inhibit EH protein activity, usually by binding to or otherwise interacting with or otherwise modifying the EH's active site. EH inhibitors can also interact with other regions of the EH protein to inhibit EH activity, for example, by allosteric interaction. Inhibitors of EHs are usually relatively small compounds and as such differ from anti-EH antibodies. Preferably, an EH inhibitor of the present invention is identified by its ability to bind to, or otherwise interact with, a flea EH protein, thereby inhibiting the activity of the flea EH.

EH inhibitors can be used directly as compounds in compositions of the present invention to treat animals as long as such compounds are not harmful to host animals being treated. EH inhibitors can also be used to identify preferred types of arthropod EHs to target using compositions of the present invention, for example by affinity chromatography. Preferred EH inhibitors of the present invention include, but are not limited to, flea EH substrate analogs, and other molecules that bind to a flea EH (e.g., to an allosteric site) in such a manner that EH activity of the flea EH is inhibited; examples include, but are not limited to, juvenile hormone analogs. An EH substrate analog refers to a compound that interacts with (e.g., binds to, associates with, modifies) the active site of an EH protein. A preferred EH substrate analog inhibits EH activity. EH substrate analogs can be of any inorganic or organic composition. EH substrate analogs can be, but need not be, structurally similar to an EH's natural substrate as long as they can interact with the active site of that EH protein. EH substrate analogs can be designed using computer-generated structures of EH proteins of the present invention or computer structures of EHs' natural substrates. Substrate analogs can also be obtained by generating random samples of molecules, such as oligonucleotides, peptides, peptidomimetic compounds, or other inorganic or organic molecules, and screening such samples by affinity chromatography techniques using the corresponding binding partner, (e.g., a flea EH). A preferred EH substrate analog is a juvenile hormone mimetic compound (i.e., a compound that is structurally and/or functionally similar to a natural substrate of an EH of the present invention, particularly to the region of the substrate that interacts with the EH active site, but that inhibits EH activity upon interacting with the EH active site).

One therapeutic composition of the present invention includes an inhibitor of arthropod EH activity, i.e., a compound capable of substantially interfering with the function of an arthropod EH susceptible to inhibition by an inhibitor of arthropod EH activity. An inhibitor of EH activity can be identified using arthropod EH proteins of the present invention. One embodiment of the present invention is a method to identify a compound capable of inhibiting EH activity of an arthropod. Such a method includes the steps of (a) contacting (e.g., combining, mixing) an isolated flea EH protein, preferably a *C. felis* EH protein of the present invention, with a putative inhibitory compound under conditions in which, in the absence of the compound, the protein has EH activity, and (b) determining if the putative inhibitory compound inhibits the EH activity.

Another embodiment of a method to identify a compound capable of inhibiting EH activity of an arthropod includes the steps of (a) contacting an isolated flea EH protein, preferably a *C. felis* EH protein of the present invention, with a putative inhibitory compound under conditions in which the EH protein can bind to the putative inhibitory compound, and (b) determining if the putative inhibitory compound binds to the EH protein.

Putative inhibitory compounds to screen include small organic molecules, antibodies (including mimetopes thereof) and substrate analogs. Methods to determine EH activity are known to those skilled in the art; see, for example, the Examples section of the present application. Methods to determine binding of a putative inhibitory compounds to an EH protein are known to those of skill in the art and include, for example, determining changes in molecular mass using surface plasmon resonance (e.g., determining light scatter by an inhibitor or an EH protein, before and after contacting the inhibitor or protein with an EH protein or inhibitor, respectively).

The present inventors have discovered that juvenile hormone esterase and juvenile hormone epoxide hydrolase are active from early flea larval stages to adulthood, and that the relative activities of these two enzymes change with development. One embodiment of an inhibitor of the present invention comprises a compound capable of inhibiting both juvenile hormone esterase and juvenile hormone epoxide hydrolase (referred to herein as a bifunctional inhibitor). A suitable bifunctional inhibitor of the present invention includes a first portion that specifically inhibits the activity of a serine esterase and a second portion that specifically inhibits the activity of an epoxide hydrolase. Preferably, a serine esterase inhibitor is operatively linked to an epoxide hydrolase inhibitor by a structure that is substantially similar to the structure of juvenile hormone. A preferred bifunctional inhibitor of the present invention includes a compound that is capable of inhibiting juvenile hormone esterase and juvenile hormone epoxide hydrolase activity. A bifunctional inhibitor of the present invention preferably binds substantially irreversibly to its targets (e.g., serine esterase and epoxide hydrolase). A bifunctional inhibitor of the present invention is capable of inhibiting the activity of its target at $IC_{50}$ at a final concentration of about 10 millimolar, more preferably about 1 millimolar, even more preferably about 100 micromolar, even more preferably about 10 micromolar, even more preferably about 1 micromolar, even more preferably about 100 nanomolar, even more preferably about 10 nanomolar, and even more preferably less than or equal to about 1 nanomolar of bifunctional inhibitor. Preferably, a bifunctional inhibitor of the present invention is capable of inhibiting juvenile hormone epoxide hydrolase activity at $IC_{50}$ at a final concentration of 1 millimolar of the inhibitor and juvenile hormone esterase activity at $IC_{50}$ at a final concentration of 1 millimolar of the inhibitor.

As used herein, the term $IC_{50}$ refers to the concentration of an inhibitor at which about 50% of the activity of an enzyme is inhibited by the inhibitor. The term "inhibiting juvenile hormone epoxide hydrolase activity at $IC_{50}$ at a final concentration of 1 millimolar of the inhibitor" refers to a compound capable of inhibiting about 50% of JHEH activity at a final concentration of 1 millimolar (i.e., 1 millimole per liter of volume) of the inhibitor. The term "inhibiting juvenile hormone esterase activity at $IC_{50}$ at a final concentration of 1 millimolar of the inhibitor" refers to a compound capable of inhibiting about 50% of JHEH activity at a final concentration of 1 millimolar of the inhibitor.

Methods to measure JHEH activity are known to those of skill in the art, and include methods such as those described herein in the Examples section. Inhibition of JHEH activity can be identified by determining JHEH activity in the presence or absence of an inhibitor.

Methods to measure JHE activity are known to those of skill in the art, and include, for example the following method. Unlabeled juvenile hormone is diluted in hexane to concentration of about 0.025 M. Labeled $10\text{-}^3$H-juvenile hormone is diluted in hexane to concentration of about 80,000 cpm/$\mu$l. A JH substrate mixture is prepared by mixing about 20 $\mu$l of unlabeled JH with about 80 $\mu$l of $^3$H-JH (about 5 $\mu$Ci) in a 4 ml screw cap vial. The substrate mixture is then covered with nitrogen (i.e., "blanketed") and the solvent contained in the mixture is evaporated by heating the mixture at 35° C. When just dry, about 1 ml of absolute anhydrous ethanol (final concentration $5\times10^{-4}$, or 6400 cpm/$\mu$l) is added to the vial. The substrate mixture is then stored at −20° C. About 10 equivalents of a tissue (about 5–10 $\mu$l of protein) is added into the bottom of a small glass autosampler vial. About 90–95 $\mu$l of Tris-buffered saline (TBS) is added to the vial to bring the final volume to about 100 $\mu$l. Two control samples are also prepared by adding 100 $\mu$l TBS to two separate vials. About 1 $\mu$l of the substrate mixture described above is added to all of the vials except the control samples. The final JH concentration in each vial is about $5\times10^{-6}$ M. The vials is then capped and spun in a microfuge to bring all of the liquid to the bottom of the vial. The vials were then transferred to a heat block and incubated at 35° C. for about 30 minutes. Following the incubation, enzyme activity was stopped by adding about 50 $\mu$l of methanol buffer (methanol:water:concentrated ammonium hydroxide at a 10:9:1 ratio, respectively) to each vial and removing the vials from the heat block. To measure released juvenile hormone acid, about 250 $\mu$l isooctane is added to each vial. The vial is vortexed for about 15 seconds or until an emulsion formed. The vial was then centrifuged in a microfuge for about 1 minute to separate aqueous and organic phases. About 75 μl of the aqueous layer is removed from the vial and added to about 2 ml Eco-lume scintillation fluid. The amount of radioactivity contained in each vial was determined using a Beckman LS-1801 liquid scintillation counter. Inhibition of JHE activity can be identified by determining JHE activity in the presence or absence of an inhibitor.

A preferred embodiment of a bifunctional inhibitor of the present invention comprises a compound of the formula:

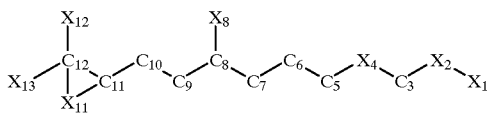

in which $X_1$ represents alkyl, hydroxy, sulfhydryl, alkoxy, alkylthio, trifluoromethyl, amino, or alkyl amine; $X_2$ represents carbonyl, thiocarbonyl, sulfinyl, alkyl phosphoester, aryl phosphoester, alkyl phosphothiolester, or aryl phosphothiolester; $X_4$ represents sulfur, methylene or an alkylated methylene; $X_8$ represents hydrogen or alkyl; $X_{11}$ represents oxygen, sulfur, or difluoromethylene; $X_{12}$ represents alkyl, hydroxy, alkoxy, fluorine, or trifluoromethyl; $X_{13}$ represents alkyl, hydroxy, alkoxy, fluorine, or trifluoromethyl; the $C_3$—$X_4$ bond is saturated or unsaturated; and the $C_7$—$C_8$ bond is saturated or unsaturated. More preferably, $X_1$ represents trifluoromethyl or amino; $X_2$ represents carbonyl, thiocarbonyl, alkyl phosphoester, aryl phosphoester, alkyl phosphothiolester, or aryl phosphothiolester; $X_4$ represents sulfur or methylene; $X_8$ represents methyl, ethyl, or hydrogen; $X_{11}$ represents oxygen or sulfur; $X_{12}$ represents methyl, ethyl, or alkoxy; $X_{13}$ represents methyl, ethyl, or alkoxy; the $C_3$—$X_4$ bond is saturated or unsaturated; and the $C_7$—$C_8$ bond is saturated or unsaturated.

Even more preferably, $X_1$ represents trifluoromethyl, $X_2$ represents carbonyl, $X_4$ represents sulfur, $X_8$ represents methyl or ethyl, $X_{11}$ represents oxygen, $X_{12}$ represents methyl or ethyl, $X_{13}$ represents methoxy, the $C_3$—$X_4$ bond is saturated, and the $C_7$—$C_8$ bond is unsaturated; or $X_1$ represents trifluoromethyl, $X_2$ represents carbonyl, $X_4$ represents sulfur, $X_8$ represents hydrogen, $X_{11}$ represents oxygen, $X_{12}$ represents methyl or ethyl, $X_{13}$ represents methyl, the $C_3$—$X_4$ bond is saturated, and the $C_7$—$C_8$ bond is saturated; or $X_1$ represents amino, $X_2$ represents phenyl phosphothiolate, benzyl phosphothiolate, or 2-pyridinyl phosphothiolate, $X_4$ represents methylene, $X_8$ represents methyl or ethyl, $X_{11}$ represents oxygen, $X_{12}$ represents methyl or ethyl, $X_{13}$ represents methoxy, the $C_3$—$X_4$ bond is saturated, and the $C_7$—$C_8$ bond is unsaturated; or $X_1$ represents amino, $X_2$ represents phenyl phosphothiolate, benzyl phosphothiolate, or 2-pyridinyl phosphothiolate, $X_4$ represents methylene, $X_8$ represents hydrogen, $X_{11}$ represents oxygen, $X_{12}$ represents methyl or ethyl, $X_{13}$ represents methyl, the $C_3$—$X_4$ bond is saturated, and the $C_7$—$C_8$ bond is saturated.

EH proteins, mimetopes, mimetics, bifunctional inhibitors and substrate analogs, as well as other protective and inhibitor compounds described herein, can be used directly as compounds in compositions of the present invention to treat animals as long as such compounds are not harmful to the animals being treated.

The present invention also includes a therapeutic composition comprising at least one arthropod EH-based compound of the present invention in combination with at least one additional compound protective against hematophagous ectoparasite infestation. Examples of such compounds are disclosed herein.

In one embodiment, a therapeutic composition of the present invention can be used to protect an animal from hematophagous ectoparasite infestation by administering such composition to a hematophagous ectoparasite, such as to a flea, in order to prevent infestation. Such administration could be oral, or by application to the environment (e.g., spraying). Examples of such compositions include, but are not limited to, transgenic vectors capable of producing at least one therapeutic composition of the present invention. In another embodiment, a hematophagous ectoparasite, such as a flea, can ingest therapeutic compositions, or products thereof, present in the blood of a host animal that has been administered a therapeutic composition of the present invention.

Compositions of the present invention can be administered to any animal susceptible to hematophagous ectoparasite infestation (i.e., a host animal), including warm-blooded animals. Preferred animals to treat include mammals and birds, with cats, dogs, humans, cattle, chinchillas, ferrets, goats, mice, minks, rabbits, raccoons, rats, sheep, squirrels, swine, chickens, ostriches, quail and turkeys as well as other furry animals, pets, zoo animals, work animals and/or food animals, being more preferred. Particularly preferred animals to protect are cats and dogs.

In accordance with the present invention, a host animal (i.e., an animal that is or is capable of being infested with a hematophagous ectoparasite) is treated by administering to the animal a therapeutic composition of the present invention in such a manner that the composition itself (e.g., an EH inhibitor, an EH synthesis suppressor (i.e., a compound that decreases the production of EH in the hematophagous ectoparasite), an EH mimetope, or an anti-EH antibody) or a product generated by the animal in response to administration of the composition (e.g., antibodies produced in response to administration of an arthropod EH protein or nucleic acid molecule, or conversion of an inactive inhibitor "prodrug" to an active EH inhibitor) ultimately enters the hematophagous ectoparasite. A host animal is preferably treated in such a way that the compound or product thereof enters the blood stream of the animal. Hematophagous ectoparasites are then exposed to the composition or product when they feed from the animal. For example, flea EH inhibitors administered to an animal are administered in such a way that the inhibitors enter the blood stream of the animal, where they can be taken up by feeding fleas. In another embodiment, when a host animal is administered an arthropod EH protein or nucleic acid molecule, the treated animal mounts an immune response resulting in the production of antibodies against the EH (i.e., anti-EH antibodies) which circulate in the animal's blood stream and are taken up by hematophagous ectoparasites upon feeding. Blood taken up by hematophagous ectoparasites enters the hematophagous ectoparasites where compounds of the present invention, or products thereof, such as anti-EH antibodies, EH inhibitors, EH proteins or mimetopes and/or EH synthesis suppressors, interact with, and reduce EH activity in the hematophagous ectoparasite.

The present invention also includes the ability to reduce larval hematophagous ectoparasite infestation in that when hematophagous ectoparasites feed from a host animal that has been administered a therapeutic composition of the present invention, at least a portion of compounds of the present invention, or products thereof, in the blood taken up by the hematophagous ectoparasite are excreted by the hematophagous ectoparasite in feces, which is subsequently ingested by hematophagous ectoparasite larvae. In particular, it is of note that flea larvae obtain most, if not all, of their nutrition from flea feces.

In accordance with the present invention, reducing EH activity in a hematophagous ectoparasite can lead to a number of outcomes that reduce hematophagous ectoparasite burden on treated animals and their surrounding environments. Such outcomes include, but are not limited to, (a) reducing the viability of hematophagous ectoparasites that feed from the treated animal, (b) reducing the fecundity of female hematophagous ectoparasites that feed from the treated animal, (c) reducing the reproductive capacity of male hematophagous ectoparasites that feed from the treated animal, (d) reducing the viability of eggs laid by female hematophagous ectoparasites that feed from the treated animal, (e) altering the blood feeding behavior of hematophagous ectoparasites that feed from the treated animal (e.g., hematophagous ectoparasites take up less volume per feeding or feed less frequently), (f) reducing the viability of hematophagous ectoparasite larvae, for example due to the feeding of larvae from feces of hematophagous ectoparasites that feed from the treated animal and/or (g) altering the development of hematophagous ectoparasite larvae (e.g., by decreasing feeding behavior, inhibiting growth, inhibiting (e.g., slowing or blocking) molting, and/or otherwise inhibiting maturation to adults).

Therapeutic compositions of the present invention also include excipients in which protective compounds are formulated. An excipient can be any material that the animal to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, dog serum albumin, cat serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), Flt-3 ligand, interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T cell expressed and presumably secreted), macrophage inflammatory proteins (e.g., MIP-1 alpha and MIP-1 beta), and Leishmania elongation initiating factor (LEIF); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Titermax® Research Adjuvant (CytRx®, Inc. Norcross, Ga.); Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of an animal at a constant rate sufficient to attain therapeutic dose levels of the composition to protect an animal from hematophagous ectoparasite infestation. The therapeutic composition is preferably released over a period of time ranging from about 1 to about 12 months. A preferred controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Acceptable protocols to administer therapeutic compositions of the present invention in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition is from about 1 microgram ($\mu$g) to about 10 milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 $\mu$g to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal, intraocular and intramuscular routes.

According to one embodiment, a nucleic acid molecule of the present invention can be administered to an animal in a fashion to enable expression of that nucleic acid molecule into a protective protein or protective RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid vaccine (e.g., as naked DNA or RNA molecules, such as is taught, for example in Wolff et al., 1990, *Science* 247, 1465–1468) or (b) administering a nucleic acid molecule packaged as a recombinant virus vaccine or as a recombinant cell vaccine (i.e., the nucleic acid molecule is delivered by a viral or cellular vehicle).

A naked nucleic acid vaccine of the present invention includes a nucleic acid molecule of the present invention and preferably includes a recombinant molecule of the present invention that preferably is replication, or otherwise amplification, competent. A naked nucleic acid vaccine of the present invention can comprise one or more nucleic acid molecules of the present invention in the form of, for example, a bicistronic recombinant molecule having, for example one or more internal ribosome entry sites. Preferred naked nucleic acid vaccines include at least a portion of a viral genome (i.e., a viral vector). Preferred viral vectors include those based on alphaviruses, poxviruses, adenoviruses, herpesviruses, and retroviruses, with those based on alphaviruses (such as Sindbis or Semliki virus), species-specific herpesviruses and species-specific poxviruses being particularly preferred. Any suitable transcription control sequence can be used, including those disclosed as suitable for protein production. Particularly preferred transcription control sequence include cytomegalovirus intermediate early (preferably in conjunction with Intron-A), Rous Sarcoma Virus long terminal repeat, and tissue-specific transcription control sequences, as well as transcription control sequences endogenous to viral vectors if viral vectors are used. The incorporation of "strong" poly(A) sequences are also preferred.

Naked nucleic acid vaccines of the present invention can be administered in a variety of ways, with intramuscular, subcutaneous, intradermal, transdermal, intranasal and oral routes of administration being preferred. A preferred single dose of a naked nucleic acid vaccines ranges from about 1 nanogram (ng) to about 100 µg, depending on the route of administration and/or method of delivery, as can be determined by those skilled in the art. Suitable delivery methods include, for example, by injection, as drops, aerosolized and/or topically. Naked DNA of the present invention can be contained in an aqueous excipient (e.g., phosphate buffered saline) alone or a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging-deficient and/or encodes an attenuated virus. A number of recombinant viruses can be used, including, but not limited to, those based on alphaviruses, poxviruses, adenoviruses, herpesviruses, and retroviruses. Preferred recombinant virus vaccines are those based on alphaviruses (such as Sindbis virus), raccoon poxviruses, species-specific herpesviruses and species-specific poxviruses. An example of methods to produce and use alphavirus recombinant virus vaccines is disclosed in PCT Publication No. WO 94/17813, by Xiong et al., published Aug. 18, 1994, which is incorporated by reference herein in its entirety.

When administered to an animal, a recombinant virus vaccine of the present invention infects cells within the immunized animal and directs the production of a protective protein or RNA nucleic acid molecule that is capable of protecting the animal from hematophagous ectoparasite infestation. For example, a recombinant virus vaccine comprising an arthropod EH nucleic acid molecule of the present invention is administered according to a protocol that results in the animal producing a sufficient immune response to protect itself from hematophagous ectoparasite infestation. A preferred single dose of a recombinant virus vaccine of the present invention is from about $1 \times 10^4$ to about $1 \times 10^7$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes recombinant cells of the present invention that express at least one protein of the present invention. Preferred recombinant cells for this embodiment include Salmonella, *E. coli*, Listeria, Mycobacterium, *S. frugiperda*, yeast, (including *Saccharomyces cerevisiae*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to protect an animal from hematophagous ectoparasite infestation can be tested in a variety of ways including, but not limited to, detection of anti-arthropod EH antibodies (using, for example, proteins or mimetopes of the present invention), detection of cellular immunity within the treated animal, or challenge of the treated animal with hematophagous ectoparasites to determine whether, for example, the feeding, fecundity or viability of hematophagous ectoparasites feeding from the treated animal is disrupted. Challenge studies can include attachment of chambers containing hematophagous ectoparasites onto the skin of the treated animal. In one embodiment, therapeutic compositions can be tested in animal models such as mice. Such techniques are known to those skilled in the art.

One preferred embodiment of the present invention is the use of arthropod protective compounds, such as proteins, mimetopes, nucleic acid molecules, antibodies and inhibitory compounds of the present invention, to protect an animal from hematophagous ectoparasite, and particularly flea, infestation. Preferred protective compounds of the present invention include, but are not limited to, *C. felis* EH nucleic acid molecules, *C. felis* EH proteins and mimetopes thereof, anti-*C. felis* EH antibodies, and inhibitors of *C. felis* EH activity. More preferred protective compounds of the present invention include, but are not limited to, JHEH formulations of the present invention, *C. felis* JHEH nucleic acid molecules, *C. felis* JHEH proteins and mimetopes thereof, anti-flea JHEH antibodies, inhibitors of *C. felis* JHEH activity and inhibitors of flea JHEH activity. Additional protection may be obtained by administering additional protective compounds, including other proteins, mimetopes, nucleic acid molecules, antibodies and inhibitory compounds, as disclosed herein.

The present invention also includes a therapeutic composition comprising at least one flea EH-based compound of the present invention in combination with at least one additional compound protective against hematophagous ectoparasite infestation. Examples of such compounds are disclosed herein.

The present invention also includes a test kit to identify a compound capable of inhibiting EH activity of an arthropod. Such a test kit includes an isolated flea EH protein, preferably a *C. felis* EH protein, having EH activity and a means for determining the extent of inhibition of EH activity in the presence of (i.e., effected by) a putative inhibitory compound. Such compounds are also screened to identify those that are substantially not toxic in host animals.

EH inhibitors isolated by such a method, and/or test kit, can be used to inhibit any EH that is susceptible to such an inhibitor. Preferred EH proteins to inhibit are those produced by arthropods. A particularly preferred EH inhibitor of the present invention is capable of protecting an animal from hematophagous ectoparasite infestation. Effective amounts and dosing regimens can be determined using techniques known to those skilled in the art.

The following examples are provided for the purposes of illustration and are not intended to limit the scope of the present invention.

EXAMPLES

It is to be noted that the Examples include a number of molecular biology, microbiology, immunology and biochemistry techniques considered to be known to those skilled in the art. Disclosure of such techniques can be found, for example, in Sambrook et al., ibid., and related references.

Example 1

This example describes the identification of epoxide hydrolase nucleic acid molecules of the present invention.

Nucleic acid molecules encoding flea epoxide hydrolase protein, representing a flea epoxide hydrolase gene, was PCR amplified were identified as follows. The fopllowing cDNA libraries were produced. A flea wandering larval cDNA library was prepared as follows. Total RNA was extracted from wandering larval tissue using an acid-guanidinium-phenol-chloroform method similar to that described by Chomczynski et al., 1987, *Anal. Biochem.* 162, p. 156–159. Approximately 3,653 wandering larvae were used in each RNA preparation. Poly A+ selected RNA was separated from total RNA preparation by oligo-dT cellulose chromatography using Poly(A)Quick® mRNA isolation kits (available from Stratagene Cloning Systems, La Jolla, Calif.), according to the method recommended by the manufacturer. A wandering larval cDNA expression library was constructed in lambda (λ) Uni-ZAP™XR vector (available from Stratagene Cloning Systems) using Stratagene's ZAP-cDNA Synthesis Kit® protocol. About 6.72 μg of wandering larval poly A+ RNA was used to produce the wandering larval library. The resultant wandering larval library was amplified to a titer of about $3.5 \times 10^{10}$ pfu/ml with about 97% recombinants.

A flea mixed instar cDNA library was prepared as follows. The flea mixed instar cDNA library was produced using unfed 1st instar, bovine blood-fed 1st instar, bovine blood-fed $2^{nd}$ instar and bovine blood-fed $3^{rd}$ instar flea larvae (this combination of tissues is referred to herein as mixed instar larval tissues for purposes of this example). Total RNA was extracted from mixed instar using the method described above using about 5,164 mixed instar larvae. Poly A+ selected RNA was isolated as described above and about 6.34 μg of mixed instar poly A+ RNA was used to construct a mixed instar cDNA expression library as described above. The resultant mixed instar library was amplified to a titer of about $2.17 \times 10^{10}$ pfu/ml with about 97% recombinants.

A bovine blood-fed gut cDNA library produced as follows. Total RNA was extracted from approximately 3500 guts from bovine blood-fed fleas using a standard guanidinium thiocyanate procedure for lysis and denaturation of the gut tissue, followed by centrifugation in cesium chloride to pellet the RNA. Messenger RNA was isolated from the total RNA using a Fast Track™ Kit (available from In Vitrogen, San Diego, Calif.).

A. PCR Clones

A pair of primers was used to amplify an initial DNA clone from the cDNA libraries. A sense vector primer T-3X (corresponding to the vector in which nucleic acid molecules of the present invention had been ligated), having the nucleic acid sequence 5' AAT TAA CCC TCA CTA AAG GG 3' (available from Gibco BRL, Gaithersburg, Md.; denoted SEQ ID NO:1), was used in combination with a degenerate antisense primer referred to herein as JHEHAs, having the nucleic acid sequence 5' GGC TTV GWR GCT TGK ATR TG 3' (V indicating an A, C or G; W indicating an A or T; R indicating an A or G; and K indicating an G or T; denoted SEQ ID NO:2). The design of the JHEHAs primer is unique because the inventors discovered a highly conserved region of epoxide hydrolase nucleic acid sequences suitable for production of a degenerate primer based on clone sequences disclosed in Roe et al., ibid. and Wojtasek et al., ibid.). A PCR product was obtained from the mixed instar, fed gut and wandering larval cDNA libraries using standard PCR conditions (e.g., Sambrook et al., ibid.).

The resultant PCR products were used for a nested PCR amplification using the JHEHAs (SEQ ID NO:2) in combination with the JHEHsens primer having the nucleic acid sequence 5' CAR GSB GGB GAY TGG GG 3' (denoted SEQ ID NO:3). The design of the JHEHsens primer is unique because the inventors discovered a highly conserved region of epoxide hydrolase nucleic acid sequences suitable for production of a degenerate primer based on clone sequences disclosed in Roe et al., ibid. and Wojtasek et al., ibid.). The resultant PCR products, fragments of about 211 nucleotides, are denoted herein as $nEH1_{211}$ and $nEH2_{211}$. The PCR products were gel purified and cloned into the TA Vector™ (available from InVitrogen Corp., San Diego, Calif.). The nucleic acid molecule was subjected to nucleic acid sequencing using the Sanger dideoxy chain termination method, as described in Sambrook et al., ibid.

1. $nfEH1_{211}$

The flea epoxide hydrolase nucleic acid molecule isolated using the mixed instar cDNA library and the wandering larval cDNA library was determined to comprise nucleic acid molecule $nfEH1_{211}$, the nucleic acid sequence of the coding strand which is denoted herein as SEQ ID NO:4. Translation of SEQ ID NO:4 suggests that nucleic acid molecule $nfEH1_{211}$ encodes a non-full-length flea epoxide hydrolase protein of about 70 amino acids, referred to herein as $PfEH1_{70}$, having amino acid sequence SEQ ID NO:5, assuming the first codon spans from nucleotide 2 through nucleotide 4 of SEQ ID NO:4 and the last codon spans from nucleotide 209 through about nucleotide 211 of SEQ ID NO:4. The complement of SEQ ID NO:4 is represented herein by SEQ ID NO:6. Comparison of amino acid sequence SEQ ID NO:5 (i.e., the amino acid sequence of $PfEH1_{70}$) with amino acid sequences reported in GenBank indicates that SEQ ID NO:5, showed the most homology, i.e., about 45% identity, between SEQ ID NO:5 and *Manduca sexta* epoxide hydrolase. Comparison of nucleic acid sequence SEQ ID NO:4 (i.e., the nucleic acid sequence of nfEH1$_{211}$) with nucleic acid sequences reported in GenBank indicates that SEQ ID NO:4, showed the most homology, i.e., about 40% identity, between SEQ ID NO:4 and *Homo sapiens* erythropoietin gene 5' flank, including Alu repeats.

2. nfEH2$_{211}$

The flea epoxide hydrolase nucleic acid molecule isolated using the mixed instar cDNA library and the bovine blood fed gut cDNA library was determined to comprise nucleic acid molecule nfEH2$_{211}$, the nucleic acid sequence of the coding strand which is denoted herein as SEQ ID NO:19. Translation of SEQ ID NO:19 suggests that nucleic acid molecule nfEH2$_{211}$ encodes a non-full length flea epoxide hydrolase protein of about 70 amino acids, referred to herein as PfEH2$_{70}$, having amino acid sequence SEQ ID NO:20, assuming the first codon spans from nucleotide 2 through nucleotide 4 of SEQ ID NO:19 and the last codon spans from nucleotide 209 through nucleotide 211 of SEQ ID NO:19. The complement of SEQ ID NO:19 is represented herein by SEQ ID NO:21. Comparison of amino acid sequence SEQ ID NO:20 (i.e., the amino acid sequence of PfEH2$_{70}$) with amino acid sequences reported in GenBank indicates that SEQ ID NO:20 showed the most homology, i.e., about 40% identity, between SEQ ID NO:20 and *Manduca sexta* epoxide hydrolase. Comparison of nucleic acid sequence SEQ ID NO:19 (i.e., the nucleotide sequence of nfEH2$_{211}$) with nucleic acid sequences reported in GenBank indicates that SEQ ID NO:19 showed the most homology, i.e., about 40% identity between SEQ ID NO:19 and *H. sapiens* HBF-1 mRNA for transcription factor.

B. cDNA Clone

The amplified PCR fragment was used as a probe to identify a full-length flea epoxide hydrolase gene in the wandering larval cDNA library.

Nucleic acid molecule nfEH1$_{211}$ was labeled with $^{32}$P and used as a probe to screen the wandering larval cDNA library described in Section A, using standard hybridization techniques. Several clones were identified. One of the identified clones included about a 1605-nucleotide insert, referred to herein as nfEH1$_{1605}$. Nucleic acid sequence was obtained using standard techniques from nfEH1$_{1605}$ to yield a flea epoxide hydrolase nucleic acid molecule named nfEH1$_{1605}$ having a nucleic acid sequence of the coding strand which is denoted herein as SEQ ID NO:7. Translation of SEQ ID NO:7 suggests that nucleic acid molecule nfEH1$_{1605}$ encodes a full-length flea epoxide hydrolase protein of about 464 amino acids, referred to herein as PfEH1$_{464}$, having amino acid sequence SEQ ID NO:8, assuming an open reading frame having an initiation codon spanning from nucleotide 87 through nucleotide 89 of SEQ ID NO:7 and a termination codon spanning from nucleotide 1479 through nucleotide 1481 of SEQ ID NO:7. The complement of SEQ ID NO:7 is represented herein by SEQ ID NO:9. The amino acid sequence of PfEH1$_{464}$ (i.e., SEQ ID NO:8) predicts that PfEH1$_{464}$ has an estimated molecular weight of about 52.6 kD and an estimated pI of about 9.0. The nucleic acid molecule representing the coding region for PfEH1$_{464}$ is referred to herein as nfEH1$_{1392}$; the nucleic acid sequences of the coding strand and the complementary strand are represented by SEQ ID NO:10 and SEQ ID NO:12, respectively.

Analysis of SEQ ID NO:7 suggests that the sequence encodes a protein including a putative amino terminal segment of about 22 amino acids which may act as a membrane anchor; the nucleic acid molecule encoding a mature protein (i.e. the protein encoded by SEQ ID NO:7 without the 22 amino acid amino terminal segment, the amino acid sequence of which is denoted herein as SEQ ID NO:33) is denoted herein as nfEH1$_{1326}$, having a coding strand denoted herein as SEQ ID NO:32 and a complementary strand denoted herein as SEQ ID NO:34.

Comparison of nucleic acid sequence SEQ ID NO:7 with nucleic acid sequences reported in GenBank indicates that SEQ ID NO:7 showed the most homology, i.e., about 55% identity, between SEQ ID NO:7 and a *M. sexta* epoxide hydrolase gene. Comparison of amino acid sequence SEQ ID NO:8 (i.e., the amino acid sequence of PfEH1$_{464}$) with amino acid sequences reported in GenBank indicates that SEQ ID NO:8 showed the most homology, i.e., about 40% identity between SEQ ID NO:8 and a *M. sexta* epoxide hydrolase protein.

As is the case for any of the nucleic acid molecules described in this example, variations between sequences may be due to a number of factors, such as but not limited to, sequencing errors or allelic variation.

Example 2

This Example demonstrates the production of an epoxide hydrolase protein of the present invention in *E. coli* cells.

A. Flea epoxide hydrolase protein PHIS-PfEH1$_{427}$ was produced in the following manner. A pair of primers was used to amplify DNA from flea epoxide hydrolase nucleic acid molecule nfEH1$_{1605}$ produced as described in Example 1. The sense primer JHEHsignalsub, containing a BamHI site (shown in bold), having the nucleic acid sequence 5' GTA GGA TCC GAT TAC GAA AGA ACT TCC AAA ACC 3' (denoted SEQ ID NO:13), was used in combination with the anti-sense primer JHEH3' sub containing a XhoI site (shown in bold) having the nucleic acid sequence 5' AAC ACT CGA GTC ACA AAT CAG CTT TCT TTT GG 3' (denoted SEQ ID NO:14). A PCR product was derived from nfEH1$_{1605}$, and is referred to herein as nfEH1$_{1284}$ having nucleic acid sequence SEQ ID NO:15, and encoding the protein PfEH1$_{427}$, referred to herein as SEQ ID NO:16. The complement of SEQ ID NO:15 is denoted herein as SEQ ID NO:35. The PCR product was digested with BamHI and XhoI restriction endonucleases, gel purified and subcloned into expression vector pTrcHisB (available from In Vitrogen). The resultant recombinant molecule, referred to herein as pTrc-nfEH1$_{1284}$ was transformed into *E. coli* HB 101 competent cells (available from Gibco BRL) to form recombinant cell *E. coli*:pTrc-nfEH1$_{1284}$.

The recombinant cells were cultured in enriched bacterial growth medium containing 0.1 mg/ml ampicillin and 0.1% glucose at about 32° C. When the cells reached an OD$_{600}$ of about 0.4–0.5, expression of recombinant protein was induced by the addition of 0.5 mM isopropyl-B-D-thiogalactoside (IPTG), and the cells were cultured for about 2 hours at about 32° C. Immunoblot analysis of recombinant cell *E. coli*:pTrc-nfEH1$_{1284}$ lysates using a T7 tag monoclonal antibody (available from Novagen, Inc., Madison, Wis.) directed against the fusion portion of the recombinant PHIS-PfEH1$_{427}$ fusion protein identified a protein of appropriate size, namely an about 53 kD protein.

Example 3

This example describes the production of a polyclonal antiserum using PHIS-PfEH1$_{427}$.

*E. coli*:pTrc-nfEH1$_{1284}$ cells expressing PHIS-PfEH1$_{427}$ protein were harvested from about 4 liters of media and suspended in about 185 ml of 50 mM Tris, pH 8, 50 mM NaCl, 0.1 mM phenylmethylsulfonylfluoride (PMSF) (Solubilization Buffer). The cells were broken by passage through a microfluidizer at 30 psi for 30 cycles. The sample was centrifuged at about 16,000×g for 30 min at 4° C. The supernatant (S1) was recovered and the pellet was resuspended in about 150 ml of Solubilization Buffer and centrifuged at about 16,000×g for 30 min at 4° C. The supernatant (S2) was recovered and the pellet was resuspended in about 150 ml of Solubilization Buffer containing 0.1% Triton-X100 and centrifuged at about 16,000×g for 30 min at 4° C. The supernatant (S3) was recovered and the pellet was resuspended in about 150 ml Solubilization Buffer containing 8 M urea and centrifuged at about 16,000×g. The supernatant (S4) was recovered and the pellet was resuspended in 150 ml Solubilization Buffer containing 8 M urea. Aliquots of each pellet and supernatant were analyzed by SDS-PAGE and immunoblot using a T7 tag monoclonal antibody (available from Novagen, Inc., Madison, Wis.). The results indicated that the majority of the PHIS-PfEH1$_{427}$ protein was located in the final supernatant (S4). The PHIS-PfEH1$_{427}$ protein was loaded onto a 5.0 ml, Metal chelating HiTrap™ column charged with NiCl$_2$ (available from Pharmacia Biotech Inc., Piscataway, N.J.), previously equilibrated with 50 mM Tris, 1 mM PMSF, 1 mM β-mercaptoethanol (βME), 8 M urea, pH 8 (Buffer A). The column was washed with Buffer A until all unbound protein was removed. Bound PHIS-PfEH1$_{427}$ protein was eluted with a linear gradient from 0 to 1 M imidazole in 50 mM Tris, 1 mM PMSF, 1 mM βME, pH 8. Column fractions were analyzed for the presence of PHIS-PfEH1$_{427}$ protein by immunoblot using a T7 tag monoclonal antibody. The results indicated that PHIS-PfEH1$_{427}$ protein was eluted at about 300 mM imidazole. The fractions containing PHIS-PfEH1$_{427}$ protein were combined and loaded onto a 5.0 ml SP-Sepharose® HiTrap™ column (available from Pharmacia Biotech Inc.) previously equilibrated with 50 mM Tris, 25 mM Sodium Acetate, 1 mM PMSF, 1 mM βME, 8 M Urea, pH 7 (SP-Buffer). The column was washed with SP-Buffer until all unbound protein was removed. Bound protein was eluted with an increasing salt gradient from 0 to 1 M NaCl in SP-buffer. Column fractions were analyzed for the presence of PHIS-PfEH1$_{427}$ protein by immunoblot using a T7 tag monoclonal antibody. The results indicated that the PHIS-PfEH1$_{427}$ protein was eluted in two peaks, at about 0.2 M NaCl and 0.3 M NaCl. The column fractions containing the first peak of PHIS-PfEH1$_{427}$ protein were combined and diluted to a concentration of about 0.1 mg/ml in PBS.

The purified PHIS-PfEH1$_{427}$ protein was used to produce an anti-EH1 polyclonal antiserum as follows. A rabbit was immunized with the PHIS-PfEH1$_{427}$ protein that was diluted to about 0.1 mg/ml in PBS. About one milliliter of the dilution was mixed 1:1 with Complete Freunds Adjuvant. In the primary immunization, about 500 μl was injected subcutaneously into 5 different regions (0.1 ml/site) and 500 μl was injected intradermally into 5 different sites (0.1 ml/site). Boosts were administered with Incomplete Freunds Adjuvant and were given on days 20 and 41 in 250 μl/site doses intramuscularly in 4 sites. Blood samples were obtained prior to immunization (pre-bleed), and approximately every two weeks after the primary immunization. Serum samples from the pre-immunization and day 56 after the primary immunization bleeds were used for subsequent immunoblot experiments.

Example 4

This example describes the identification of epoxide hydrolase proteins in different flea tissues using the anti-EH1 polyclonal antiserum.

Tissue samples were isolated from unfed or bovine blood-fed 1$^{st}$ instar *Ctenocephalides felis* larvae; bovine blood-fed 3$^{rd}$ instar *C. felis* larvae, bovine blood-fed wandering *C. felis* larvae, bovine blood-fed prepupal *C. felis* larvae, bovine blood-fed *C. felis* pupae, unfed or cat blood-fed adult *C. felis* midgut tissue, and whole unfed or cat blood-fed adult *C. felis* fleas. The larval, pupal, and midgut tissues were homogenized by freeze-fracture and sonication in Tris buffered saline (TBS) using standard methods. The whole adult tissues were disrupted by freeze-fracture, ground with a microtube mortar and pestle and sonicated in TBS. The extracts were centrifuged at about 16,000×g for about 20 minutes and the soluble material in the supernatants removed. The pellets were then resuspended in TBS containing 0.1% Triton X-100 and diluted to a final concentration of about 1 tissue equivalent per 1 μl of TBS containing 0.1% Triton X-100. The samples were then assayed for the presence of epoxide hydrolase proteins by immunoblot analysis using the following method. The proteins contained in the tissue extract samples were resolved on a 14% Tris-glycine SDS-PAGE gel. The proteins resolved on the gel were immunoblotted using the anti-EH1 polyclonal antiserum described in Example 3, using standard methods.

The results shown in FIG. 1 indicated that all tissue extracts except the midgut tissues contained proteins of about 25 kD to 97 kD, with a dominant band at about 40 kD in the wandering, prepupal, pupal, unfed adult and fed adult samples, that were bound by the anti-EH1 polyclonal antiserum. The results indicate that these proteins contain similar epitopes as the recombinant epoxide hydrolase protein. The results also indicated that there is preferred tissue distribution and stage-specific expression of epoxide hydrolase proteins in fleas.

Example 5

This Example demonstrates the production of epoxide hydrolase protein of the present invention in eukaryotic cells.

Recombinant molecule pBv-PfEH1$_{449}$ containing a flea epoxide hydrolase nucleic acid molecule spanning nucleotides from 109 through 1458 of SEQ ID NO:7, operatively linked to baculovirus polyhedron transcription control sequences was produced in the following manner. In order to subclone a flea esterase nucleic acid molecule into baculovirus expression vectors, a flea epoxide hydrolase nucleic acid molecule-containing fragment was PCR amplified from nfEH1$_{1605}$ DNA. A PCR fragment of about 1350 nucleotides, named nfEH1$_{1350}$, was amplified from nfEH1$_{1605}$ using a JHEH forward primer having the nucleic acid sequence 5'-CCG GGA TCC TAT AAA TAT GGG TAA ATG TTG TCG TAT GC-3' (SEQ ID NO:17; BamHI site shown in bold) and the JHEH reverse primer having the nucleic acid sequence 5'-CCG TCT AGA TCA CAA ATC AGC TTT CTT TTG GC-3' (SEQ ID NO:18; XbaI site shown in bold). The N-terminal primer was designed from the pol h sequence of baculovirus with modifications to enhance expression in the baculovirus system.

In order to produce a baculovirus recombinant molecule capable of directing the production of PfEH1$_{449}$ the about 1350 base pair PCR product (referred to as Bv-nfEH1$_{1350}$) was digested with BamHI and XbaI and subcloned into unique BamHI and XbaI sites of Fast Bac™ baculovirus shuttle plasmid (obtained from Gibco-BRL) to produce the recombinant molecule referred to herein as pFB-nfEH1$_{1350}$.

The resultant recombinant molecule, pFB-nfEH1$_{1350}$, was verified for proper insert orientation by restriction mapping.

Such a recombinant molecule can be transformed into E. coli strain DH10 (obtained from Gibco-BRL) according to the manufacturer's instructions. The pFB-nfEH1$_{1350}$ isolated from the transformed DH10 cells can then be co-transfected with a linear Baculogold baculovirus DNA into S. frugiperda Sf9 cells to form the recombinant cells denoted S. frugiperda:pFB-nfEH1$_{1350}$. S. frugiperda:pFB-nfEH1$_{1350}$ can be cultured in order to produce a flea epoxide hydrolase protein PfEH1$_{449}$.

Example 6

This example describes the identification of juvenile hormone epoxide hydrolase activity in flea tissue extracts.

Tissue samples were prepared as described above in Example 4. About 15 tissue equivalents of the supernatants and pellets produced by centrifugation were tested for juvenile hormone epoxide hydrolase (JHEH) activity by the following method. Unlabeled juvenile hormone III (JH; available from ICN Biomedicals, Inc., Aurora, Ohio) was diluted in hexane to a concentration of about 0.025 M. Labeled 10-$^3$H-juvenile hormone III ($^3$H-JH; available from Dupont-NEN, Wilmington, Del.) was diluted in hexane to a concentration of about 80,000 cpm/μl. A JH substrate mixture was prepared by mixing JH and $^3$H-JH in a screw cap vial, evaporating the solvent by blanketing the substrate mixture with nitrogen, and redissolving the substrate mixture in about 1 ml of absolute anhydrous ethanol to make the final concentration of total juvenile hormone about $5\times10^{-4}$ M and about 10,000 cpm/μl. The substrate mixture was then stored at −20° C.

About 15 equivalents of each tissue (about 15 μl of soluble extracts or resuspended pellets) were added into the bottom of a small glass autosampler vial. About 84 μl of TBS and about 1 μl of ethanol or about 1 μl ethanol containing 0.3 mM 3-octylthio-1,1,1-trifluoropropan-2-one (OTFP; a juvenile hormone esterase inhibitor provided as a gift from Novartis, Inc., Basel, Switzerland) was added to each vial to bring the final volume in each vial to about 100 μl. A control sample was also prepared by adding about 100 μl TBS to a separate vial. The vials were then incubated for about 10 minutes at 35° C. About 1 μl of the substrate mixture described above was added to each of the vials to yield a final JH concentration of about $5\times10^{-6}$ M. The vials were then transferred to a heat block and incubated at about 35° C. for about 1 hour. Following the incubation, enzyme activity was stopped by adding about 50 μl of methanol buffer (methanol:water:concentrated ammonium hydroxide at a 10:9:1 ratio, respectively) to each vial and removing it from the heat block.

About 250 μl isooctane was then added to each vial to partition labeled products, which consisted of juvenile hormone diol, juvenile hormone acid, or both, into the aqueous phase. Each vial was vortexed for about 15 seconds or until an emulsion formed. Each vial was then centrifuged in a microfuge for about 1 minute to separate aqueous and organic phases. About 75 μl of the aqueous layer was removed from each vial and added to about 200 μl Optiphase Supermix scintillation fluid (available from EG&G Wallac, Gaithersburg, Md.). The total amount of labeled products was then determined using a model 1450 MicroBeta Trilux scintillation counter (available from EG&G Wallac). The data obtained from samples containing OTFP were considered to be representative of juvenile hormone epoxide hydrolase activity, while the data obtained from samples without OTFP were considered to be representative the total amount of juvenile hormone degrading activities, including juvenile hormone epoxide hydrolase (JHEH) activity and juvenile hormone esterase activity (JHE).

Figure 2:
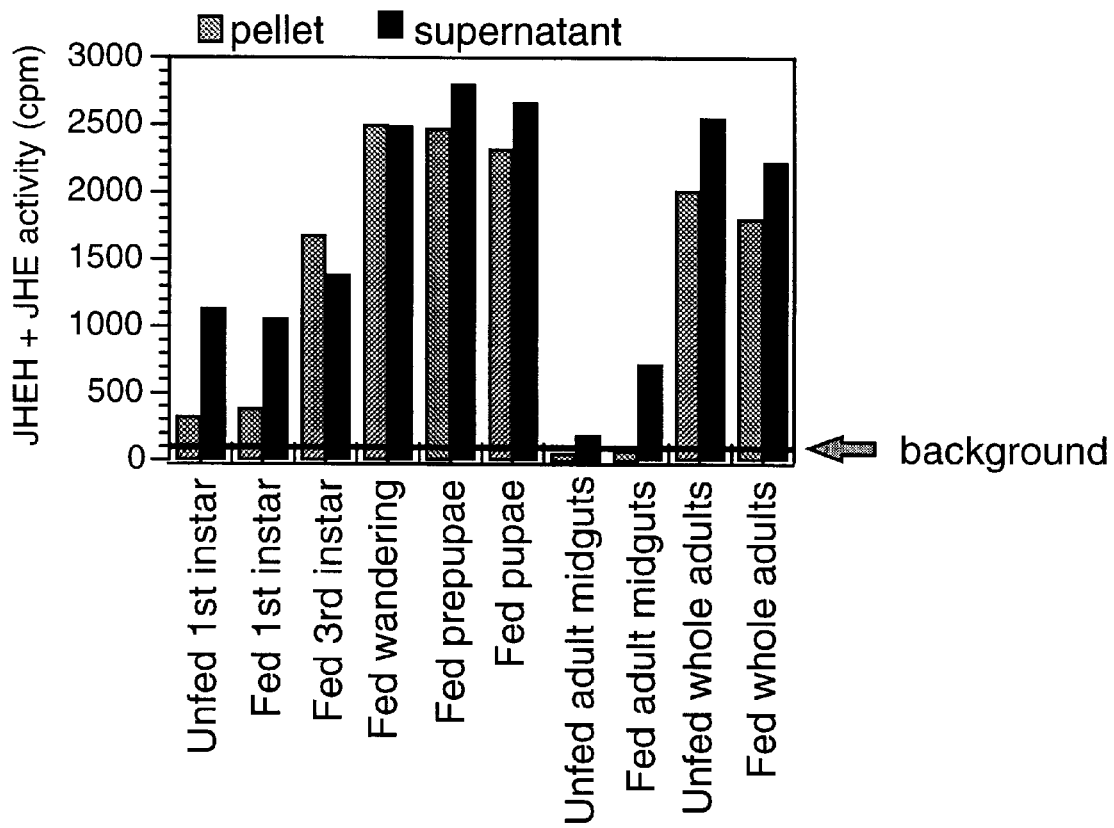
FIG. 2 illustrates levels of juvenile hormone degrading activity in different flea tissue extracts.
Figure 3:
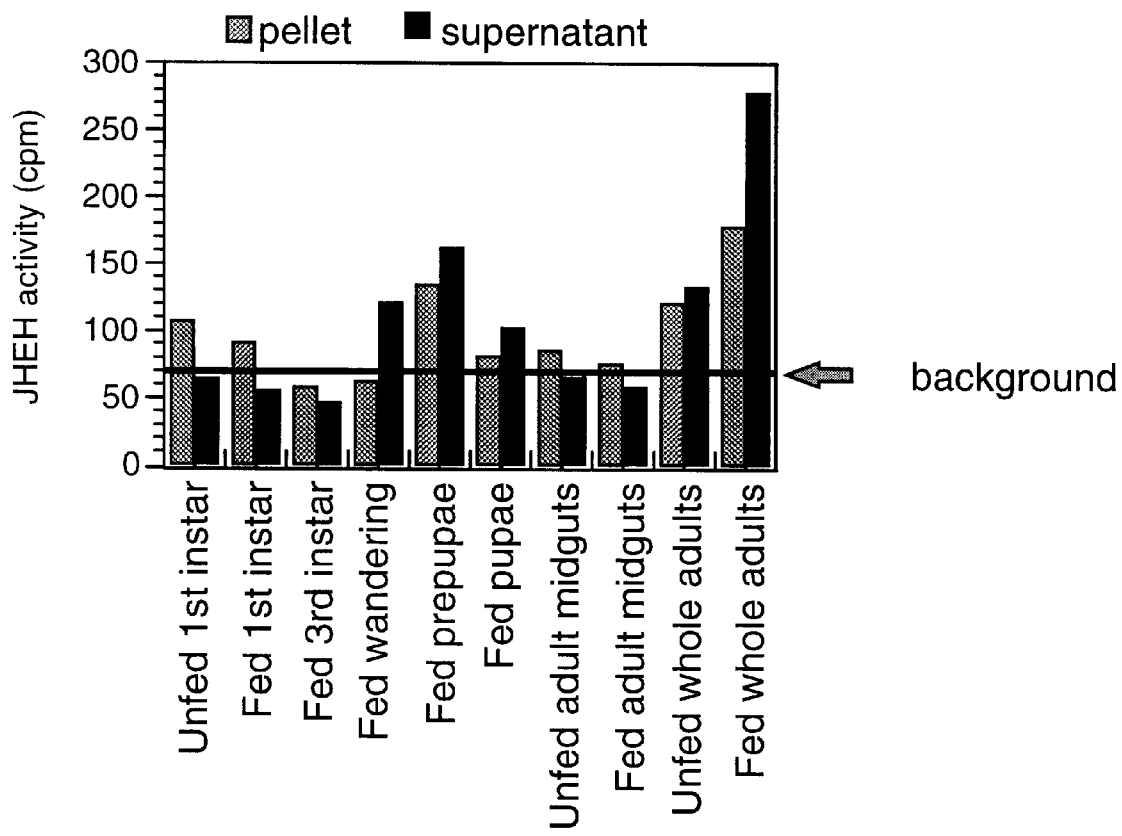
FIG. 3 illustrates levels of juvenile hormone epoxide hydrolase activity in different flea tissue extracts.

The results shown in FIG. 2 indicated that all tissues had measurable levels of JH degrading activities, and that in most tissues, the majority of the JH degrading activity is found in the supernatants. The results shown in FIG. 3 indicated that most of the tissues had measurable levels of JHEH activity, and that the JHEH activity was found both in the supernatants and pellet fractions. The level of activity varied, with wandering larvae, prepupal larvae, unfed whole adults, and fed whole adults having relatively higher levels of JHEH activity than the other tissues. Thus, the results indicated preferred tissue distribution and stage-specific expression of JHEH activity in fleas.

Example 7

This example describes the determination of JHEH activity in unfed, cat blood-fed and phosphate buffer-fed adult fleas.

Figure 4:
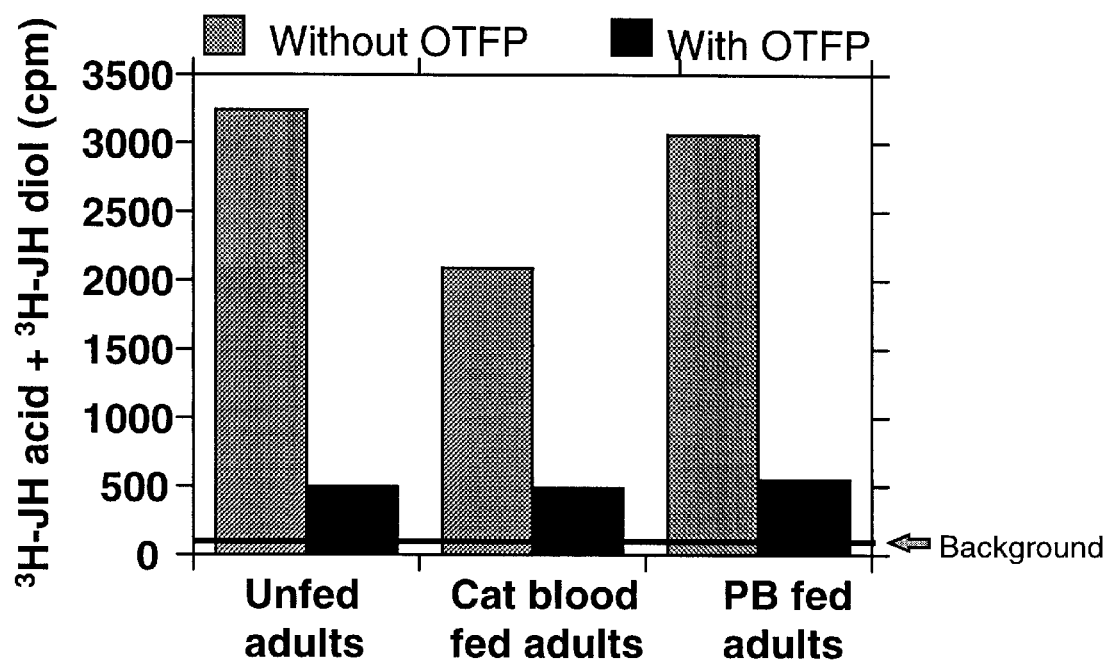
FIG. 4 illustrates juvenile hormone degrading activity in tissue extracts isolated from fleas that were unfed, fed on cat blood or fed on phosphate buffer, in the presence or absence of OTFP.

About 100 whole unfed adult Ctenocephalides felis fleas, 100 cat blood-fed adult C. felis fleas and 100 adult C. felis fleas retained in a flea saliva collection assay (described in detail in U.S. Pat. No. 5,646,115, issued Jul. 8, 1997), fed on 200 mM sodium phosphate buffer, pH 7.5, containing 0.1 unit/ml penicillin, 0.1 mg/ml streptomycin and 0.009% sodium chloride (referred to herein as PB-fed fleas) were homogenized as described above in Example 4. The extracts were clarified by centrifugation at about 740×g for 5 minutes and the supernatants recovered by aspiration. The supernatants from each of the preparations were tested, in duplicate, for JHEH activity by the method described in Example 6. The results shown in FIG. 4 indicated that in the absence of OTFP, all three extracts contained JH degrading activity. In the presence of OTFP, which inhibits JHE activity, all three extracts contained JHEH activity. Thus, the results indicate that the JHEH activity is similar in fleas that are fed or not fed.

The presence of JHEH activity was verified by assaying the reaction products for juvenile hormone diol as follows. About 60 μl of the aqueous layer from the assay mixtures described immediately above were dispensed into the bottoms of small glass autosampler vials, in which the duplicate samples were combined for a total volume of about 120 μl per vial. The reaction products $^3$H-JH diol and $^3$H-JH acid, and unreacted $^3$H-JH, were then extracted into ethyl acetate by the addition of about 120 μl of water saturated with NaCl and about 400 μl ethyl acetate. The ethyl acetate layers were removed by aspiration and dispensed into clean small glass autosampler vials. The solvent was evaporated overnight by incubation at 55° C. The samples were resuspended in about 20 μl ethyl acetate and applied to the bottom of a silica gel thin layer chromatography (TLC) plate (PE SIL G/UV plates, available from Whatman Inc., Clifton, N.J.). The $^3$H-labeled compounds were then separated with a hexane-:ethyl acetate:acetic acid (66:32:2) solvent system until the solvent front had migrated about 10 cm. After air drying, the plate was cut into about 1 cm strips and the resulting segments were placed into vials with about 1.5 ml Eco-lume scintillation fluid (available from ICN Biomedicals, Inc., Aurora, Ohio). The amount of $^3$H-labeled products contained in each vial was determined using a Beckman LS-1801 liquid scintillation counter (available from Beckman, Fullerton, Calif.). The relative mobility of JH diol, JH acid, and intact JH were determined by applying standards to the same TLC separation assay. $^3$H-JH diol was produced by reacting $^3$H-JH with purified human microsomal epoxide hydrolase (available from Gentest Corp., Woburn, Mass.) and $^3$H-JH acid was produced by reacting $^3$H-JH with purified flea JHE. Under these conditions, $^3$H-JH diol migrated about 2 cm, $^3$H-JH acid about 4 cm, and intact $^3$H-JH about 5 to 6 cm.

Figure 5:
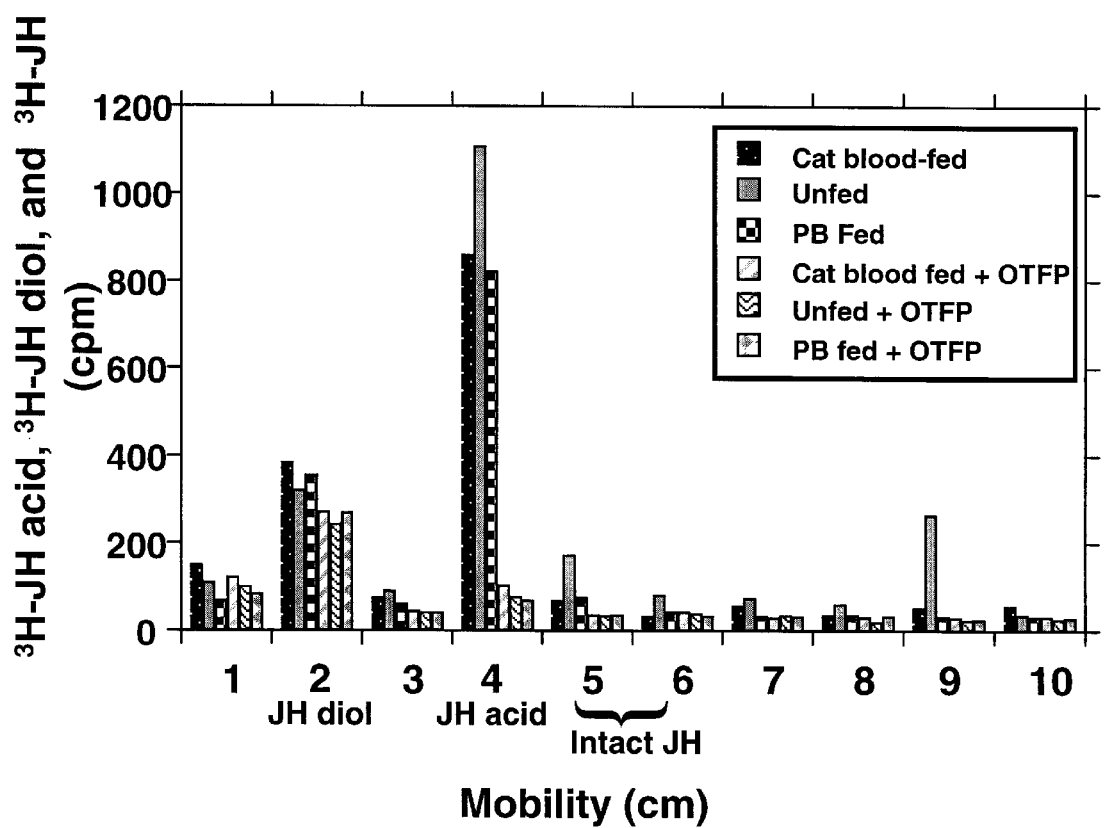
FIG. 5 illustrates $^3$H-JH diol and $^3$H-JH acid production by tissue extracts isolated from fleas that were unfed, fed on cat blood or fed on phosphate buffer, in the presence or absence of OTFP.

The results shown in FIG. 5 indicated that all three extracts produced $^3$H-JH diol and $^3$H-JH acid in the absence of OTFP, and that all three extracts produced only $^3$H-JH diol in the presence of OTFP. Thus, the results indicate that the tissue extracts contain JHEH activity.

Example 8

This example describes the determination of JHEH activity in flea membrane preparations.

Whole unfed adult *Ctenocephalides felis* fleas, cat blood-fed adult *C. felis* fleas and PB-fed adult *C. felis* fleas were homogenized and tested for JHEH activity as follows. About 4 g of fleas were frozen in liquid nitrogen and ground to a fine powder with a ceramic mortar and pestle. The powdered extract was then suspended in about 16 ml of a 10 mM Tris buffer, pH 7.5, containing 0.25 M sucrose. Intact and partially intact flea carcasses were removed from the extract by centrifugation at about 500×g for about 5 minutes and filtered through a 100 μm nylon mesh (CellMicroSieves™; available from BioDesign Inc. of New York, Carmel, N.Y.). The filtrate was then centrifuged at about 120,000×g for about 1 hour to pellet insoluble cell membranes. About 15 ml of clarified supernatant was recovered, and the pellet partially resuspended in about 0.8 ml of TBS. The pellets were then vortexed, and the resuspended proteins recovered by aspiration. To resuspend additional membrane bound proteins, about 0.4 ml of TBS containing 0.1% Triton X-100 was added to the pellet. After an about 30 minute incubation on ice, the pellets were centrifuged at about 740×g for about 5 minutes and the resuspended proteins recovered by aspiration.

Figure 6:
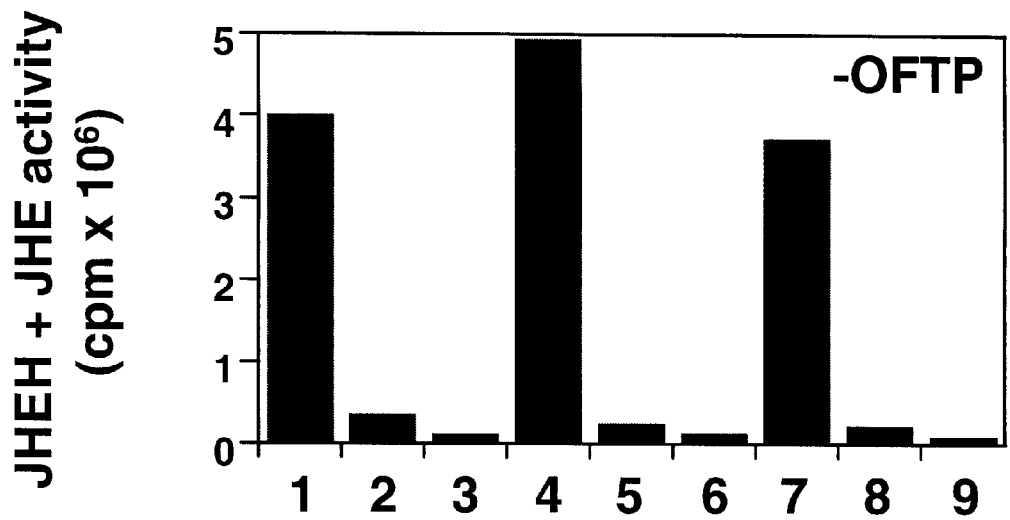
FIG. 6 illustrates the presence of juvenile hormone epoxide hydrolase activity in flea membrane preparations.
Figure 6:
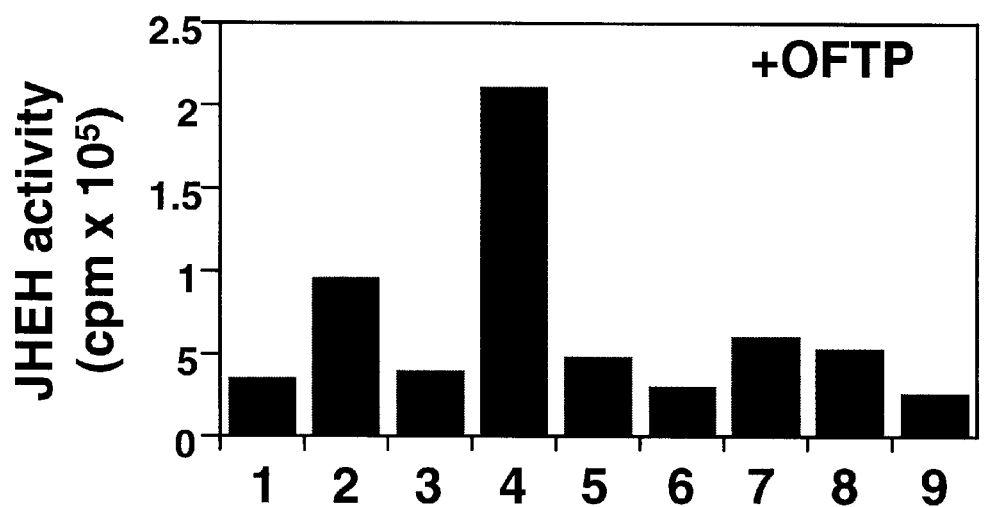

The supernatant and resuspended pellet fractions from each of the adult flea preparations were tested for $^3$H-JH degrading activity by the method described in Example 6. The results shown in FIG. 6 (–OFTP) indicated that in all three samples, about 90% of the JH degrading activity was found in the 120,000×g supernatant, and about 10% of the JH degrading activity was found in the resuspended 120,000×g pellets, when the samples were incubated in the absence of OTFP. The results also indicated that all three samples had JHEH activity in both the pellet and supernatant fractions, in the presence of OTFP (FIG. 6; +OFTP). In the unfed adult flea sample, about 21% of the JHEH activity was found in the supernatant fraction, about 56% of the JHEH activity was found in the pellet fraction resuspended in TBS, and about 23% of the JHEH activity was found in the pellet fraction resuspended in TBS containing 0.1% Triton X-100. In the cat blood-fed adult flea sample, about 73% of the JHEH activity was found in the supernatant fraction, about 17% of the JHEH activity was found in the pellet fraction resuspended in TBS, and about 10% of the JHEH activity was found in the pellet fraction resuspended in TBS containing 0.1% Triton X-100. In the PB-fed adult flea sample, about 43% of the JHEH activity was found in the supernatant fraction, about 38% of the JHEH activity was found in the pellet fraction resuspended in TBS, and about 19% of the JHEH activity was found in the pellet fraction resuspended in TBS containing 0.1% Triton X-100. Thus, in the absence of cat blood, the majority of JHEH activity in whole adult flea tissue is found in the membrane pellet.

Example 9

Nucleic acid molecule nfEH2$_{211}$ described above in Example 1 was labeled with $^{32}$P and used as a probe to screen the wandering larval cDNA library described above in Example 1, using the following hybridization conditions. Filters were hybridized with about 5×10$^5$ cpm/mL of the probe in 5×SSPE, 1% Sarcosyl, and 5×Denhardts reagent at 45° C. for about 24 hours. The filters were washed twice for 40 minutes per wash in 250 mL of 1×SSPE, 0.5% Sarcosyl at 55° C. Several clones were identified. One of the identified clones included an about 1736-nucleotide insert, referred to herein as nfEH2$_{1736}$. Nucleic acid sequence was obtained from nfEH2$_{1736}$ using standard techniques to yield a flea epoxide hydrolase nucleic acid molecule named nfEH2$_{1736}$ having a nucleic acid sequence of the coding strand which is denoted herein as SEQ ID NO:22 Translation of SEQ ID NO:22 suggests that nucleic acid molecule nfEH2$_{1736}$ encodes a full-length flea epoxide hydrolase protein of about 465 amino acids, referred to herein as PfEH2$_{465}$, having amino acid sequence SEQ ID NO:23, assuming an open reading frame having an initiation codon spanning from nucleotide 159 through nucleotide 161 of SEQ ID NO:22 and a termination codon spanning from nucleotide 1554 through nucleotide 1556 of SEQ ID NO:22. The complement of SEQ ID NO:22 is represented herein by SEQ ID NO:24. The amino acid sequence of PfEH2$_{465}$ (i.e., SEQ ID NO:23) predicts that PfEH2$_{465}$ has an estimated molecular weight of about 53 kD and an estimated pI of about 9. The nucleic acid molecule representing the coding region for PfEH2$_{465}$ is referred to herein as nfEH2$_{1395}$; the nucleic acid sequences of the coding strand and the complementary strand are represented by SEQ ID NO:25 and SEQ ID NO:26, respectively.

Analysis of SEQ ID NO:22 suggests that the sequence includes a putative amino terminal segment of about 22 amino acids which may act as a membrane anchor. The putative anchor spans from amino acid 1 to amino acid 22 of SEQ ID NO:23.

Comparison of nucleic acid sequence SEQ ID NO:22 with nucleic acid sequences reported in GenBank indicates that SEQ ID NO:22 showed the most homology, i.e., about 52% identity, between SEQ ID NO:22 and a *T. ni* epoxide hydrolase gene. Comparison of amino acid sequence SEQ ID NO:23 (i.e., the amino acid sequence of PfEH2$_{465}$) with amino acid sequences reported in GenBank indicates that SEQ ID NO:23 showed the most homology, i.e., about 44% identity between SEQ ID NO:23 and a *T. ni* epoxide hydrolase protein.

As is the case for any of the nucleic acid molecules described in this example, variations between sequences may be due to a number of factors, such as but not limited to, sequencing errors or allelic variation.

Example 10

This Example demonstrates the production of an epoxide hydrolase protein of the present invention in *E. coli* cells.

A. Flea epoxide hydrolase protein PHIS-PfEH2$_{430}$, represented herein as SEQ ID NO:28 was produced in the following manner. A pair of primers was used to amplify DNA from flea epoxide hydrolase nucleic acid molecule nfEH2$_{1736}$ produced as described above in Example 9. The sense primer newEHexp-sigsen', containing a BamHI site (shown in bold), having the nucleic acid sequence 5' AAA GGA TCC GAT AAC TAA AGA ATT TCC 3' (denoted SEQ ID NO:29), was used in combination with the anti-sense primer newEHexpanti, containing a EcoRI site (shown in bold) having the nucleic acid sequence 5' ATT GAA TTC TCA GAG ATC TCT ATT CTC TTG G 3' (denoted SEQ ID NO:30). A PCR product was derived from nfEH2$_{1736}$, and is referred to herein as nfEH2$_{1293}$ having nucleic acid sequence SEQ ID NO:27, which encodes a protein referred to herein as PfEH2$_{430}$, represented by SEQ ID NO:28. The amino acid sequence of the PCR product was digested with BamHI and EcoRI restriction endonucleases, gel purified and subcloned into expression vector pTrcHisB (available from In Vitrogen, San Diego, Calif.). The resultant recombinant molecule, referred to herein as pTrc-nfEH2$_{1293}$ was transformed into E. coli BL-21 competent cells (available from Novagen) to form recombinant cell E. coli:pTrc-nfEH2$_{1293}$.

The recombinant cells were cultured in enriched bacterial growth medium containing 0.1 mg/ml ampicillin and 0.1% glucose at about 32° C. When the cells reached an OD$_{600}$ of about 0.4–0.5, expression of recombinant protein was induced by the addition of 0.5 mM isopropyl-B-D-thiogalactoside (IPTG), and the cells were cultured for about 2 hours at about 32° C. Immunoblot analysis of recombinant cell E. coli:pTrc-nfEH2$_{1293}$ lysates using a T7 tag monoclonal antibody (available from Novagen) directed against the fusion portion of the recombinant PHIS-PfEH2$_{430}$ fusion protein identified a protein of appropriate size, namely an about 54 kD protein.

Example 11

This example describes the production of a polyclonal antiserum using PHIS-PfEH2$_{430}$.

E. coli:pTrc-nfEH2$_{1293}$ cells expressing PHIS-PfEH2$_{430}$ protein were harvested from about 4 liters of media and suspended in about 185 ml of 50 mM Tris, pH 8, 50 mM NaCl, 0.1 mM phenylmethylsulfonylfluoride (PMSF; Solubilization Buffer). The cells were broken by sonication with lysosyme (2 min. for 2 second cycles). The sample was centrifuged at about 20,000×g for 30 min at 4° C. The supernatant (S1) was recovered and the pellet was resuspended in about 40 ml of Solubilization Buffer and centrifuged at about 20,000×g for 30 min at 4° C. The supernatant (S2) was recovered and the pellet was resuspended in about 150 ml of Solubilization Buffer containing 0.1% Triton-X100 and centrifuged at about 16,000×g for 30 min at 4° C. The supernatant (S3) was recovered and the pellet was resuspended in about 40 ml Solubilization Buffer containing 8 M urea and centrifuged at about 20,000×g. The supernatant (S4) was recovered and the pellet was resuspended in 40 ml Solubilization Buffer containing 8 M urea. Aliquots of each pellet and supernatant were analyzed by SDS-PAGE and immunoblot using a T7 tag monoclonal antibody (available from Novagen). The results indicated that the majority of the PHIS-PfEH2$_{430}$ protein was located in the final supernatant (S4). The PHIS-PfEH2$_{430}$ protein was then loaded onto a 5.0 ml, metal chelating HiTrap™ column charged with NiCl$_2$ (available from Pharmacia Biotech Inc., Piscataway, N.J.), previously equilibrated with 50 mM Tris, 1 mM PMSF, 1 mM β-mercaptoethanol (βME), 8 M urea, pH 8 (Buffer A). The column was washed with Buffer A until all unbound protein was removed. Bound PHIS-PfEH2$_{430}$ protein was eluted from the column with a linear gradient from 0 to 1 M imidazole in 50 mM Tris, 1 mM PMSF, 1 mM βME, pH 8. Column fractions were analyzed for the presence of PHIS-PfEH2$_{430}$ protein by immunoblot using a T7 tag monoclonal antibody. The results indicated that PHIS-PfEH2$_{430}$ protein was eluted at about 300 mM imidazole. The fractions containing PHIS-PfEH2$_{430}$ protein were combined and loaded onto a 5 ml SP-Sepharose® HiTrap™ column (available from Pharmacia Biotech Inc.) previously equilibrated with 50 mM Tris, 25 mM Sodium Acetate, 1 mM PMSF, 1 mM bME, 8 M Urea, pH 7 (SP-Buffer). The column was washed with SP-Buffer until all unbound protein was removed. Bound protein was eluted with an increasing salt gradient from 0 to 1 M NaCl in SP-buffer. Column fractions were analyzed for the presence of PHIS-PfEH2$_{430}$ protein by immunoblot using a T7 tag monoclonal antibody. The results indicated that the PHIS-PfEH2$_{430}$ protein was eluted in two peaks, at about 0.2 M NaCl and 0.3 M NaCl. The column fractions containing the first peak of PHIS-PfEH2$_{430}$ protein were combined and diluted to a concentration of about 0.1 mg/ml in PBS.

The purified PHIS-PfEH2$_{430}$ protein is used to produce an anti-EH2 polyclonal antiserum as follows. A rabbit is immunized with the PHIS-PfEH2$_{430}$ protein that is diluted to about 0.1 mg/ml in PBS. About 1 ml of the dilution is mixed 1:1 with Complete Freunds Adjuvant. In the primary immunization, about 500 ml is injected subcutaneously into 5 different regions (0.1 ml/site) and 500 ml is injected intradermally into 5 different sites (0.1 ml/site). Boosts are administered with Incomplete Freunds Adjuvant and are given on days 20 and 41 in 250 ml/site doses intramuscularly in 4 sites. Blood samples are obtained prior to immunization (pre-bleed), and approximately every two weeks after the primary immunization.

Example 12

This example describes the solubilization and stabilization of juvenile hormone epoxide hydrolase from phosphate buffer-fed adult fleas.

About 60 grams of phosphate buffer-fed adult Ctenocephalides felis fleas retained in a flea saliva collection assay (described in detail in U.S. Pat. No. 5,646,115, issued Jul. 8, 1997), fed on 200 mM sodium phosphate buffer, pH 7.5, containing 0.1 unit/ml penicillin, 0.1 mg/ml streptomycin and 0.009% sodium chloride (referred to herein as PB-fed fleas) were frozen in liquid nitrogen and ground to a fine powder with a previously chilled ceramic mortar and pestle. The pulverized fleas were then suspended in about 120 ml of 10 mM Tris buffer, pH 7.5, containing 10% (w/w) sucrose. Intact and partially intact flea carcasses were removed from the extract by centrifugation at about 500×g for about 5 minutes and filtration through a 100 µm nylon mesh (CellMicroSieves™; available from BioDesign Inc. of New York, Carmel, N.Y.). The filtrate was centrifuged at about 100,000×g for 1 hour to pellet insoluble cell membranes. The pellet was resuspended in about 13 ml of Tris buffered saline (TBS, comprised of 50 mM Tris, pH 8.0, 150 mM NaCl) to produce a solubilized membrane preparation. The protein concentration of the resuspended pellet was about 3 mg/ml as determined by the Bio-Rad Protein Assay, using bovine serum albumin as a standard.

Nine detergents comprising detergents from the Detergent Trial Set (available from Boehringer Mannheim, Indianapolis), Ind. and Brij 35 (both available from Sigma, St. Louis, Mo.) were tested to determine which detergent best preserved juvenile hormone epoxide hydrolase (JHEH) activity and which detergent best solubilized JHEH from membranes. Nine different samples were prepared using either about 0.5 µl of 2 mg Digitonin/ml methanol, about 1.2 µl of 40% n-Dodecylmaltoside, about 1.7 µl of 40% n-Octylglucoside, about 0.5 µl of 10% Nonidet® P-40, 0.5 µl of 10% Triton® X-100, about 0.5 µl of 10% Tween® 20, about 5 µl of 10% Deoxycholic acid, about 1 µl of 40% CHAPS, or about 0.5 µl of 10% Brij 35, combined with aliquots of the solubilized membrane preparation to a final volume of about 50 µl per sample. The samples were incubated for about 6 hours at 4° C. The samples were then assayed for JHEH activity using the method described above in Example 6. The results indicated that the detergents that preserved >85% of the JHEH activity included n-Octylglucoside, Nonidet P-40, Triton X-100, Tween 20, CHAPS, and Brij 35.

Six different samples were then prepared using either about 33 µl of 40% n-Octylglucoside, about 10 µl of 10% Nonidet P-40, about 10 µl of 10% Triton X-100, about 10 µl of 10% Tween 20, about 20 µl of 40% CHAPS, or about 10 µl of 10% Brij 35 combined with aliquots of the solubilized membrane pellet so that the total volume of each sample was about 1 ml. After an about 1 hour incubation at 4° C., the detergent mixtures were centrifuged at about 100,000×g for about 1 hour. The resulting pellet was resuspended in TBS to yield a final protein concentration of about 3 mg/ml. The resuspended proteins were recovered by aspiration and assayed for JHEH activity. The results indicated that more JHEH activity was detected in the sample using Nonidet P-40 compared with the sample containing Brij 35, which had more activity than the sample containing Triton X-100.

Several protease inhibitors, including phenylmethylsulfonyl fluoride (PMSF; available from Sigma), dithiothreitol (DTT; available from Boeringer Mannheim), ethylenediaminetetraacetic acid (EDTA; available from Amresco, Solon, Ohio), and the protease inhibitor cocktail Mini Complete™ (available from Boeringer Mannheim), were each tested to determine which best preserved JHEH activity. Multiple membrane samples were prepared and resuspended in TBS to give a protein concentration of about 3 mg/ml as described immediately above, combined with either 1×Mini Complete™, 1 mM PMSF, 1 mM DTT, or 1 mM EDTA, in a total volume of 400 µl per sample. Control samples were also prepared which did not include a protease inhibitor. After overnight incubation at 4° C., equivalent amounts of each sample were assayed for JHEH activity.

The results indicated that the sample containing PMSF had about 7% more activity than the control samples. Samples containing the other protease inhibitors had about a 20%–60% loss of activity when compared to the control samples. In addition, preliminary experiments indicated that PMSF inhibits flea juvenile hormone esterase (JHE), a juvenile hormone degrading enzyme that must be inhibited in order to accurately measure JHEH activity. When combined, these results indicated that it is beneficial to add PMSF to JHEH preparations and JHEH activity assays.

Example 13

This example describes the identification and partial purification of juvenile hormone epoxide hydrolase (JHEH) from PB-fed adult fleas.

A. Identification and Partial Purification of JHEH

JHEH protein was purified from about 560 grams of PB-fed fleas by the following method. Batches of about 112 grams of PB-fed fleas were frozen in liquid nitrogen and ground to a fine powder with a previously chilled ceramic mortar and pestle. The pulverized fleas were then suspended in about 300 ml of 10 mM Tris buffer, pH 7.5, containing 10% (w/w) sucrose. The resulting mixture was sonicated 6 times, for 30 seconds each time, at a setting of 4 on a model W-380 Sonicator (available from Heat Systems-Ultrasonics, Inc., Farmingdale, N.Y.). Intact and partially intact flea carcasses were removed from the extract by centrifugation at about 500×g for about 5 minutes. The resulting supernatant was filtered through a 100 µm nylon mesh and retained, and the resulting pellet was washed with an additional 60 ml of 10 mM Tris buffer, pH 7.5, containing 10% (w/w) sucrose. The resuspended pellet was briefly vortexed, centrifuged at 500×g for about 5 minutes, and filtered through a 100 µm nylon mesh to remove remaining flea carcasses. The clarified extract and pellet-wash were combined, filtered through two layers of 100 µm nylon mesh and centrifuged at about 100,000×g for 1 hour to pellet insoluble cell membranes. The pellet was resuspended in TBS to create a suspension that contained about 6 mg/ml protein as determined by the Bio-Rad Protein Assay, using bovine serum albumin as a standard. Membrane proteins in the pellet suspension were solubilized by supplementing the extract with 0.5% Brij 35 and 0.5 mM PMSF. After stirring slowly for about 2 hours at 4° C., the extract was clarified by centrifugation at about 100,000×g for 1 hour. The resulting supernatant (referred to herein as "100,000×g supernatant") was assayed for JHEH activity as described in Example 6. The results indicated that >90% of initial JHEH activity in the membrane pool was recovered in the 100,000×g supernatant.

Epoxide hydrolase proteins present in the membrane preparation[s] were detected by immunoblot using polyclonal anti-EH1 antibodies purified from the anti-EH1 polyclonal antiserum described above in Example 3, by the following method. About 2.3 mg of PHIS-PfEH1$_{427}$ protein was coupled to 0.5 ml of pre-swollen (143 mg) CNBr-activated Sepharose 4B gel (Pharmacia, Piscataway, N.J.). About 40 ml of PBS was added to about 36 ml of anti-EH1 polyclonal antiserum. After extensive washing with PBS, polyclonal antibodies that bound specifically to PHIS-PfEH1$_{427}$ protein were eluted from the column using 0.1 M glycine, pH 2.7. The resulting eluate was adjusted to pH 7 by the addition of 1 M sodium monophosphate. The protein concentration of the affinity purified anti-EH1 antibody was about 80 µg/ml as determined by absorbance at 280 nm and using an extinction coefficient of 1.4.

The presence of epoxide hydrolase proteins in samples of solubilized membrane preparations were assayed by immunoblot analysis using the following method. The proteins contained in the 100,000×g supernatant described above were resolved on a 14% Tris-glycine SDS-PAGE gel (available from Novex, San Diego, Calif.). The proteins resolved on the gel were transferred to nitrocellulose and the membrane was immunoblotted using 0.6 µg of affinity-purified anti-EH1 antibodies using standard methods. Bands were detected on the blot, indicating the presence of JHEH proteins in the 100,000×g supernatant.

B. Purification of Two JHEH Proteins

Proteins in different samples of the 100,000×g supernatant were precipitated in increasing concentrations of ammonium sulfate ranging from about 35–55% saturating ammonium sulfate. Each sample was centrifuged for about 30 min at 17,500×g. The resulting protein pellets in each sample were dissolved in a minimum volume of TBS containing 0.1% Brij 35 and 0.1 mM PMSF. The dissolved pellets were then assayed for JHEH activity. as well as for the presence of JHEH proteins by immunoblot using affinity-purified anti-EH1 antibodies.

The dissolved 35–45% ammonium sulfate pellet (pellet A sample) and 45–55% ammonium sulfate pellet (pellet B sample) were separately purified by anion exchange chromatography on a UNO Q6 column (available from Bio-Rad). After equilibrating the column in 25 mM Bis-Tris pH 7, with 10 mM NaCl, 0.1 mM PMSF, and 0.1% Brij 35, the pellet A sample and the pellet B sample were loaded onto separate columns and then eluted with a linear gradient of 10 to 1000 mM NaCl. Resulting column fractions were assayed for JHEH activity and for the presence of JHEH proteins by immunoblot using affinity-purified anti-EH1 antibodies. Two peaks having JHEH activity were detected in fractions using either pellet A or pellet B samples. The first peak with JHEH activity eluted with the flow-through while the second eluted within the 50 to 200 mM NaCl range. Each peak contained a protein of about 50 kDa identified using the anti-EH1 antibody. JHEH recovery was greater than 90%. Approximately 50% of the recovered activity was in the flow-through, and approximately 50% was in the eluate.

The 50 to 200 mM NaCl eluate from the pellet A UNO Q6 run, referred to herein as UNO Q6A$_{EL1}$, was pooled and combined with the 50 to 200 mM NaCl eluate from the pellet B UNO Q6 run, referred to herein as UNO Q6B$_{EL1}$. The combined mixture is referred to herein as the UNO Q6A$_{EL1}$+B$_{EL1}$ pool. The UNO Q6A$_{EL1}$+B$_{EL1}$ pool was loaded onto a UNO Q6 column and the column was eluted under the same conditions as described above to produce a UNO Q6A$_{EL2}$+B$_{EL2}$ pool. The UNO Q6A$_{EL2}$+B$_{EL2}$ pool was assayed for JHEH activity. The majority, >80%, of the JHEH was recovered in the second UNO Q6A$_{EL1}$+B$_{EL1}$ pool. This result indicated that the UNO Q6 column was able to separate two forms of JHEH, one of which had little affinity for the column and was found in the flow-through, and the other of which had a strong affinity for the column and was eluted with 100 to 250 mM NaCl.

C. Purification of Two JHEH Proteins

The flow-through from the pellet A UNO Q6 run, referred to herein as UNO Q6A$_{FT}$, was combined with the flow-through from the pellet A UNO Q6 run, referred to herein as UNO Q6B$_{FT}$. The combined mixture is referred to herein as UNO Q6A$_{FT}$+B$_{FT}$ pool. The UNO Q6A$_{EL2}$+B$_{EL2}$ pool or the UNO Q6A$_{FT}$+B$_{FT}$ pool were loaded on separate Macro-Prep Ceramic Hydroxyapatite Type II columns (available from Bio-Rad). Proteins bound to the columns were eluted with increasing concentration of phosphate buffer, 10–500 mM phosphate buffer at pH 7 with 10 mM NaCl, 0.1% Brij 35, or 0.1 mM PMSF. JHEH protein was eluted from 50 to 200 mM phosphate from both columns. Column fractions were assayed for JHEH activity and for the presence of JHEH proteins by immunoblot using affinity-purified anti-EH1 antibodies. Based on JHEH activity, about >95% JHEH activity was recovered from the Hydroxyapatite columns. Also, the same fractions containing JHEH activity contained protein of about 50 kDa identified using the anti-EH1 antibody.

Hydroxyapatite fractions containing JHEH activity from each column were pooled creating two separate pools. The pooled hydroxyapatite fractions were concentrated using Ultrafree-20 10 kDa centrifugal concentrators (available from Millipore, Bedford, Mass.). Proteins in the two concentrated samples were then resolved on a reducing, 12% SDS-PAGE Tris glycine gel (available from Novex). The proteins on the gel were then electroblotted onto a ProBlott™ polyvinylidene difluoride membrane (available from Applied BioSystems, Foster City, Calif.). Proteins bound to the membrane were stained for 1 minute with 0.1% Coomassie Blue R-250 dissolved in 40% methanol and 1% acetic acid. The membrane was destained in 50% methanol for about 10 minutes and air dried. A protein band of about 50 kDa from each hydroxyapatite fraction pool was cut out of the membrane and subjected to N-terminal amino acid sequencing using a 494 Protein Sequencer (available from Applied Biosystems) and using standard techniques.

The results indicated that the N-terminal amino acid sequence of the 50 kDa band from each hydroxyapatite fraction pool was GKxxRMLIFAAIAGIAVLYYQITKE (denoted SEQ ID NO:31), in which "x" designates any residue. SEQ ID NO:31 is 100% identical to residues 2 through 26 of SEQ ID NO:8 (PfEH1$_{464}$), the amino acid sequence from the cDNA clone nfEH1$_{1605}$ (SEQ ID NO:7), when the undetermined residues in SEQ ID NO:31 are translated to be consistent with the cysteines in SEQ ID NO:8. N-terminal amino acid sequencing using standard techniques does not alkylate native cysteines, and non-alkylated cysteines are not determinable residues using standard N-terminal sequencing techniques. Therefore, identification of the two cysteine residues in the native protein would be predicted to be undeterminable by N-terminal sequencing using standard techniques. SEQ ID NO:31 is 56% identical to residues 2 through 26 of SEQ ID NO:23 (PfEH2$_{465}$), the amino acid sequence from the cDNA clone nfEH2$_{1736}$ (SEQ ID NO:22).

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated protein encoded by a nucleic acid molecule that hybridizes under stringent hybridization conditions with a nucleic acid molecule having a nucleic acid sequence selected from the group consisting of SEQ ID NO:6, SEQ ID NO:9, SEQ ID NO:12, SEQ ID NO:21, SEQ ID NO:24, SEQ ID NO:26, SEQ ID NO:34 and SEQ ID NO:35, wherein said nucleic acid molecule encodes an epoxide hydrolase.

2. The protein of claim 1, wherein said protein is encoded by a nucleic acid molecule selected from the group consisting of $nfEH1_{211}$, $nfEH2_{211}$, $nfEH1_{1605}$, $nfEH1_{1350}$, $nfEH1_{1392}$, $nfEH1_{1326}$, $nfEH1_{1284}$, $nfEH2_{1736}$, $nfEH2_{1395}$ and $nfEH2_{1293}$.

3. The protein of claim 1, wherein said protein is encoded by a nucleic acid molecule comprising a nucleic acid sequence selected from the group consisting of SEQ ID NO:4, SEQ ID NO:7, SEQ ID NO:10, SEQ ID NO:15, SEQ ID NO:19, SEQ ID NO:22, SEQ ID NO:25, SEQ ID NO:27 and SEQ ID NO:32.

4. The protein of claim 1, wherein said protein is selected from the group consisting of: a protein comprising an amino acid sequence selected from the group consisting of SEQ ID NO:5, SEQ ID NO:8, SEQ ID NO:11, SEQ ID NO:16, SEQ ID NO:20, SEQ ID NO:23, SEQ ID NO:28, SEQ ID NO:31, and SEQ ID NO:33; and a protein encoded by an allelic variant of a nucleic acid molecule encoding a protein comprising an amino acid sequence selected from the group consisting of SEQ ID NO:5, SEQ ID NO:8, SEQ ID NO:11, SEQ ID NO:16, SEQ ID NO:20, SEQ ID NO:23, SEQ ID NO:28, SEQ ID NO:31, and SEQ ID NO:33.

5. A method to identify a compound capable of inhibiting hematophagous ectoparasite epoxide hydrolase activity, said method comprising:

(a) contacting an isolated protein of claim 1 with a putative inhibitory compound under conditions in which, in the absence of said compound, said protein has epoxide hydrolase activity; and (b) determining if said putative inhibitory compound inhibits said activity.

6. The method of claim 5, wherein said protein is selected from the group consisting of: a protein comprising an amino acid sequence selected from the group consisting of SEQ ID NO:5, SEQ ID NO:8, SEQ ID NO:11, SEQ ID NO:16, SEQ ID NO:20, SEQ ID NO:23, SEQ ID NO:28, SEQ ID NO:31, and SEQ ID NO:33; and a protein encoded by an allelic variant of a nucleic acid molecule encoding a protein comprising an amino acid sequence selected from the group consisting of SEQ ID NO:5, SEQ ID NO:8, SEQ ID NO:11, SEQ ID NO:16, SEQ ID NO:20, SEQ ID NO:23, SEQ ID NO:28, SEQ ID NO:31, and SEQ ID NO:33.

7. A test kit to identify a compound capable of inhibiting hematophagous ectoparasite epoxide hydrolase activity, said test kit comprising an isolated protein of claim 1 having epoxide hydrolase activity and a means for determining the extent of inhibition of said activity in the presence of a putative inhibitory compound.

8. The kit of claim 7, wherein said protein is selected from the group consisting of: a protein comprising an amino acid sequence selected from the group consisting of SEQ ID NO:5, SEQ ID NO:8, SEQ ID NO:11, SEQ ID NO:16, SEQ ID NO:20, SEQ ID NO:23, SEQ ID NO:28, SEQ ID NO:31, and SEQ ID NO:33; and a protein encoded by an allelic variant of a nucleic acid molecule encoding a protein comprising an amino acid sequence selected from the group consisting of SEQ ID NO:5, SEQ ID NO:8, SEQ ID NO:11, SEQ ID NO:16, SEQ ID NO:20, SEQ ID NO:23, SEQ ID NO:28, SEQ ID NO:31, and SEQ ID NO:33.

9. A composition comprising an excipient and an isolated protein encoded by a nucleic acid molecule that hybridizes under stringent hybridization conditions with a nucleic acid molecule having a nucleic acid sequence selected from the group consisting of SEQ ID NO:6, SEQ ID NO:9, SEQ ID NO:12, SEQ ID NO:21, SEQ ID NO:24, SEQ ID NO:26, SEQ ID NO:34, and SEQ ID NO:35, wherein said nucleic acid molecule encodes an epoxide hydrolase.

10. The composition of claim 9, wherein said composition further comprises a component selected from the group consisting of an adjuvant and a carrier.

11. The composition of claim 9, wherein said protein is encoded by a nucleic acid molecule selected from the group consisting of $nfEH1_{211}$, $nfEH2_{211}$, $nfEH1_{1605}$, $nfEH1_{1350}$, $nfEH1_{1392}$, $nfEH1_{1326}$, $nfEH1_{1284}$, $nfEH2_{1736}$, $nfEH2_{1395}$ and $nfEH2_{1293}$.

12. The composition of claim 9, wherein said protein is encoded by a nucleic acid molecule comprising a nucleic acid sequence selected from the group consisting of SEQ ID NO:4, SEQ ID NO:7, SEQ ID NO:10, SEQ ID NO:15, SEQ ID NO:19, SEQ ID NO:22, SEQ ID NO:25, SEQ ID NO:27, and SEQ ID NO:32.

13. The composition of claim 9, wherein said protein is selected from the group consisting of: a protein comprising an amino acid sequence selected from the group consisting of SEQ ID NO:5, SEQ ID NO:8, SEQ ID NO:11, SEQ ID NO:16, SEQ ID NO:20, SEQ ID NO:23, SEQ ID NO:28, SEQ ID NO:31, and SEQ ID NO:33; and a protein encoded by an allelic variant of a nucleic acid molecule encoding a protein comprising an amino acid sequence selected from the group consisting of SEQ ID NO:5, SEQ ID NO:8, SEQ ID NO:11, SEQ ID NO:16, SEQ ID NO:20, SEQ ID NO:23, SEQ ID NO:28, SEQ ID NO:31, and SEQ ID NO:33.

* * * * *